US009637792B2

(12) United States Patent
Ahlquist et al.

(10) Patent No.: US 9,637,792 B2
(45) Date of Patent: May 2, 2017

(54) DIGITAL SEQUENCE ANALYSIS OF DNA METHYLATION

(75) Inventors: David A. Ahlquist, Rochester, MN (US); William R. Taylor, Lake City, MN (US); Hongzhi Zou, Middleton, WI (US); Graham P. Lidgard, Madison, WI (US)

(73) Assignees: MAYO FOUNDATION FOR MEDICAL EDUCATION AND RESEARCH, Rochester, MN (US); EXACT SCIENCES CORPORATION, Madison, WI (US)

( * ) Notice: Subject to any disclaimer, the term of this patent is extended or adjusted under 35 U.S.C. 154(b) by 357 days.

(21) Appl. No.: 13/364,978

(22) Filed: Feb. 2, 2012

(65) Prior Publication Data

US 2012/0196756 A1    Aug. 2, 2012

Related U.S. Application Data

(60) Provisional application No. 61/438,649, filed on Feb. 2, 2011.

(51) Int. Cl.
  *C12Q 1/68*    (2006.01)
(52) U.S. Cl.
  CPC ......... *C12Q 1/6886* (2013.01); *C12Q 1/6827* (2013.01); *C12Q 1/6858* (2013.01); *C12Q 2600/154* (2013.01)
(58) Field of Classification Search
  None
  See application file for complete search history.

(56) References Cited

U.S. PATENT DOCUMENTS

| | | | |
|---|---|---|---|
| 4,458,066 A | 7/1984 | Caruthers et al. | |
| 4,683,195 A | 7/1987 | Mullis et al. | |
| 4,683,202 A | 7/1987 | Mullis | |
| 4,965,188 A | 10/1990 | Mullis et al. | |
| 5,011,769 A | 4/1991 | Duck et al. | |
| 5,124,246 A | 6/1992 | Urdea et al. | |
| 5,288,609 A | 2/1994 | Engelhardt et al. | |
| 5,338,671 A | 8/1994 | Scalice et al. | |
| 5,352,775 A | 10/1994 | Albertsen et al. | |
| 5,403,711 A | 4/1995 | Walder et al. | |
| 5,409,818 A | 4/1995 | Davey et al. | |
| 5,494,810 A | 2/1996 | Barany et al. | |
| 5,508,169 A | 4/1996 | Deugau et al. | |
| 5,527,676 A | 6/1996 | Vogelstein et al. | |
| 5,624,802 A | 4/1997 | Urdea et al. | |
| 5,639,611 A | 6/1997 | Wallace et al. | |
| 5,648,212 A | 7/1997 | Albertsen et al. | |
| 5,660,988 A | 8/1997 | Duck et al. | |
| 5,710,264 A | 1/1998 | Urdea et al. | |
| 5,741,650 A | 4/1998 | Lapidus et al. | |
| 5,773,258 A | 6/1998 | Birch et al. | |
| 5,792,614 A | 8/1998 | Western et al. | |
| 5,846,717 A | 12/1998 | Brow et al. | |
| 5,849,481 A | 12/1998 | Urdea et al. | |
| 5,882,867 A | 3/1999 | Ullman et al. | |
| 5,914,230 A | 6/1999 | Liu et al. | |
| 5,952,178 A | 9/1999 | Lapidus et al. | |
| 5,955,263 A | 9/1999 | Vogelstein et al. | |
| 5,965,408 A | 10/1999 | Short | |
| 5,985,557 A | 11/1999 | Prudent et al. | |
| 5,994,069 A | 11/1999 | Hall et al. | |
| 6,001,567 A | 12/1999 | Brow et al. | |
| 6,013,170 A | 1/2000 | Meade | |
| RE36,713 E | 5/2000 | Vogelstein et al. | |
| 6,063,573 A | 5/2000 | Kayyem | |
| 6,090,543 A | 7/2000 | Prudent et al. | |
| 6,090,566 A | 7/2000 | Vogelstein et al. | |
| 6,110,677 A | 8/2000 | Western et al. | |
| 6,121,001 A | 9/2000 | Western et al. | |
| 6,143,496 A | 11/2000 | Brown et al. | |
| 6,150,097 A | 11/2000 | Tyagi et al. | |
| 6,183,960 B1 | 2/2001 | Lizardi | |
| 6,210,884 B1 | 4/2001 | Lizardi | |
| 6,221,583 B1 | 4/2001 | Kayyem et al. | |
| 6,235,502 B1 | 5/2001 | Weissman et al. | |
| 6,245,515 B1 | 6/2001 | Vogelstein et al. | |

(Continued)

FOREIGN PATENT DOCUMENTS

| WO | 03/044232 | 5/2003 |
|---|---|---|
| WO | 03/064701 | 8/2003 |

(Continued)

OTHER PUBLICATIONS

Abe et al., "CpG island methylator phenotype is a strong determinant of poor prognosis in neuroblastomas," Cancer Res, 2005, 65:828-834.
Ballabio, et al., "Screening for steroid sulfatase (STS) gene deletions by multiplex DNA amplification," Human Genetics, 1990, 84(6) 571-573.
Barnay, "Genetic disease detection and DNA amplification using cloned thermostable ligase," Proc. Natl. Acad. Sci USA, 1991, 88, 189-93.
Baylin et al., "Epigenetic gene silencing in cancer—a mechanism for early oncogenic pathway addiction?" Nat. Rev. Cancer, 2006, 6:107-116.
Baylin et al., "Alterations in DNA methylation: a fundamental aspect of neoplasia," Adv Cancer Res 1998;72:141-19.
Beaucage et al., "Deoxynucleoside phosphoramidites—A new class of key intermediates for deoxypolynucleotide synthesis," Tetrahedron Lett., 1981, 22: 1859-1862.

(Continued)

*Primary Examiner* — Mindy G Brown
(74) *Attorney, Agent, or Firm* — Casimir Jones, S.C.; Mary Ann Brow

(57) ABSTRACT

The present invention relates to methods and compositions for determination of and uses of specific methylation patterns indicative of adenoma and carcinoma. In particular, the invention relates to analysis of defined CpG loci that are coordinately methylated in DNAs from cancer and adenoma samples, methods for identifying coordinately methylated loci, and methods of using analysis of coordinately methylated loci in one or more marker regions in the design of assays for adenoma and cancer.

8 Claims, 34 Drawing Sheets

(56) References Cited

U.S. PATENT DOCUMENTS

| | | | |
|---|---|---|---|
| 6,248,229 | B1 | 6/2001 | Meade |
| 6,268,136 | B1 | 7/2001 | Shuber et al. |
| 6,303,304 | B1 | 10/2001 | Shuber et al. |
| 6,391,559 | B1 | 5/2002 | Brown et al. |
| 6,440,706 | B1 | 8/2002 | Vogelstein et al. |
| 6,677,312 | B1 | 1/2004 | Vogelstein et al. |
| 6,753,147 | B2 | 6/2004 | Vogelstein et al. |
| 6,800,617 | B1 | 10/2004 | Vogelstein et al. |
| 6,872,816 | B1 | 3/2005 | Hall et al. |
| 7,005,266 | B2 | 2/2006 | Sprenger-Haussels |
| 7,087,583 | B2 | 8/2006 | Vogelstein et al. |
| 7,267,955 | B2 | 9/2007 | Vogelstein et al. |
| 7,432,050 | B2 | 10/2008 | Markowitz |
| 7,459,315 | B2 | 12/2008 | Brown |
| 7,485,420 | B2 | 2/2009 | Markowitz |
| 7,611,869 | B2 | 11/2009 | Fan |
| 7,662,594 | B2 | 2/2010 | Kong et al. |
| 2004/0132048 | A1 | 7/2004 | Martienssen et al. |
| 2005/0003463 | A1 | 1/2005 | Adorjan et al. |
| 2007/0059753 | A1* | 3/2007 | Vener et al. ............. 435/6 |
| 2007/0202525 | A1 | 8/2007 | Quake et al. |
| 2008/0254474 | A1* | 10/2008 | Laird et al. ............. 435/6 |
| 2009/0253142 | A1 | 10/2009 | Allawi et al. |
| 2010/0092981 | A1 | 4/2010 | Shuber |
| 2010/0144867 | A1 | 6/2010 | Barany et al. |
| 2010/0273164 | A1 | 10/2010 | Church et al. |

FOREIGN PATENT DOCUMENTS

| | | |
|---|---|---|
| WO | 2005023091 | 3/2005 |
| WO | 2010/118016 | 10/2010 |

OTHER PUBLICATIONS

Bentley et al, "Accurate whole human genome sequencing using reversible terminator chemistry," Nature, 2008, 456:53-59.

Brown et al., "Chemical synthesis and cloning of a tyrosine tRNA gene," Meth Enzymol., 1979, 68:109-151.

Bustin, "Absolute quantification of mRNA using real-time reverse transcription polymerase chain reaction assays," J. Molecular Endocrinology, 2000, 25:169-193.

Chamerlain et al., "Deletion screening of the Duchenne muscular dystrophy locus via multiplex DNA amplification," Nucleic Acids Research, 1988, 16(23):11141-11156.

Craig et al., "Identification of genetic variants using bar-coded multiplexed sequencing," Nat. Methods Nat Methods., 2008, 5(10):887-93.

Don et al., "'Touchdown' PCR to circumvent spurious priming during gene amplification," Nucleic Acids Research, 1991, 19(14):4008.

Eads et al., "Epigenetic patterns in the progression of esophageal adenocarcinoma," Cancer Res, 2001, 61:3410-3418.

Estellar et al., "Hypermethylation-associated inactivation of p14(ARF) is independent of p16(INK4a) methylation and p53 mutational status," Cancer Res, 2000, 60:129-133.

Garcia-Manero et al., "DNA methylation of multiple promoter-associated CpG islands in adult acute lymphocytic leukemia," Clin Cancer Res, 2002, 8:2217-2224.

Gardiner-Garden et al., "CpG islands in vertebrate genomes," J Mol. Biol., 1987, 196:261-282.

Glockner et al., "Methylation of TFPI2 in Stool DNA: A Potentional Novel Biomarker for the Detection of Colorectal Cancer," Cancer Res, 2009. 69:4691-4699.

Grutzmann et al., Sensitive Detection of Colorectal Cancer in Peripheral Blood by Septin 9 DNA Methylation Assay PLoS ONE, 2008, 3(11):e3759.

Guilfoyle et al., "Ligation-mediated PCR amplification of specific fragments from a class-II restriction endonuclease total digest," Nucleic Acids Research, 1997, 25:1854-1858.

Hall et al., "Sensitive detection of DNA polymorphisms by the serial invasive signal amplification reaction," PNAS, 2000, 97:8272.

Hecker et al., "High and low annealing temperatures increase both specificity and yield in touchdown and stepdown PCR," Biotechniques, 1996, 20(3):478-485.

Herman et al., "Methylation-specific PCR: a novel PCR assay for methylation status of CpG islands," PNAS, 1996, 93(13):9821-9826.

Higuchi et al., "A general method of in vitro preparation and specific mutagenesis of DNA fragments: study of protein and DNA interactions," Nucleic Acids Research, 1988, 16(15):7351-7367.

Higuchi et al., "Kinetic PCR analysis: real-time monitoring of DNA amplification reactions," Biotechnology, 1993, 11:1026-1030.

Higuchi et al., "Simultaneous amplification and detection of specific DNA sequences," Biotechnology, 1992, 10:413-417.

Irizarry et al., "The human colon cancer methylome shows similar hypo- and hypermethylation at conserved tissue-specific CpG island shores," Nat. Genetics, 2009, 41:178-186.

Issa et al., "CIMP, at Last," Gastroenterology, 2005 129(3):1121-1124.

Jones et al., "The fundamental role of epigenetic events in cancer," Nat Rev Genet, 2002, 3:415-428.

Kalinina et al., "Nanoliter scale PCR with TaqMan detection," Nucleic Acids Research, 1997, 25:1999-2004.

Keshet et al., "Evidence for an instructive mechanism of de novo methylation in cancer cells," Nature Genetics, 2006, 38:149-153.

Lyamichev et al., "Polymorphism identification and quantitative detection of genomic DNA by invasive cleavage of oligonucleotide probes," Nat. Biotech., 1999, 17:292-296.

Matteucci et al., "Synthesis of deoxyoligonucleotides on a polymer support," J Am Chem Soc., 1981, 103:3185-3191.

Narang et al., "Improved phosphotriester method for the synthesis of gene fragments," Meth Enzymol., 1979, 68: 90-98.

Pfeifer et al., "Methylated-CpG island recovery assay-assisted microarrays for cancer diagnosis," Expert Opinion on Medical Diagnostics, 2007, 1(1):99-108.

Roux, "Using mismatched primer-template pairs in touchdown PCR," Biotechniques, 1994, 16(5):812-814.

Schouten et al., "Relative quantification of 40 nucleic acid sequences by multiplex ligation-dependent probe amplification," Nucleic Acids Research, 2002, 30(12): e57.

Shen et al., "DNA methylation and environmental exposures in human hepatocellular carcinoma," J Natl Cancer Inst, 2002, 94:755-761.

Strathdee et al., "Primary ovarian carcinomas display multiple methylator phenotypes involving known tumor suppressor genes," Am J Pathol, 2001, 158:1121-1127.

DNA Methylation and Cancer Therapy, Landes Bioscience, 2005, ed. Moshe Szyf (TOC only).

Takai et al., "Comprehensive analysis of CpG islands in human chromosomes 21 and 22," PNAS, 2007, 99:3740-3745.

Tena-Tomas et al., ""A globally occurring indel polymorphism in the promoter of theIFNA2 gene is not associated with severity of malaria but with the positivity rate of HCV," BMC Genetics, 2008, 9:80".

Toyota et al., "Methylation profiling in acute myeloid leukemia," Blood, 2001, 97:2823-2829.

Toyota et al., "Aberrant methylation in gastric cancer associated with the CpG island methylator phenotype," Cancer Res, 1999, 59:5438-5442.

Toyota et al., "CpG island methylator phenotype in colorectal cancer," PNAS, 1999, 96:8681-8686.

Triglia et al., "A procedure for in vitro amplification of DNA segments that lie outside the boundaries of known sequences," Nucleic Acids Res., 1999, 16:8186.

Ueki et al., "Hypermethylation of multiple genes in pancreatic adenocarcinoma," Cancer Res, 2000, 60:1835-1839.

Van Rijnsoever et al., "Characterisation of colorectal cancers showing hypermethylation at multiple CpG islands," Gut, 2002, 51:797-802.

Vogelstein et al., "Digital PCR," PNAS, 1999, 96: 9236-41.

Weber et al., "Chromosome-wide and promoter-specific analyses identify sites of differential DNA methylation in normal and transformed human cells," Nature Genetics, 2005, 37(8):853-862.

(56) References Cited

OTHER PUBLICATIONS

Whitehall et al., "Morphological and molecular heterogeneity within nonmicrosatellite instability—high colorectal cancer," Cancer Res, 2002, 62:6011-6014.
Yamashita et al., "Genetics supersedes epigenetics in colon cancer phenotype," Cancer Cell, 2003, 4:121-131.
Zou et al., "Highly Methylated Genes in Colorectal Neoplasia: Implications for Screening Cancer," Epidemiol Biomarkers Prev, 2007, 16:2686-2696.
International Search Report for International Patent Application PCT/US2012/023646, mailed Feb. 2, 2012, 13 pages.
Ahlquist, Molecular detection of colorectal neoplasia, Gastroenterology, 2010, 138:2127-2139.
Weisenberger et al., DNA methylation analysis by digital bisulfite genomic sequencing and digital MethyLight, Nucleic Acids Res, 2008, 36:4689-98.
Zou et al., Sensitive Quantification of Vimentin Methylation with a Novel Methylation Specific qInvader Technology, AACC Annual Meeting Jul. 28, 2010, Abstract No. D-144, 1 page.
Extended European Search Report for EP12742758.1, issued Oct. 8, 2015, 8 pages.

\* cited by examiner

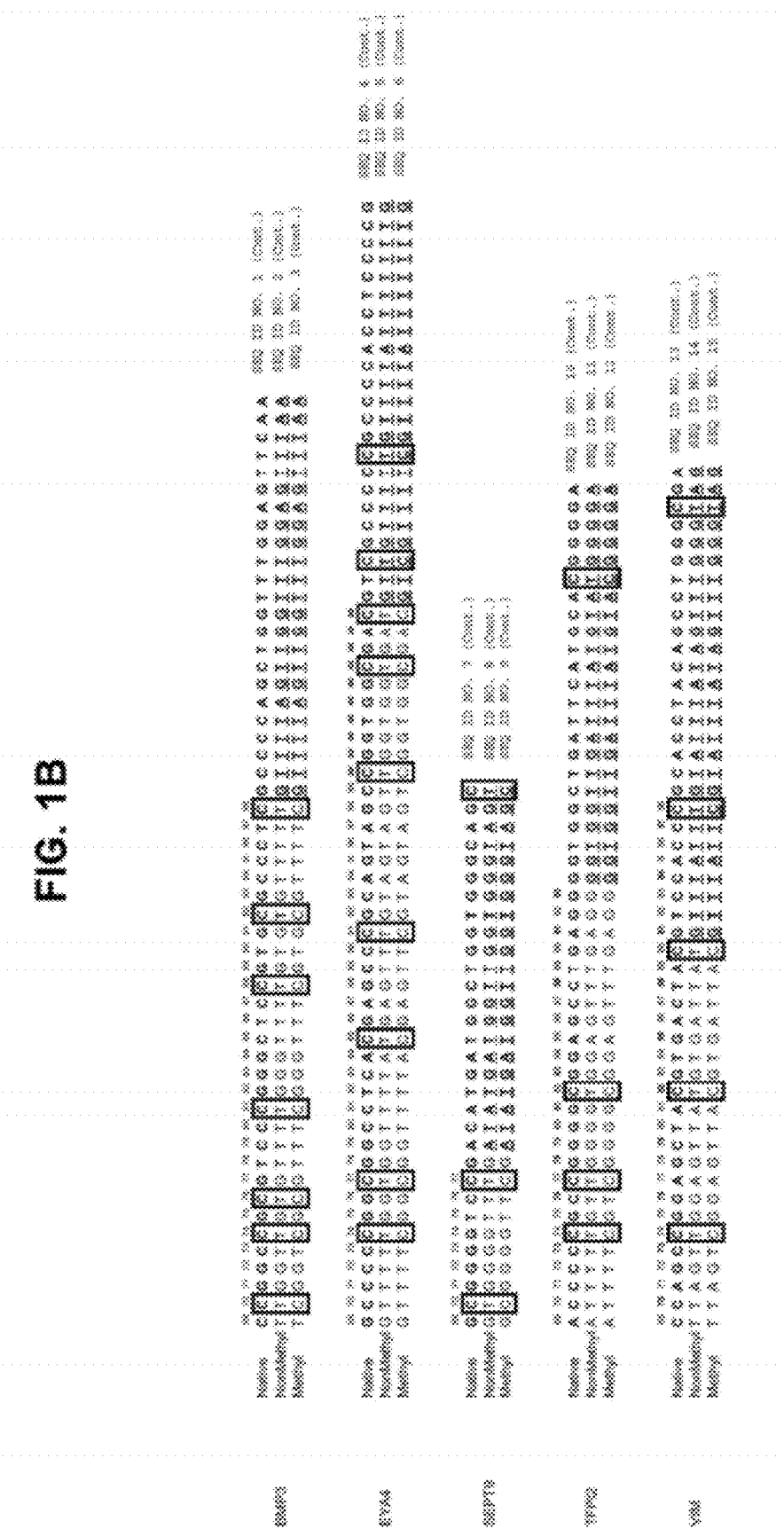

FIG. 2A

| Vimentin | | | | | | | | | | |
|---|---|---|---|---|---|---|---|---|---|---|
| CpG | 36 | 37 | 40 | 45 | 52 | 54 | 59 | 63 | 74 | |
| NORMAL | | | | | | | | | | Mean |
| 8-4 | 11.63 | 6.08 | 6.52 | 3.52 | 3.65 | 2.31 | 3.44 | 3.86 | 3.88 | 4.99 |
| 8-5 | 8.93 | 3.4 | 2.97 | 1.26 | 1.19 | 0.3 | 2.61 | 0.97 | 1.14 | 2.53 |
| 8-6 | 12.23 | 8.92 | 5.06 | 4.01 | 2 | 2.45 | 2.27 | 3.44 | 5.21 | 5.07 |
| 8-7 | 15.74 | 9.41 | 5.7 | 6.72 | 3.73 | 5.26 | 5.92 | 4.29 | 4.46 | 6.80 |
| 8-8 | 6.48 | 2.52 | 2.71 | 1.73 | 4.26 | 3.14 | 1.67 | 1.87 | 2.64 | 3.22 |
| 8-9 | 5.65 | 2.48 | 1.27 | 1.48 | 1.5 | 0.87 | 1.7 | 1.03 | 3.18 | 2.24 |
| 8-10 | 5.36 | 2.77 | 1.89 | 2.84 | 2.09 | 0.85 | 1.89 | 1.97 | 2.55 | 2.38 |
| 8-11 | 7.5 | 3.68 | 2.34 | 1.66 | 4.9 | 4.84 | 1.71 | 3.5 | 3.94 | 3.57 |
| 8-12 | 5.91 | 5.13 | 3.52 | 1.91 | 2.53 | 2.27 | 1.84 | 1.86 | 1.58 | 2.95 |
| Mean | 8.60444 | 4.81667 | 3.47556 | 2.90222 | 2.87222 | 2.49889 | 2.56111 | 2.70889 | 3.08778 | 3.73 |
| | | | | | | | | SD all | | 3.68 |
| | | | | | | | | M+2SD | | 9.09 |
| | | | | | | | | M+3SD | | 11.77 |

| CpG | 36 | 37 | 40 | 45 | 52 | 54 | 59 | 63 | 74 | |
|---|---|---|---|---|---|---|---|---|---|---|
| ADENOMA | | | | | | | | | | Mean |
| 3-4 | 50.2 | 52.6 | 47 | 24.66 | 31.46 | 16.34 | 20.96 | 37.91 | 36.05 | 33.02 |
| 3-5 | 79.04 | 70.33 | 65.88 | 56.54 | 33.15 | 29.8 | 35.34 | 32.14 | 40.84 | 48.72 |
| 3-6 | 37.08 | 33.91 | 32.94 | 25.06 | 13.78 | 15.64 | 23.57 | 23.22 | 29.4 | 28.18 |
| 3-7 | 47.73 | 46.01 | 44.87 | 42.42 | 41.78 | 41.34 | 41.83 | 41.75 | 40.02 | 42.92 |
| 3-8 | 56.11 | 48.88 | 46.52 | 44.12 | 41.36 | 41.34 | 41.29 | 40.82 | 43.15 | 44.83 |
| 3-9 | 6.49 | 3.18 | 4.26 | 2.93 | 3.28 | 2.87 | 3.55 | 2.17 | 3.46 | 3.46 |
| 3-10 | 5.7 | 2.61 | 4.61 | 2.02 | 2.77 | 2.46 | 3.2 | 2.15 | 3.01 | 3.06 |
| 3-11 | 86.54 | 84.38 | 83.07 | 41.43 | 43.76 | 51.8 | 77.13 | 76.74 | 48.14 | 65.55 |
| 3-12 | 90.13 | 90.15 | 88.53 | 88.89 | 88.89 | 85.22 | 83.03 | 83.48 | 83.35 | 86.85 |
| 5-1 | 71.75 | 71.01 | 70.12 | 65.83 | 72.49 | 71.45 | 69.97 | 61.89 | 65.53 | 68.87 |
| 5-2 | 39.07 | 35.75 | 33.57 | 31.84 | 31.98 | 31.84 | 30.25 | 30.1 | 30.97 | 32.82 |
| 5-4 | 40.85 | 33.71 | 17.84 | 21.28 | 18.47 | 20.19 | 20.5 | 23.79 | 40.53 | 26.24 |
| 5-11 | 70.93 | 70.52 | 69.58 | 64.06 | 70.39 | 70.52 | 68.51 | 60.3 | 63.66 | 67.61 |
| 5-12 | 84.36 | 84.75 | 84.36 | 77.41 | 73.36 | 57.52 | 49.02 | 68.93 | 79.15 | 73.21 |
| 6-1 | 87.8 | 86.44 | 87.45 | 86.38 | 85.89 | 82.83 | 84.12 | 80.86 | 80.54 | 84.71 |
| 6-2 | 50.08 | 46.81 | 40.99 | 37.87 | 36.69 | 32.82 | 32.63 | 39.06 | 39.44 | 39.59 |
| 6-3 | 68.73 | 67.13 | 59.29 | 60.01 | 55.34 | 55.21 | 49.64 | 54.93 | 55.63 | 58.43 |
| 6-4 | 59.32 | 59.36 | 53.82 | 43.22 | 42.23 | 39.54 | 44.19 | 45.19 | 38.26 | 47.21 |
| 6-5 | 18.51 | 8.39 | 8.37 | 4.44 | 3.34 | 2.17 | 3.35 | 2.1 | 0.4 | 5.61 |
| 6-6 | 55.32 | 54.47 | 53.14 | 43.9 | 38.87 | 39.01 | 34.58 | 36.08 | 39.69 | 43.89 |
| 7-5 | 71.06 | 70.46 | 71.36 | 70.54 | 70.78 | 70.65 | 68.07 | 63.9 | 64.36 | 69.02 |
| 7-6 | 58.18 | 55.35 | 49.14 | 45.4 | 42.42 | 45.59 | 53.06 | 44.81 | 47.71 | 48.96 |
| 7-7 | 20.5 | 16.52 | 15.05 | 12.88 | 12 | 11.08 | 12.63 | 11.37 | 10.61 | 13.63 |
| 7-8 | 28.05 | 20.31 | 22.19 | 13.34 | 15.5 | 10.57 | 19.98 | 18.19 | 17.36 | 18.39 |
| 7-9 | 79.93 | 79.58 | 78.49 | 78.5 | 78.21 | 76.44 | 75.8 | 72.93 | 68.5 | 76.46 |
| 7-10 | 80.88 | 81.15 | 80.46 | 80.04 | 79.32 | 77.6 | 76.5 | 74.09 | 70.63 | 77.85 |
| 7-11 | 22.15 | 12.4 | 10.05 | 5.74 | 7.02 | 2.31 | 6.61 | 6.09 | 9.06 | 9.05 |
| 7-12 | 33.99 | 32.48 | 33.46 | 31.53 | 32.34 | 31.36 | 31.44 | 29.17 | 30.14 | 31.77 |
| 8-1 | 48.74 | 49.22 | 50.37 | 48.32 | 50.05 | 50.83 | 50.9 | 49.21 | 47.73 | 49.49 |
| 8-2 | 83.35 | 82.4 | 82.33 | 81.75 | 81.4 | 81.89 | 80.65 | 79.84 | 78.95 | 81.39 |
| 8-3 | 63.16 | 63.53 | 65.87 | 65.06 | 64.39 | 64.34 | 62.43 | 62.08 | 61.29 | 63.57 |
| Mean | 54.4742 | 51.9945 | 50.0690 | 45.0771 | 43.9571 | 42.5803 | 43.5974 | 43.3555 | 44.2245 | |
| N/M | 0.15795 | 0.09271 | 0.06942 | 0.06438 | 0.06534 | 0.05875 | 0.05874 | 0.06248 | 0.07005 | |

FIG. 2B

| Vimentin CpG | 26 | 37 | 40 | 45 | 52 | 54 | 59 | 63 | 74 | |
|---|---|---|---|---|---|---|---|---|---|---|
| CANCER | | | | | | | | | | Mean |
| 1-1 | 55.95 | 46.38 | 39.19 | 39.35 | 39.25 | 38.19 | 30.93 | 26.81 | 33.13 | 38.80 |
| 1-2 | 46.07 | 48.23 | 39.2 | 26.64 | 33.32 | 21.46 | 34.99 | 27.12 | 35.62 | 34.74 |
| 1-3 | 38.4 | 23.79 | 25.7 | 3.9 | 6.22 | 4.83 | 4.54 | 4.83 | 6.72 | 13.19 |
| 1-4 | 80.52 | 66.55 | 81.59 | 80.93 | 80.51 | 81.01 | 79.67 | 70.78 | 76.98 | 77.62 |
| 1-5 | 86.12 | 85.72 | 85.71 | 85.99 | 85.66 | 86.21 | 84.61 | 81.46 | 82.86 | 84.93 |
| 1-6 | 76.07 | 75.28 | 76.89 | 75.46 | 74.46 | 75.74 | 74.47 | 70.81 | 57.16 | 72.92 |
| 1-7 | 11.26 | 13.06 | 28.2 | 7.2 | 5.52 | 2.47 | 3.57 | 2.88 | 3.34 | 8.57 |
| 1-8 | 3.24 | 2.4 | 3.04 | 3.05 | 3.85 | 4.58 | 3.05 | 2.85 | 3.19 | |
| 1-9 | 91.73 | 91.67 | 90.09 | 90.69 | 91.4 | 87.87 | 88.51 | 72.39 | 75.96 | 86.69 |
| 1-10 | 91.81 | 91.44 | 90.57 | 91.05 | 91.41 | 88.35 | 88.74 | 71.95 | 75.29 | 86.73 |
| 1-11 | 86.17 | 85.74 | 84.23 | 85.46 | 86.33 | 55.84 | 45.36 | 53.85 | 55.95 | 72.01 |
| 1-12 | 81.46 | 70.09 | 58.63 | 49.52 | 49.5 | 39.87 | 40.96 | 34.12 | 29.02 | 49.26 |
| 2-1 | 3.3 | 2.71 | 2.37 | 2.63 | 4.47 | 1.65 | 3.08 | 2.32 | 2.88 | 2.81 |
| 2-2 | 27.81 | 27.74 | 28.16 | 24.33 | 27.01 | 26.02 | 25.55 | 19.5 | 21.84 | 25.33 |
| 2-3 | 50.74 | 50.46 | 50.99 | 50.06 | 50.1 | 50.5 | 48.51 | 47.2 | 46.41 | 49.44 |
| 2-4 | 49.58 | 48.5 | 49.13 | 42.39 | 48.89 | 40.01 | 47.42 | 35.7 | 43.83 | 45.03 |
| 2-5 | 5.4 | 3.66 | 3.69 | 3.1 | 3.06 | 2.56 | 2.54 | 2.58 | 4.21 | 3.42 |
| 2-6 | 39.3 | 39.04 | 39.7 | 38.66 | 39.38 | 38.32 | 37.14 | 36.43 | 36.53 | 38.28 |
| 2-7 | 55.36 | 54.9 | 54.89 | 54.26 | 55.2 | 55.07 | 54.09 | 51.47 | 51.4 | 54.05 |
| 2-8 | 62.61 | 62.07 | 65.43 | 61.37 | 53.91 | 63.71 | 63.75 | 58.15 | 57.97 | 61.55 |
| 2-9 | 5.64 | 4.28 | 1.97 | 2.06 | 3.83 | 3.36 | 6.47 | 3.86 | 3.97 | 3.94 |
| 2-10 | 4.96 | 3.92 | 1.36 | 1.52 | 3.48 | 2.24 | 5.74 | 1.94 | 2.33 | 3.05 |
| 2-11 | 88.83 | 87.81 | 89.74 | 86.33 | 88.17 | 84.68 | 80.4 | 77.3 | 81.63 | 84.97 |
| 2-12 | 50.01 | 47.56 | 57 | 32.01 | 44.13 | 40.93 | 33.52 | 30.48 | 45.93 | 43.51 |
| 3-2 | 45.95 | 45.94 | 46.18 | 45.91 | 35.78 | 46.43 | 44.81 | 43.34 | 42.49 | 45.20 |
| 3-3 | 30.38 | 39.55 | 39.08 | 38.44 | 30.71 | 30.97 | 38.13 | 37.42 | 38.37 | 39.27 |
| 3-5 | 19.85 | 17.44 | 8.57 | 7.31 | 3.29 | 3.22 | 2.82 | 2.82 | 5.57 | 8.72 |
| 3-6 | 9.19 | 15.8 | 3.9 | 4.11 | 10.38 | 3.48 | 2.23 | 9.98 | 13.18 | 8.90 |
| 3-7 | 52.6 | 51.71 | 39.08 | 34.92 | 25.58 | 28.83 | 38.34 | 45.32 | 48.14 | 40.50 |
| 3-8 | 21.65 | 20.89 | 20.89 | 19.08 | 22.4 | 21.76 | 21.76 | 19.51 | 19.4 | 20.77 |
| 3-9 | 44.3 | 43.83 | 43.37 | 39.74 | 44.14 | 41.53 | 38.83 | 39.41 | 40.88 | 40.55 |
| 3-10 | 43.44 | 41.51 | 43.53 | 40.36 | 42.76 | 40.94 | 38.62 | 37.06 | 39.38 | 39.62 |
| 6-7 | 91.08 | 90.06 | 90.06 | 90.28 | 89.75 | 90.85 | 88.49 | 84.97 | 85.04 | 88.95 |
| 6-8 | 65.53 | 62.59 | 59.24 | 58.03 | 51.16 | 50.98 | 53.92 | 58.67 | 60.01 | 57.90 |
| 6-9 | 7.35 | 4.62 | 4.49 | 2.5 | 3.93 | 4.24 | 5.55 | 4.66 | 8.91 | 5.14 |
| 6-10 | 5.56 | 3.22 | 4.2 | 1.36 | 2.97 | 2.07 | 3.03 | 2.9 | 7.64 | 3.66 |
| 6-11 | 68.81 | 65.13 | 64.79 | 64.41 | 57.47 | 63.55 | 64.79 | 60.5 | 61.13 | 64.29 |
| 6-12 | 68.38 | 63.74 | 45 | 34.86 | 35.79 | 25.68 | 31.84 | 25.18 | 33.91 | 40.48 |
| 7-1 | 63.71 | 61.07 | 60.24 | 55.62 | 56.07 | 57.86 | 45.3 | 48.45 | 48.89 | 55.25 |
| 7-2 | 49.63 | 41.8 | 31.28 | 30.46 | 23.63 | 26.56 | 15.68 | 23.23 | 24.1 | 29.60 |
| 7-3 | 61.72 | 60.08 | 60.77 | 60.47 | 50.53 | 60.58 | 58.07 | 57.15 | 55.66 | 59.36 |
| 7-4 | 83.11 | 82.56 | 77.6 | 81.19 | 57.36 | 56.23 | 74.45 | 56.05 | 69.23 | 71.98 |
| Mean | 48.3210 | 45.7690 | 44.1055 | 40.9619 | 40.7781 | 38.6957 | 38.3476 | 35.9871 | 38.2268 | |
| N/M | 0.17807 | 0.10524 | 0.07880 | 0.07985 | 0.07944 | 0.06458 | 0.06673 | 0.07527 | 0.08104 | |

FIG. 2C

| BMP3 | | | | | | |
|---|---|---|---|---|---|---|
| CpG | 34 | 53 | 61 | 70 | 74 | |
| NORMAL | | | | | | Mean |
| 8-4 | 3.25 | 3.26 | 2.83 | 3.22 | 2.82 | 3.08 |
| 8-5 | 1.37 | 2.3 | 1.4 | 1.88 | 2.23 | 2.03 |
| 8-6 | 3.18 | 1.59 | 2.69 | 2.09 | 2.37 | 2.38 |
| 8-7 | 3.78 | 4.15 | 0.88 | 2.35 | 1.84 | 2.59 |
| 8-8 | 3.99 | 2.96 | 2.3 | 2.31 | 4.26 | 3.40 |
| 8-9 | 5.49 | 3.69 | 1.71 | 3.03 | 3.65 | 3.51 |
| 8-10 | 5.29 | 3.44 | 0.02 | 0.06 | 0.11 | 1.78 |
| 8-11 | 4.22 | 2.92 | 2.82 | 2.65 | 2.51 | 3.02 |
| 8-12 | 2.98 | 3.23 | 2.71 | 1.84 | 1.98 | 2.51 |
| Mean | 3.63889 | 3.09889 | 1.96889 | 2.16333 | 2.42778 | 2.70 |
| | | | | | SD all | 1.18 |
| | | | | | M+2SD | 5.05 |
| | | | | | M+3SD | 6.23 |

| CpG | 34 | 53 | 61 | 70 | 74 | |
|---|---|---|---|---|---|---|
| ADENOMA | | | | | | Mean |
| 3-4 | 2.33 | 3.14 | 3.61 | 2.69 | 4.13 | 3.18 |
| 3-5 | 19.45 | 8 | 4 | 2.88 | 4.25 | 7.72 |
| 3-6 | 17.33 | 14.18 | 13.48 | 15.42 | 17.18 | 15.51 |
| 3-7 | 46.19 | 46.07 | 41.96 | 41.15 | 41.66 | 43.21 |
| 3-8 | 9.43 | 4.4 | 3.57 | 6.31 | 6.61 | 6.06 |
| 3-9 | 5.04 | 4.76 | 3.42 | 3.29 | 3.1 | 3.92 |
| 3-10 | 5.32 | 4.03 | 3.39 | 2.71 | 1.73 | 3.43 |
| 3-11 | 4.77 | 3.54 | 3.99 | 11.56 | 3.79 | 5.53 |
| 3-12 | 5.63 | 3.77 | 4.42 | 6.87 | 5.14 | 5.17 |
| 5-1 | 87.27 | 85.28 | 84.86 | 83.63 | 86.85 | 85.58 |
| 5-2 | 34.35 | 32.92 | 25.52 | 31.5 | 28.84 | 30.62 |
| 5-4 | 8.5 | 2.83 | 2.75 | 4.72 | 3.95 | 4.55 |
| 5-11 | 30.56 | 23.84 | 15.75 | 20.94 | 18.2 | 21.86 |
| 5-12 | 9.12 | 15.55 | 12.11 | 23.91 | 10.78 | 14.29 |
| 6-1 | 90.01 | 88.79 | 88.48 | 88.35 | 88.02 | 88.53 |
| 6-2 | 3.32 | 3.38 | 3.03 | 2.23 | 3.28 | 3.03 |
| 6-3 | 82.39 | 80.24 | 80.21 | 79.47 | 80.87 | 80.64 |
| 6-4 | 2.98 | 2.51 | 2.52 | 2.34 | 3.17 | 2.79 |
| 6-5 | 2.8 | 2.51 | 2.02 | 2.46 | 2.61 | 2.48 |
| 6-6 | 26.76 | 25.01 | 23.53 | 24.17 | 24.84 | 24.86 |
| 7-5 | 41.72 | 40.49 | 40.46 | 39.64 | 40.58 | 40.58 |
| 7-6 | 72.74 | 70.9 | 66.24 | 68.78 | 70.47 | 69.83 |
| 7-7 | 14.78 | 14.42 | 13.32 | 13 | 12.37 | 13.58 |
| 7-8 | 13.74 | 15.98 | 11.73 | 6.85 | 6.02 | 11.86 |
| 7-9 | 20.44 | 21.31 | 20.56 | 19.66 | 20.77 | 20.55 |
| 7-10 | 16.24 | 13.64 | 12.34 | 16.49 | 13.28 | 14.25 |
| 7-11 | 5.40 | 3.8 | 3.88 | 6.34 | 3.31 | 5.08 |
| 7-12 | 27.12 | 27.51 | 27.26 | 26.17 | 26.11 | 26.83 |
| 8-1 | 56.1 | 55.54 | 55.85 | 56.41 | 55.4 | 55.86 |
| 8-2 | 82.63 | 81.89 | 81.36 | 82.11 | 80.68 | 81.73 |
| 8-3 | 1.36 | 2.08 | 0.67 | 2.7 | 2.4 | 1.84 |
| Mean | 27.4126 | 25.8742 | 24.7184 | 25.7726 | 24.9142 | |
| N/M | 0.14004 | 0.11832 | 0.07965 | 0.08549 | 0.09745 | |

FIG. 2D

| BMP3 | | | | | | |
|---|---|---|---|---|---|---|
| CpG | 34 | 53 | 61 | 70 | 74 | |
| CANCER | | | | | | Mean |
| 1-1 | 4.1 | 3.27 | 2.75 | 2.48 | 2.97 | 3.11 |
| 1-2 | 2.53 | 2.36 | 1.79 | 1.69 | 1.79 | 2.03 |
| 1-3 | 3.93 | 2.97 | 2.67 | 2.33 | 3.2 | 3.02 |
| 1-4 | 3.03 | 5.87 | 6.21 | 6.31 | 6.13 | 5.51 |
| 1-5 | 84.92 | 84.93 | 84.66 | 84.32 | 84.83 | 84.69 |
| 1-6 | 69.86 | 68.53 | 68.6 | 68.14 | 69.27 | 68.88 |
| 1-7 | 4.13 | 3.89 | 2.73 | 3.84 | 3.19 | 3.35 |
| 1-8 | 3.57 | 2.38 | 3 | 1.77 | 2.7 | 2.68 |
| 1-9 | 46.41 | 30.05 | 14.12 | 5.5 | 5.8 | 20.30 |
| 1-10 | 45.95 | 28.29 | 12.83 | 4.28 | 3.9 | 19.05 |
| 1-11 | 3.71 | 6.67 | 4.29 | 4.83 | 16.81 | 7.38 |
| 1-12 | 3.68 | 3.03 | 2.44 | 2.2 | 2.58 | 2.79 |
| 2-1 | 2.8 | 2.42 | 1.17 | 1.05 | 1.37 | 1.96 |
| 2-2 | 3.54 | 2.31 | 3.53 | 1.19 | 2.97 | 2.51 |
| 2-3 | 47.85 | 47.99 | 46.97 | 46.63 | 46.65 | 47.22 |
| 2-4 | 21.33 | 4.65 | 3.75 | 2.82 | 3.23 | 7.18 |
| 2-5 | 74.6 | 74.29 | 73.31 | 74.06 | 74.61 | 74.17 |
| 2-6 | 43.55 | 43.4 | 42.73 | 43.3 | 42.68 | 42.91 |
| 2-7 | 57.93 | 57.12 | 56.09 | 56.29 | 56.34 | 56.75 |
| 2-8 | 20.14 | 6 | 3.12 | 4.79 | 4.2 | 7.65 |
| 2-9 | 84.2 | 83.37 | 82.82 | 82.49 | 83.03 | 83.18 |
| 2-10 | 83.9 | 82.79 | 82.46 | 82.14 | 82.69 | 82.80 |
| 2-11 | 66.48 | 37.64 | 33.91 | 33.96 | 33.87 | 41.54 |
| 2-12 | 4.59 | 2.96 | 2.4 | 2.63 | 3.37 | 3.19 |
| 3-2 | 52.88 | 52.38 | 52.39 | 52.08 | 52.32 | 52.41 |
| 3-3 | 27.71 | 31.07 | 35.97 | 27.23 | 21.08 | 26.61 |
| 3-5 | 21.21 | 17.24 | 17 | 13.13 | 13.88 | 16.58 |
| 3-6 | 4.02 | 2.82 | 2.58 | 1.47 | 2.25 | 2.63 |
| 3-7 | 3.07 | 5.48 | 5.09 | 3.07 | 2.83 | 3.87 |
| 3-8 | 37.96 | 36.21 | 34.38 | 35.91 | 36.51 | 36.19 |
| 3-9 | 9.87 | 9.23 | 3.47 | 5.98 | 4.83 | 6.67 |
| 3-10 | 8.33 | 8.55 | 3.47 | 4.44 | 4.43 | 5.85 |
| 6-7 | 87.32 | 85.77 | 86.05 | 85.91 | 86.14 | 86.24 |
| 6-8 | 48.14 | 52.49 | 48.07 | 49.81 | 48.67 | 49.40 |
| 6-9 | 3.81 | 2.96 | 3.49 | 1.99 | 2.75 | 2.80 |
| 6-10 | 3.32 | 2.1 | 1.86 | 1.46 | 3.68 | 2.35 |
| 6-11 | 36.92 | 55.67 | 54.4 | 54.85 | 33.99 | 51.17 |
| 6-12 | 15.79 | 14.37 | 13.98 | 13.37 | 14.73 | 14.45 |
| 7-1 | 2.37 | 2.63 | 2.21 | 3.07 | 3.63 | 2.38 |
| 7-2 | 3.5 | 2.31 | 3.04 | 3.34 | 3.77 | 3.17 |
| 7-3 | 64.11 | 63.08 | 63.22 | 62.45 | 63.17 | 63.21 |
| 7-4 | 4.82 | 2.5 | 3.03 | 2.53 | 2.49 | 3.07 |
| Mean | 28.9381 | 27.4650 | 25.9548 | 25.3643 | 25.8881 | |
| N/M | 0.13266 | 0.11137 | 0.07586 | 0.08667 | 0.09378 | |

FIG. 2E

| | Septin9 | | | | | | |
|---|---|---|---|---|---|---|---|
| CpG | 31 | 38 | 59 | 61 | 68 | 70 | |
| NORMAL | | | | | | | Mean |
| 8-4 | 4.33 | 4.68 | 3.65 | 3.4 | 3.05 | 2.55 | 3.61 |
| 8-5 | 5.81 | 5.22 | 3.88 | 2.55 | 2.56 | 2.62 | 3.77 |
| 8-6 | 9.7 | 8.48 | 6.03 | 5.02 | 5.4 | 3.5 | 6.36 |
| 8-7 | 25.07 | 23.83 | 15.73 | 15.38 | 12.7 | 7.3 | 16.67 |
| 8-8 | 9.6 | 9.34 | 7.97 | 7.68 | 7.86 | 5.31 | 7.88 |
| 8-9 | 2.93 | 3.79 | 2.85 | 2.19 | 2.67 | 3 | 2.74 |
| 8-10 | 2.95 | 3.94 | 2.22 | 3.17 | 3.03 | 3.33 | 2.94 |
| 8-11 | 9.91 | 10.36 | 7.98 | 6.95 | 6.22 | 4.78 | 7.70 |
| 8-12 | 7.37 | 8.04 | 5.18 | 3.9 | 3.49 | 3.71 | 5.28 |
| Mean | 8.63000 | 8.63111 | 6.06556 | 5.58222 | 5.13111 | 3.78888 | 6.30 |
| | | | | | SD all | | 5.06 |
| | | | | | M+2SD | | 16.42 |
| | | | | | M+3SD | | 21.47 |
| CpG | 31 | 38 | 59 | 61 | 68 | 70 | |
| ADENOMA | | | | | | | Mean |
| 3-4 | 71.21 | 71.25 | 67.4 | 67.63 | 70.36 | 70.48 | 69.72 |
| 3-5 | 78.85 | 78.63 | 78.74 | 79.41 | 78.89 | 77.51 | 78.64 |
| 3-6 | 47.45 | 47.25 | 47.36 | 46.33 | 45.52 | 43.7 | 46.27 |
| 3-7 | 54.28 | 54.19 | 53.89 | 54.5 | 52.93 | 51.27 | 53.51 |
| 3-8 | 82.73 | 80.42 | 82.52 | 83.81 | 81.98 | 83.04 | 82.42 |
| 3-9 | 59.76 | 59.11 | 59.97 | 59.88 | 59.03 | 59.65 | 59.57 |
| 3-10 | 59.64 | 59.13 | 60.14 | 60.14 | 59.08 | 59.62 | 59.63 |
| 3-11 | 81.43 | 80.79 | 81.85 | 82.38 | 81.68 | 81.7 | 81.64 |
| 3-12 | 87.2 | 87.14 | 87.76 | 85.18 | 87.49 | 86.78 | 86.93 |
| 5-1 | 81.86 | 81.66 | 82.4 | 81.83 | 81.39 | 82.63 | 81.96 |
| 5-3 | 58.22 | 58.48 | 57.93 | 56.61 | 55.53 | 52.77 | 56.59 |
| 5-4 | 90.56 | 89.44 | 91.06 | 90.37 | 89.35 | 89.37 | 90.02 |
| 5-11 | 82.52 | 81.57 | 82.17 | 82.04 | 80.93 | 80.54 | 81.63 |
| 5-13 | 87.76 | 87.67 | 88.6 | 87.5 | 87.52 | 83.04 | 87.02 |
| 6-1 | 88.48 | 88.58 | 88.91 | 88.89 | 88.14 | 87.98 | 88.50 |
| 6-2 | 54.02 | 53.55 | 52.96 | 51.62 | 51.85 | 49.39 | 52.23 |
| 6-3 | 75.28 | 74.77 | 75.14 | 74.75 | 73.85 | 70.73 | 74.09 |
| 6-4 | 68.87 | 67.68 | 66.53 | 65.84 | 46.88 | 43.19 | 57.83 |
| 6-5 | 39.3 | 39.97 | 39.71 | 39.79 | 24.9 | 18.71 | 33.38 |
| 6-6 | 46.53 | 46.87 | 47.66 | 46.89 | 46.41 | 43.43 | 46.26 |
| 7-5 | 71.84 | 71.15 | 71.81 | 71.76 | 71.65 | 70.46 | 71.45 |
| 7-6 | 67.38 | 67.19 | 66.38 | 67.37 | 67.74 | 65.9 | 66.99 |
| 7-7 | 39.96 | 39.74 | 40.16 | 38.96 | 38.06 | 35.38 | 38.71 |
| 7-8 | 76.27 | 73.19 | 78.33 | 77.87 | 70.89 | 65.35 | 73.98 |
| 7-9 | 82.36 | 81.58 | 82.87 | 80.95 | 81.01 | 79.39 | 81.36 |
| 7-10 | 82.1 | 81.35 | 83.93 | 81.40 | 80.71 | 78.28 | 81.33 |
| 7-11 | 79.96 | 79.14 | 76.53 | 75.27 | 74.83 | 63.99 | 74.97 |
| 7-12 | 28.03 | 27.75 | 28.58 | 28.03 | 27.64 | 27.52 | 27.93 |
| 8-1 | 47.19 | 46.29 | 48.75 | 47.99 | 47.07 | 47.31 | 47.43 |
| 8-2 | 78.05 | 78.32 | 78.79 | 79.03 | 77.53 | 78.26 | 78.33 |
| 8-3 | 73.6 | 73.1 | 73.21 | 73.63 | 72.92 | 73.09 | 73.26 |
| Mean | 68.4058 | 67.9658 | 68.1006 | 67.3352 | 66.2506 | 64.2410 | 67.0498 |
| N/M | 0.12616 | 0.12699 | 0.08907 | 0.08390 | 0.07745 | 0.05898 | 0.09403 |

FIG. 2F

| CpG | Septin9 | | | | | | |
|---|---|---|---|---|---|---|---|
| | 31 | 38 | 59 | 61 | 68 | 70 | |
| CANCER | | | | | | | Mean |
| 1-1 | 74.24 | 74.37 | 74.74 | 59.16 | 73.67 | 69.78 | 72.66 |
| 1-2 | 64.3 | 63.59 | 64.48 | 63.97 | 64.03 | 64.55 | 64.15 |
| 1-3 | 78.49 | 77.13 | 77.94 | 75.03 | 76.7 | 75.33 | 76.77 |
| 1-4 | 76.88 | 76.83 | 61.04 | 77.26 | 77.25 | 76.34 | 74.27 |
| 1-5 | 83.22 | 82.77 | 82.93 | 83.1 | 78.22 | 81.8 | 82.00 |
| 1-6 | 72.72 | 72.6 | 73.26 | 73.34 | 72.93 | 72.93 | 72.85 |
| 1-7 | 58.64 | 58.8 | 59.5 | 59.02 | 57.95 | 58.03 | 58.66 |
| 1-8 | 41.04 | 41.59 | 42.34 | 39.9 | 39.31 | 31.59 | 39.30 |
| 1-9 | 87.69 | 87.79 | 87.9 | 85.22 | 87.34 | 86.76 | 87.12 |
| 1-10 | 87.52 | 88.04 | 88.3 | 85.78 | 87.66 | 87.37 | 87.45 |
| 1-11 | 93.45 | 93.07 | 83.34 | 32.83 | 92.33 | 92.82 | 81.25 |
| 1-12 | 54.85 | 51.7 | 55.46 | 53.56 | 51.61 | 48.38 | 52.59 |
| 2-1 | 59.5 | 59.97 | 61.38 | 60.56 | 58.77 | 59.98 | 59.49 |
| 2-2 | 52.9 | 57.7 | 53.1 | 57.04 | 57.76 | 46.02 | 54.09 |
| 2-3 | 49.88 | 49.48 | 50.03 | 50.05 | 48.86 | 49.33 | 49.61 |
| 2-4 | 45.75 | 46.15 | 46.94 | 47 | 46.06 | 29.88 | 43.65 |
| 2-5 | 65.13 | 65.64 | 67.05 | 57.26 | 66.23 | 66.47 | 66.30 |
| 2-6 | 20.94 | 20.61 | 20.35 | 19.83 | 20.44 | 9.66 | 18.62 |
| 2-7 | 47.93 | 46.04 | 43.52 | 41.4 | 36.64 | 39.59 | 42.19 |
| 2-8 | 68.51 | 68.14 | 69.55 | 59.26 | 68.13 | 68.64 | 68.71 |
| 2-9 | 75.03 | 73.17 | 56.65 | 75.26 | 71.97 | 75.37 | 71.20 |
| 2-10 | 74.22 | 72.34 | 56.32 | 74.72 | 71 | 74.53 | 70.51 |
| 2-11 | 37.38 | 36.83 | 24.02 | 14.56 | 10.66 | 3.93 | 21.56 |
| 2-12 | 58.19 | 58.71 | 59.1 | 58.62 | 55.6 | 54.68 | 57.65 |
| 3-1 | 46.5 | 46.36 | 47.19 | 48.3 | 45.85 | 45.97 | 46.70 |
| 3-3 | 47.82 | 48.26 | 49.38 | 48.05 | 48.32 | 48.3 | 48.36 |
| 3-5 | 30.03 | 28.6 | 30.72 | 27.46 | 28.69 | 29.34 | 29.14 |
| 3-6 | 64.74 | 65.65 | 65.21 | 60.89 | 64.87 | 65.19 | 64.43 |
| 3-7 | 57.61 | 58.27 | 59.96 | 58.38 | 58.15 | 54.58 | 57.83 |
| 3-8 | 30.81 | 30.44 | 32.62 | 31.11 | 31.38 | 31.13 | 31.25 |
| 3-9 | 57.09 | 57.89 | 58.38 | 57.84 | 56.82 | 57.5 | 57.52 |
| 3-10 | 56.43 | 56.72 | 58.5 | 57.37 | 56.35 | 56.66 | 56.99 |
| 6-7 | 86.96 | 86.4 | 81.86 | 86.91 | 86.55 | 84.06 | 85.46 |
| 6-8 | 61.93 | 60.83 | 61.43 | 62.11 | 62.02 | 62.04 | 61.73 |
| 6-9 | 55.17 | 54.87 | 55.62 | 55.64 | 55.6 | 55.37 | 55.38 |
| 6-10 | 54.31 | 54.02 | 54.91 | 54.51 | 54.35 | 54.33 | 54.41 |
| 6-11 | 2.04 | 2.13 | 3.89 | 3.2 | 2.29 | 2.48 | 2.67 |
| 6-12 | 75.22 | 75.08 | 76.44 | 76.09 | 75.94 | 76.3 | 75.85 |
| 7-1 | 61.33 | 63.35 | 63.77 | 63.97 | 62.75 | 59.07 | 62.71 |
| 7-2 | 63.88 | 62.96 | 64.86 | 63.63 | 63.36 | 62.23 | 63.49 |
| 7-3 | 73.04 | 73.08 | 73.78 | 74.34 | 73.65 | 73.43 | 73.54 |
| 7-4 | 75.73 | 77.28 | 78.63 | 79.06 | 79.33 | 79.13 | 77.84 |
| | | | | | | | |
| Mean | 60.3864 | 60.1548 | 58.8624 | 59.5824 | 58.9786 | 57.4593 | |
| S/M | 0.14315 | 0.14848 | 0.16895 | 0.09369 | 0.08720 | 0.08584 | |

FIG. 2G

| TFPI2 | | | | | | | | | | |
|---|---|---|---|---|---|---|---|---|---|---|
| CpG | 28 | 33 | 41 | 50 | 55 | 59 | 63 | 67 | 74 | |
| NORMAL | | | | | | | | | | Mean |
| 3-4 | 16.8 | 11.72 | 18.34 | 15.92 | 14.43 | 12.65 | 20.44 | 11.46 | 10.88 | 14.74 |
| 3-5 | 10.4 | 6.72 | 10.5 | 9.92 | 8.66 | 8.57 | 14.89 | 7.26 | 6.75 | 9.27 |
| 3-6 | 5.78 | 3.74 | 5.31 | 5.57 | 4.66 | 5.04 | 7.18 | 2.99 | 4.17 | 4.93 |
| 3-7 | 7.42 | 3.99 | 6.42 | 6.28 | 5.39 | 4.82 | 8.15 | 3.56 | 3.07 | 5.44 |
| 3-8 | 5.13 | 2.55 | 3.84 | 3.46 | 3.28 | 2.89 | 5.08 | 2.4 | 2.54 | 3.45 |
| 3-9 | 9.18 | 6.49 | 10.3 | 7.08 | 6.96 | 6.93 | 11.26 | 4.29 | 4.51 | 7.44 |
| 3-10 | 9.2 | 5.94 | 10.48 | 7.21 | 6.49 | 6.71 | 11.22 | 4.83 | 4.22 | 7.37 |
| 3-11 | 8.32 | 3.01 | 5.89 | 6.61 | 3.66 | 4.03 | 6.71 | 3.87 | 3.97 | 4.91 |
| 3-12 | 5.23 | 3.81 | 5.83 | 4.98 | 3.17 | 2.36 | 7.42 | 3.79 | 3.28 | 4.38 |
| Mean | 8.61333 | 5.44111 | 8.51222 | 7.44222 | 6.17778 | 6.04444 | 10.29778 | 4.84444 | 4.61111 | 6.88 |
| | | | | | | | | | SD all | 3.86 |
| | | | | | | | | | M+2SD | 14.61 |
| | | | | | | | | | M+3SD | 18.47 |
| CpG | 28 | 33 | 41 | 50 | 55 | 59 | 63 | 67 | 74 | |
| ADENOMA | | | | | | | | | | Mean |
| 3-4 | 66.66 | 49.94 | 65.74 | 66.29 | 59.94 | 62.71 | 64.28 | 48.29 | 30.33 | 57.13 |
| 3-5 | 77.23 | 76.12 | 77.55 | 76.98 | 75.65 | 73.83 | 76.39 | 72.7 | 71 | 75.27 |
| 3-6 | 41.89 | 36.35 | 40.76 | 40.97 | 40.56 | 38.13 | 40.11 | 37.77 | 34.48 | 39.00 |
| 3-7 | 53.43 | 48.78 | 52.34 | 53.57 | 50.43 | 48.98 | 53.74 | 47.83 | 44.76 | 50.37 |
| 3-8 | 80.17 | 78.31 | 79.2 | 79.83 | 78.76 | 77.18 | 76.28 | 78.09 | 68.06 | 77.30 |
| 3-9 | 41.24 | 38.22 | 40.04 | 40.87 | 40.69 | 40.06 | 39.84 | 39.33 | 39.04 | 40.03 |
| 3-10 | 39.75 | 37.16 | 38.59 | 39.38 | 39.06 | 38.63 | 38.26 | 37.68 | 36.9 | 38.38 |
| 3-11 | 84.09 | 81.71 | 83.36 | 83.58 | 83.66 | 82.34 | 81.57 | 82.53 | 80.87 | 82.63 |
| 3-12 | 86.28 | 78.8 | 86.62 | 87.69 | 78.28 | 79.03 | 86.50 | 79.89 | 58.94 | 79.30 |
| 5-1 | 78.42 | 77.48 | 78.38 | 73.72 | 77.69 | 76.86 | 73.05 | 73.7 | 79.17 | 75.61 |
| 5-2 | 58.47 | 53.62 | 57.42 | 53.97 | 55.91 | 55.91 | 54.51 | 52.46 | 50.29 | 54.84 |
| 5-4 | 91.15 | 91.11 | 92.36 | 87.49 | 91.88 | 86.98 | 90 | 90.22 | 89.08 | 89.53 |
| 5-11 | 73.27 | 70.21 | 70.36 | 68.17 | 68.56 | 68.83 | 66.23 | 68.63 | 68.41 | 69.52 |
| 5-12 | 78.05 | 75.39 | 88.77 | 80.16 | 80.93 | 83.95 | 78.32 | 83.67 | 83.53 | 80.95 |
| 6-1 | 86.33 | 84.43 | 85.44 | 85.9 | 85.74 | 83.62 | 83.43 | 84.01 | 82.29 | 84.55 |
| 6-2 | 52.6 | 48.51 | 50.23 | 51.37 | 50.91 | 48.11 | 50.78 | 48.74 | 47.62 | 49.87 |
| 6-3 | 71.67 | 68.75 | 70.6 | 70.08 | 70.4 | 67.48 | 68.53 | 67.59 | 64.93 | 69.00 |
| 6-4 | 53.89 | 37.64 | 52.8 | 53.96 | 47.65 | 39 | 48.93 | 48.03 | 39.87 | 46.61 |
| 6-5 | 18.96 | 10.51 | 19.35 | 14.33 | 13.37 | 13.03 | 19.15 | 7.52 | 6.76 | 13.55 |
| 6-6 | 52.19 | 48.46 | 50.11 | 50.18 | 50.08 | 47.91 | 48.4 | 47.35 | 40.79 | 48.40 |
| 7-5 | 57.72 | 56.03 | 57.33 | 57.64 | 57.01 | 55.73 | 56.61 | 55.51 | 53.79 | 56.40 |
| 7-6 | 52.68 | 49.32 | 51 | 50.35 | 50.47 | 48.55 | 48.43 | 49.85 | 49.02 | 50.01 |
| 7-7 | 25.22 | 18.23 | 21.12 | 20.96 | 19.79 | 18.46 | 22.15 | 16.57 | 15.59 | 19.79 |
| 7-8 | 33.85 | 35.37 | 23.72 | 38.92 | 27.03 | 37.43 | 54.82 | 30.88 | 33.68 | 30.74 |
| 7-9 | 73.9 | 59.02 | 70.98 | 65.87 | 66.99 | 63.86 | 73.3 | 62.11 | 56.11 | 65.33 |
| 7-10 | 73.51 | 56.26 | 68.66 | 63.4 | 64.27 | 58.32 | 65.99 | 60.46 | 55.45 | 63.10 |
| 7-11 | 63.86 | 52.8 | 58.02 | 62.29 | 55.02 | 53.49 | 67.1 | 48.71 | 39.43 | 56.71 |
| 7-12 | 26.3 | 21.82 | 25.75 | 26.12 | 26.73 | 24.49 | 27.01 | 23.98 | 22.07 | 24.87 |
| 8-1 | 39.67 | 36.04 | 38.87 | 39.82 | 38.12 | 37.04 | 39.47 | 36.65 | 35.48 | 38.01 |
| 8-2 | 4.39 | 2.77 | 3.48 | 8.4 | 3.36 | 4.15 | 5.28 | 5.01 | 4.23 | 4.67 |
| 8-3 | 18.38 | 6.67 | 9.77 | 8.39 | 7.12 | 8.69 | 23.38 | 3.59 | 7.33 | 9.52 |
| Mean | 56.5688 | 50.1781 | 55.1155 | 54.2635 | 53.4752 | 51.9326 | 55.4897 | 51.3326 | 47.6661 | |
| N/M | 0.15326 | 0.10844 | 0.15444 | 0.13715 | 0.11553 | 0.11639 | 0.18467 | 0.09437 | 0.09674 | |

FIG. 2H

| CpG | TFPI2 28 | 33 | 41 | 50 | 58 | 59 | 63 | 67 | 74 | |
|---|---|---|---|---|---|---|---|---|---|---|
| CANCER | | | | | | | | | | Mean |
| 1-1 | 75.32 | 73.75 | 76.91 | 76.38 | 76.88 | 75.12 | 74.58 | 75.44 | 71.99 | 75.29 |
| 1-2 | 60.7 | 58.48 | 59.83 | 60.11 | 59.24 | 58.56 | 58.47 | 58.39 | 58.02 | 59.09 |
| 1-3 | 69.4 | 67.39 | 69.05 | 68.3 | 69.58 | 68.17 | 67.34 | 67.9 | 66.82 | 68.12 |
| 1-4 | 88.99 | 83.51 | 85.32 | 85.75 | 83.16 | 80.99 | 83.51 | 54.26 | 56.55 | 77.48 |
| 1-5 | 80.34 | 78.4 | 79.88 | 77.16 | 79.53 | 78.17 | 78.3 | 73.3 | 76.21 | 77.97 |
| 1-6 | 73.82 | 70.18 | 72.1 | 72.38 | 73.46 | 71.88 | 70.86 | 69.43 | 69.23 | 71.18 |
| 1-7 | 56.49 | 13.25 | 31.78 | 55.62 | 33.26 | 30.17 | 54.09 | 28.21 | 32.74 | 37.29 |
| 1-8 | 32.13 | 28.84 | 30.98 | 33.88 | 33.26 | 30.28 | 30.66 | 29.42 | 28.77 | 30.92 |
| 1-9 | 89.55 | 86.99 | 88.73 | 89.13 | 88.26 | 87.47 | 86.82 | 87.1 | 83.93 | 84.60 |
| 1-10 | 88.63 | 86.03 | 88.65 | 88.27 | 87.98 | 86.9 | 86.05 | 86.28 | 85.33 | 83.78 |
| 1-11 | 70.4 | 12.47 | 93.04 | 93.81 | 75.62 | 91.84 | 90.3 | 64.22 | 18.67 | 67.88 |
| 1-12 | 67 | 65.56 | 66.77 | 66.96 | 66.98 | 65.79 | 64.81 | 64.2 | 64.96 | 65.89 |
| 2-1 | 15.11 | 11.81 | 17.67 | 13.17 | 13.98 | 13.98 | 17.78 | 13.83 | 11.68 | 12.79 |
| 2-2 | 38.93 | 6.35 | 10.73 | 33.33 | 17.12 | 15.95 | 30.68 | 8.02 | 7.15 | 17.58 |
| 2-3 | 45.41 | 43.39 | 44.33 | 44.06 | 44.47 | 43.25 | 43.52 | 43.4 | 42.42 | 43.69 |
| 2-4 | 45.2 | 42.77 | 44.85 | 45.04 | 45.13 | 43.42 | 43.83 | 41.69 | 35.59 | 43.06 |
| 2-5 | 63.22 | 61.49 | 65.06 | 65.35 | 65.29 | 63.52 | 63.19 | 62.23 | 52.05 | 61.27 |
| 2-6 | 31.88 | 28.87 | 29.77 | 30.31 | 30.84 | 29.71 | 29.63 | 28.87 | 39.19 | 29.86 |
| 2-7 | 45.62 | 43.81 | 44.36 | 44.25 | 41.67 | 43.54 | 43.71 | 42.12 | 41.39 | 43.39 |
| 2-8 | 64.7 | 62.61 | 63.61 | 63.79 | 57.58 | 60.94 | 60.93 | 62.33 | 58.59 | 61.66 |
| 2-9 | 75.87 | 71.86 | 75.47 | 74.9 | 75.49 | 71.88 | 71.42 | 74.03 | 73.19 | 73.77 |
| 2-10 | 72.47 | 68.98 | 72.08 | 71.33 | 72.4 | 68.8 | 67.93 | 70.49 | 69.81 | 70.48 |
| 2-11 | 39.41 | 30.05 | 64.37 | 64.23 | 56.2 | 38.22 | 80.85 | 38.34 | 39.96 | 38.83 |
| 2-12 | 50.9 | 46.83 | 56.05 | 55.83 | 52.73 | 51.96 | 54.45 | 52.23 | 48.45 | 52.05 |
| 3-2 | 43.65 | 40.73 | 43.07 | 42.99 | 42.94 | 43.01 | 42.86 | 40.78 | 40.71 | 42.30 |
| 3-3 | 38.56 | 30.45 | 43.56 | 40.53 | 35.54 | 34.59 | 40.19 | 36.63 | 28.63 | 36.41 |
| 3-5 | 61.12 | 56.83 | 57.86 | 54.72 | 56.43 | 56.68 | 54.83 | 50.83 | 54.88 | 56.02 |
| 3-6 | 33.8 | 48.22 | 58.5 | 38.46 | 17.73 | 19.02 | 29.45 | 18.28 | 13.88 | 33.04 |
| 3-7 | 63.5 | 60.54 | 61.53 | 58.59 | 62.75 | 60.84 | 58.35 | 58.15 | 58.39 | 60.34 |
| 3-8 | 22.3 | 38.7 | 19.36 | 18.14 | 20.25 | 18.98 | 19.06 | 19.85 | 19.06 | 19.52 |
| 3-9 | 53.64 | 51.06 | 52.01 | 48.3 | 50.75 | 48.66 | 47.16 | 46.77 | 49.25 | 49.73 |
| 3-10 | 49.62 | 48.7 | 48.35 | 46.3 | 48.18 | 47.48 | 46.33 | 44.56 | 46.78 | 47.34 |
| 6-7 | 84.66 | 83.96 | 84.44 | 83.37 | 84.53 | 79.72 | 81.88 | 82.3 | 81.37 | 82.97 |
| 6-8 | 52.41 | 48.13 | 51.33 | 50.98 | 50.21 | 49.08 | 50.3 | 45.18 | 39.78 | 48.26 |
| 6-9 | 34.12 | 12.99 | 37.31 | 25.11 | 14.81 | 25.66 | 37.63 | 14.79 | 31.82 | 36.03 |
| 6-10 | 34.11 | 12.43 | 36.31 | 23.71 | 13.2 | 34.85 | 37.09 | 14.15 | 31.6 | 25.27 |
| 6-11 | 61.62 | 30.74 | 60.7 | 61.09 | 59.77 | 59.31 | 58.74 | 58.47 | 56.63 | 56.67 |
| 6-12 | 57.77 | 42.67 | 65.73 | 64.03 | 62.80 | 63.07 | 64.1 | 61.68 | 49.37 | 58.01 |
| 7-1 | 62.23 | 60.07 | 61.28 | 61.27 | 62.01 | 57.94 | 59.85 | 60.22 | 59.01 | 60.39 |
| 7-2 | 38.32 | 38.87 | 41.16 | 40.3 | 38.66 | 33.41 | 33.09 | 37.17 | 35.3 | 37.72 |
| 7-3 | 55.38 | 53.42 | 58.54 | 54.8 | 54.68 | 53.01 | 53.42 | 53.37 | 51.98 | 53.88 |
| 7-4 | 76.53 | 56.91 | 76.83 | 76.78 | 57.28 | 71.59 | 73.29 | 65.43 | 54.48 | 67.69 |
| Mean | 56.8910 | 48.4098 | 56.4660 | 56.2258 | 53.1431 | 53.1910 | 55.3610 | 50.5743 | 47.1645 | |
| Rs/M | 0.15140 | 0.11240 | 0.15075 | 0.15237 | 0.11825 | 0.11804 | 0.18528 | 0.09579 | 0.08777 | |

FIG. 2I

| CpG | 27 | 29 | 31 | 34 | 37 | 44 | 46 | 55 | 65 | 74 | |
|---|---|---|---|---|---|---|---|---|---|---|---|
| NORMAL | | | | | | | | | | | Mean |
| 8-4 | 7.95 | 3.92 | 5.81 | 15.44 | 11.76 | 10 | 11.72 | 14.57 | 6.23 | 6.67 | 9.41 |
| 8-5 | 0.52 | 0.73 | 5.76 | 3.59 | 0.33 | 2.36 | 3.48 | 0.41 | 2.95 | 0.38 | 2.04 |
| 8-6 | 2.46 | 2.56 | 3.78 | 2.51 | 2.84 | 0.1 | 7.27 | 3.88 | 2.38 | 2.18 | 2.40 |
| 8-7 | 27.16 | 27.13 | 7.42 | 26.64 | 26.88 | 4 | 4.06 | 10.23 | 23.1 | 15.77 | 18.20 |
| 8-8 | 3.46 | 6.35 | 6.63 | 5.31 | 5.56 | 6.13 | 5.73 | 4.37 | 4.31 | 10.11 | 5.58 |
| 8-9 | 1.55 | 1.81 | 0.51 | 1.55 | 1.55 | 0.23 | 0.26 | 1.66 | 6.07 | 8.5 | 2.37 |
| 8-10 | 0.16 | 0.7 | 0.37 | 0.2 | 0.38 | 0.17 | 0.42 | 0.16 | 1.71 | 7.13 | 1.13 |
| 8-11 | 14.46 | 9.34 | 8.79 | 11.49 | 11.46 | 8.65 | 3.08 | 8.6 | 2.32 | 10.83 | 8.90 |
| 8-12 | 3.31 | 3.92 | 2.34 | 8.86 | 2.8 | 4.66 | 2.22 | 9.79 | 0.08 | 1.56 | 3.95 |
| Mean | 6.78222 | 6.26000 | 3.81889 | 8.39888 | 6.96444 | 4.03222 | 4.18000 | 5.96998 | 5.45333 | 8.12556 | 5.99 |
| | | | | | | | | | SD all | | 6.88 |
| | | | | | | | | | M+2SD | | 19.37 |
| | | | | | | | | | M+3SD | | 25.90 |
| CpG | 27 | 29 | 31 | 34 | 37 | 44 | 46 | 55 | 65 | 74 | |
| ADENOMA | | | | | | | | | | | Mean |
| 3-4 | 42.34 | 7.24 | 13.95 | 15.1 | 34.96 | 13.74 | 20.19 | 23.02 | 14.87 | 25.63 | 21.11 |
| 3-5 | 75.62 | 55.47 | 57.53 | 79.82 | 76.73 | 47.75 | 54.51 | 49.28 | 39.16 | 52.03 | 58.79 |
| 3-6 | 94.03 | 94.1 | 83.31 | 86.55 | 87.59 | 92.01 | 88.59 | 85.93 | 38.32 | 65.91 | 81.64 |
| 3-7 | 95.43 | 96.07 | 95.59 | 96.71 | 95.27 | 92.45 | 93.84 | 89.14 | 68.37 | 72.86 | 89.47 |
| 3-8 | 95.86 | 98.62 | 49.24 | 95.35 | 79.11 | 96.8 | 94.79 | 92.04 | 61.34 | 70.73 | 82.38 |
| 3-9 | 14.55 | 23.73 | 33.45 | 24.76 | 18.33 | 11.66 | 13.59 | 23.87 | 8.92 | 47.61 | 31.94 |
| 3-10 | 13.57 | 23.33 | 29.82 | 21.68 | 36.82 | 10.17 | 13.21 | 21.32 | 7.26 | 44.63 | 20.23 |
| 3-11 | 97.79 | 98.59 | 97.35 | 97.61 | 82.96 | 94.87 | 96.87 | 43.46 | 62.52 | 84.81 | 85.67 |
| 3-12 | 65.73 | 63.48 | 64.89 | 71.19 | 67.66 | 63.9 | 72.68 | 63.74 | 39.26 | 68.67 | 66.52 |
| 5-1 | 90.16 | 93.09 | 89.89 | 95.48 | 81.65 | 33.24 | 91.22 | 36.5 | 56.12 | 78.33 | 78.39 |
| 5-2 | 83.81 | 71.43 | 80.95 | 87.62 | 79.52 | 27.62 | 79.52 | 58.1 | 48.71 | 86.19 | 66.85 |
| 5-4 | 28.96 | 38.8 | 27.69 | 64.66 | 61.75 | 13.3 | 38.63 | 14.57 | 12.93 | 48.45 | 34.97 |
| 5-11 | 94.41 | 94.41 | 93.31 | 87.2 | 93.93 | 28.33 | 76.82 | 66.38 | 38.86 | 80.07 | 76.05 |
| 5-12 | 98.72 | 96.76 | 91.09 | 97.17 | 92.9 | 11.74 | 58.3 | 25.51 | 38.48 | 86.64 | 69.43 |
| 6-1 | 95.83 | 96.8 | 96.28 | 96.51 | 94.84 | 94.06 | 96.72 | 89.86 | 67 | 73.73 | 88.84 |
| 6-2 | 89.63 | 87.37 | 86.85 | 88.6 | 83.53 | 86.34 | 83.86 | 83.31 | 52.22 | 62.18 | 81.53 |
| 6-3 | 97 | 96.79 | 95.1 | 96.68 | 95.73 | 95.3 | 94.9 | 82.6 | 99.33 | 71.11 | 88.45 |
| 6-4 | 47.71 | 38.77 | 29.19 | 83.03 | 38.35 | 14.73 | 24.06 | 15.42 | 5.76 | 28.73 | 31.68 |
| 6-5 | 15.86 | 7.45 | 9.51 | 20.1 | 13.44 | 8.9 | 5.48 | 15.51 | 8.9 | 31.4 | 11.44 |
| 6-6 | 85.06 | 85.26 | 84.76 | 85.88 | 84.14 | 85.06 | 84.83 | 79.57 | 64.17 | 63.75 | 80.25 |
| 7-5 | 93.96 | 94.73 | 95.05 | 92.77 | 94.15 | 92.06 | 90.55 | 87.51 | 60.32 | 65.65 | 86.72 |
| 7-6 | 92.6 | 93 | 92.47 | 92.76 | 83.23 | 91.36 | 87.57 | 86.05 | 63.1 | 64.39 | 84.64 |
| 7-7 | 61.1 | 61.34 | 58.78 | 65.15 | 62.99 | 59.16 | 68.7 | 52.74 | 37.07 | 44.89 | 56.47 |
| 7-8 | 17 | 11.63 | 8.37 | 25.03 | 17.31 | 5.2 | 4.95 | 13.93 | 3.31 | 50.91 | 15.68 |
| 7-9 | 80.81 | 74.06 | 77.28 | 82.16 | 76.42 | 76.69 | 77.13 | 73.52 | 52.25 | 65.57 | 73.56 |
| 7-10 | 77 | 73.06 | 70.81 | 78.33 | 72.76 | 78.15 | 74.08 | 69.86 | 51.78 | 64.53 | 70.84 |
| 7-11 | 0.53 | 0.84 | 9.01 | 2.12 | 16.04 | 6.46 | 9.41 | 8.97 | 12.98 | 13.93 | 8.93 |
| 7-12 | 73.35 | 76.12 | 76.18 | 71.6 | 75.34 | 74.97 | 76.41 | 64.9 | 82.94 | 51.83 | 68.36 |
| 8-1 | 89.74 | 89.94 | 90.18 | 89.41 | 88.4 | 88.60 | 88.68 | 74.41 | 70.39 | 76.14 | 84.80 |
| 8-2 | 98.69 | 96.5 | 98.29 | 97.68 | 92.95 | 97.53 | 97.08 | 79.52 | 75.3 | 86.15 | 91.49 |
| 8-3 | 89.79 | 93.32 | 94.97 | 94.28 | 71.33 | 59.43 | 61.38 | 34.46 | 42.65 | 55.09 | 89.73 |
| Mean | 70.7758 | 68.0194 | 66.7794 | 74.0771 | 68.6342 | 56.7288 | 64.6436 | 56.1645 | 41.8272 | 59.8526 | |
| N/M | 0.09583 | 0.08203 | 0.05719 | 0.11338 | 0.10130 | 0.07108 | 0.06416 | 0.10622 | 0.13050 | 0.13576 | |

FIG. 2J

| | EYA4 | | | | | | | | | | |
|---|---|---|---|---|---|---|---|---|---|---|---|
| CpG | 27 | 29 | 31 | 34 | 37 | 44 | 46 | 55 | 65 | 74 | |
| CANCER | | | | | | | | | | | Mean |
| 1-1 | 95.77 | 95.43 | 95.77 | 96.12 | 90.28 | 94.76 | 94.9 | 72.84 | 87.49 | 82.09 | 88.55 |
| 1-2 | 91.26 | 92.07 | 92.85 | 93.03 | 91.62 | 91.94 | 91.19 | 68.82 | 62.06 | 78.13 | 85.48 |
| 1-3 | 95.81 | 96.96 | 96.22 | 95.96 | 94.14 | 96.56 | 94.2 | 80.34 | 62.51 | 77.22 | 89.05 |
| 1-4 | 96.31 | 95.85 | 97.08 | 96.12 | 87.07 | 94.71 | 78.53 | 36.85 | 36.16 | 68.45 | 78.61 |
| 1-5 | 97.36 | 97.86 | 97.2 | 97.58 | 87.13 | 97.41 | 97.39 | 84.8 | 65.85 | 81.89 | 91.42 |
| 1-6 | 94.33 | 95.64 | 95.97 | 95.38 | 92.87 | 95.52 | 88.72 | 69.51 | 72.14 | 83.97 | 88.76 |
| 1-7 | 38.77 | 9.23 | 9.21 | 33.33 | 36.24 | 14.01 | 44.41 | 58.09 | 7.14 | 13.19 | 26.35 |
| 1-8 | 46.66 | 30.42 | 29.64 | 59.15 | 28.97 | 19.9 | 15.52 | 30.52 | 31.39 | 67.42 | 33.56 |
| 1-9 | 98.11 | 94.22 | 93.91 | 97.09 | 90.15 | 93.97 | 93.78 | 71.93 | 73.3 | 67.96 | 87.44 |
| 1-10 | 96.21 | 94.28 | 93.99 | 97.34 | 91.01 | 94.45 | 94.19 | 73.8 | 72.18 | 70.03 | 87.74 |
| 1-11 | 98.77 | 97.62 | 97.6 | 96.75 | 97.25 | 98.23 | 96.89 | 83.56 | 41.83 | 78.11 | 88.66 |
| 1-12 | 91.41 | 91.71 | 92.35 | 92.58 | 91.12 | 91.65 | 88.38 | 82.07 | 59.93 | 78.28 | 82.13 |
| 2-1 | 18.91 | 21.86 | 30.07 | 19.4 | 20.68 | 18.46 | 19.59 | 16.34 | 12.97 | 13.08 | 18.12 |
| 2-2 | 33.9 | 37.54 | 33.8 | 35.41 | 26.72 | 32.37 | 30.33 | 25.63 | 13.73 | 21.64 | 28.99 |
| 2-3 | 87.09 | 85.4 | 86.41 | 87.06 | 70.66 | 83.49 | 87.81 | 52.21 | 36.49 | 67.66 | 74.45 |
| 2-4 | 81.28 | 84.34 | 84.36 | 84.63 | 81.79 | 75.22 | 67.87 | 38.47 | 8.36 | 20.3 | 60.63 |
| 2-5 | 95.51 | 94.65 | 93.45 | 97.75 | 96.96 | 89.4 | 93.64 | 71.6 | 60.1 | 71.7 | 85.08 |
| 2-6 | 89.64 | 90.39 | 92 | 89.4 | 86.3 | 86.98 | 89.9 | 78.41 | 50.38 | 66.56 | 81.99 |
| 2-7 | 87.95 | 83.36 | 87.88 | 86.33 | 79.7 | 62.37 | 74.91 | 58.32 | 41.49 | 63.68 | 73.56 |
| 2-8 | 88.33 | 79.13 | 74.75 | 91.49 | 78.51 | 87.08 | 88.76 | 67.95 | 49.06 | 86.23 | 77.28 |
| 2-9 | 96.63 | 96.37 | 96.75 | 95.33 | 94.76 | 91.66 | 91.7 | 83.83 | 62.73 | 68.07 | 87.79 |
| 2-10 | 96.23 | 96.18 | 96.45 | 95.35 | 94.09 | 91.68 | 92.03 | 84.12 | 62.29 | 68.48 | 87.69 |
| 2-11 | 78.81 | 95.62 | 95.38 | 93.83 | 80.94 | 89.21 | 86.41 | 47.49 | 19.08 | 33.81 | 72.41 |
| 2-12 | 78.92 | 77.21 | 85.35 | 88.2 | 87.17 | 88.02 | 48.4 | 43.86 | 32.73 | 55.41 | 82.53 |
| 3-2 | 83.19 | 85.33 | 85.51 | 87.83 | 84.07 | 85.4 | 83.93 | 72.44 | 38.71 | 62.51 | 76.69 |
| 3-3 | 75 | 77.63 | 73.03 | 76.97 | 68.13 | 31.73 | 86.45 | 14.47 | 8.55 | 28.29 | 50.73 |
| 5-5 | 76.69 | 89.83 | 90.89 | 79.24 | 49.15 | 28.39 | 67.37 | 31.79 | 19.07 | 40.04 | 57.25 |
| 5-6 | 84.14 | 86.5 | 82.76 | 80.89 | 83.89 | 58.67 | 85.52 | 26.3 | 13.79 | 33.1 | 93.31 |
| 5-7 | 83.85 | 83.08 | 85 | 83.46 | 78.54 | 29.23 | 84.23 | 41.82 | 30.38 | 70 | 66.77 |
| 5-8 | 59.34 | 63.74 | 62.85 | 68.13 | 56.59 | 33.08 | 62.88 | 38.81 | 37.47 | 46.7 | 59.82 |
| 5-9 | 82.36 | 85.35 | 86.98 | 84.32 | 80.21 | 29.56 | 81.23 | 38.25 | 36.74 | 74.29 | 64.88 |
| 5-10 | 78.22 | 85.24 | 81.41 | 80.57 | 78.06 | 25.46 | 79.23 | 18.76 | 33.95 | 71.36 | 61.83 |
| 6-7 | 96.25 | 97.54 | 97.28 | 96.54 | 94.24 | 95.22 | 96.77 | 90.47 | 68.78 | 71.86 | 90.53 |
| 6-8 | 75.42 | 80.15 | 66.23 | 85.35 | 70.66 | 76.29 | 71.49 | 67.79 | 48.75 | 59.12 | 68.28 |
| 6-9 | 74.63 | 72.85 | 75.4 | 77.87 | 75.48 | 66.67 | 38.5 | 43.07 | 8.53 | 12.99 | 56.61 |
| 6-10 | 72.13 | 68.52 | 70.34 | 73.37 | 69.14 | 63.44 | 53.88 | 42.34 | 6.23 | 11.98 | 53.14 |
| 6-11 | 98.57 | 91.22 | 93.96 | 88.64 | 90.51 | 87.87 | 90.7 | 78.51 | 60.18 | 62.03 | 83.12 |
| 6-12 | 81.63 | 94.2 | 95.03 | 93.02 | 79.24 | 89.94 | 88.49 | 58.09 | 32.59 | 53.01 | 76.52 |
| 7-1 | 95.77 | 93.81 | 98.3 | 96.4 | 94.38 | 94.6 | 93.33 | 85.21 | 55.69 | 65.88 | 86.53 |
| 7-2 | 69.02 | 62.6 | 67.89 | 67.45 | 67.11 | 63.39 | 61.07 | 42.99 | 27.53 | 29.83 | 55.87 |
| 7-3 | 87.53 | 87.41 | 85.13 | 87.34 | 86.47 | 85.39 | 86.17 | 77.97 | 56.43 | 57.76 | 79.78 |
| 7-4 | 96.06 | 96.57 | 94.2 | 94.28 | 78.03 | 15.36 | 36.08 | 37.32 | 17.28 | 53.07 | 59.82 |
| Mean | 81.3805 | 80.3866 | 80.7457 | 83.5207 | 77.0824 | 67.5960 | 74.9510 | 55.1143 | 39.7569 | 56.8881 | |
| N/M | 0.0834 | 0.07787 | 0.04730 | 0.10608 | 0.09035 | 0.09965 | 0.05550 | 0.10632 | 0.13664 | 0.14282 | |

FIG. 3A

| Average of all individual base percent methylation | | | | | |
|---|---|---|---|---|---|
| Normal | Vim | BMP3 | Septin9 | TFPI2 | EYA4 |
| 8-4 | 4.98 | 3.06 | 3.61 | 14.74 | 9.41 |
| 8-5 | 2.33 | 2.03 | 3.77 | 9.27 | 2.04 |
| 8-6 | 5.07 | 2.38 | 6.36 | 4.93 | 2.40 |
| 8-7 | 6.80 | 2.59 | 16.67 | 5.44 | 18.20 |
| 8-8 | 3.22 | 3.40 | 7.68 | 3.45 | 5.58 |
| 8-9 | 2.34 | 3.51 | 2.74 | 7.44 | 2.37 |
| 8-10 | 2.38 | 1.78 | 2.94 | 7.37 | 1.12 |
| 8-11 | 3.57 | 3.02 | 7.70 | 4.91 | 8.90 |
| 8-12 | 2.95 | 2.51 | 5.28 | 4.38 | 3.93 |
| | | | | | |
| AVG | 3.73 | 2.70 | 6.30 | 6.88 | 5.99 |
| | | | | | |
| SD | 2.68 | 1.18 | 5.06 | 3.86 | 8.64 |
| M+2SD | 9.09 | 5.05 | 16.42 | 14.61 | 19.27 |
| M+3SD | 11.77 | 6.23 | 21.47 | 18.47 | 25.90 |

FIG. 3B

| Cut off | 11.77 | 6.23 | 20.45 | 18.47 | 25.90 |
|---|---|---|---|---|---|
| Adenom. | Vim | BMP3 | Septin9 | TFPI2 | EYA4 |
| 3-4 | 33.02 | 3.18 | 69.72 | 57.15 | 21.11 |
| 3-5 | 48.72 | 7.72 | 78.64 | 75.22 | 58.79 |
| 3-6 | 28.18 | 15.51 | 46.27 | 39.00 | 81.04 |
| 3-7 | 42.93 | 43.21 | 53.51 | 50.37 | 89.47 |
| 3-8 | 44.83 | 6.06 | 82.42 | 77.10 | 82.38 |
| 3-9 | 3.46 | 3.92 | 59.57 | 40.03 | 21.94 |
| 3-10 | 3.06 | 3.43 | 59.63 | 38.38 | 20.23 |
| 3-11 | 65.55 | 5.73 | 81.64 | 82.63 | 85.67 |
| 3-12 | 86.85 | 5.17 | 86.93 | 79.90 | 66.52 |
| 5-1 | 68.87 | 85.58 | 81.96 | 75.61 | 78.38 |
| 5-2 | 33.82 | 30.62 | 56.59 | 54.84 | 66.05 |
| 5-4 | 26.24 | 4.55 | 90.02 | 89.53 | 34.97 |
| 5-11 | 67.61 | 21.82 | 81.63 | 69.52 | 76.05 |
| 5-12 | 73.21 | 16.29 | 87.02 | 80.95 | 69.43 |
| 6-1 | 84.71 | 88.85 | 88.50 | 84.55 | 89.84 |
| 6-2 | 39.59 | 3.03 | 52.23 | 49.87 | 80.32 |
| 6-3 | 58.43 | 80.64 | 74.09 | 69.00 | 88.45 |
| 6-4 | 47.21 | 2.70 | 57.83 | 44.62 | 31.68 |
| 6-5 | 5.61 | 2.48 | 30.38 | 13.55 | 11.44 |
| 6-6 | 43.89 | 24.86 | 46.26 | 48.49 | 80.25 |
| 7-5 | 69.02 | 40.58 | 71.45 | 56.40 | 86.72 |
| 7-6 | 48.96 | 69.83 | 66.99 | 50.01 | 84.64 |
| 7-7 | 13.62 | 13.58 | 38.71 | 19.79 | 56.47 |
| 7-8 | 18.39 | 11.86 | 71.98 | 30.74 | 15.60 |
| 7-9 | 76.46 | 20.55 | 81.36 | 65.33 | 73.56 |
| 7-10 | 77.85 | 14.79 | 81.33 | 63.10 | 70.84 |
| 7-11 | 9.05 | 5.08 | 74.97 | 56.71 | 8.93 |
| 7-12 | 31.77 | 26.83 | 27.93 | 24.87 | 68.36 |
| 8-1 | 48.49 | 55.86 | 47.43 | 38.01 | 84.80 |
| 8-2 | 81.28 | 81.73 | 78.33 | 4.67 | 91.49 |
| 8-3 | 63.37 | 1.84 | 73.26 | 9.52 | 69.73 |
|  | 87.10 | 61.29 | 100.00 | 90.32 | 80.65 |
| Vim, BMP, Sep TFPI2 |  |  |  | 100 |  |

FIG. 3C

| Cancer | Vim | BMP3 | Septin9 | TFPI2 | EYA4 |
|---|---|---|---|---|---|
| 1-1 | 38.80 | 3.11 | 72.66 | 75.29 | 88.55 |
| 1-2 | 34.74 | 2.01 | 64.15 | 59.09 | 85.48 |
| 1-3 | 13.19 | 3.02 | 78.77 | 68.12 | 89.05 |
| 1-4 | 77.62 | 5.51 | 74.27 | 77.45 | 78.61 |
| 1-5 | 84.93 | 84.69 | 82.00 | 77.97 | 91.42 |
| 1-6 | 72.92 | 68.88 | 72.83 | 71.18 | 88.76 |
| 1-7 | 8.37 | 3.35 | 58.66 | 37.29 | 76.35 |
| 1-8 | 3.19 | 2.68 | 39.30 | 30.00 | 33.56 |
| 1-9 | 86.69 | 20.30 | 87.12 | 84.60 | 87.44 |
| 1-10 | 86.72 | 19.05 | 87.45 | 83.78 | 87.74 |
| 1-11 | 72.01 | 7.18 | 91.29 | 67.89 | 89.66 |
| 1-12 | 49.26 | 2.79 | 52.59 | 65.89 | 82.13 |
| 2-1 | 2.81 | 1.96 | 58.49 | 12.75 | 18.12 |
| 2-2 | 25.33 | 2.51 | 54.09 | 17.58 | 28.99 |
| 2-3 | 49.44 | 47.22 | 49.61 | 43.69 | 74.45 |
| 2-4 | 45.03 | 7.18 | 43.66 | 43.06 | 60.63 |
| 2-5 | 3.42 | 74.17 | 66.30 | 61.27 | 85.08 |
| 2-6 | 38.28 | 42.91 | 18.62 | 29.96 | 81.90 |
| 2-7 | 54.05 | 56.75 | 42.19 | 43.39 | 72.56 |
| 2-8 | 61.55 | 7.65 | 68.72 | 61.66 | 77.28 |
| 2-9 | 3.59 | 83.18 | 71.20 | 73.77 | 87.79 |
| 2-10 | 3.05 | 82.80 | 70.51 | 70.48 | 87.69 |
| 2-11 | 64.29 | 61.54 | 21.90 | 56.83 | 72.41 |
| 2-12 | 43.51 | 3.18 | 57.66 | 52.05 | 62.62 |
| 3-2 | 45.20 | 52.41 | 46.70 | 42.30 | 76.89 |
| 5-3 | 39.27 | 26.61 | 48.36 | 36.41 | 50.72 |
| 5-5 | 8.72 | 16.58 | 29.14 | 56.02 | 57.25 |
| 5-6 | 8.00 | 2.62 | 64.43 | 33.04 | 53.31 |
| 5-7 | 40.50 | 3.87 | 57.83 | 60.34 | 66.77 |
| 5-8 | 20.77 | 36.11 | 31.25 | 19.52 | 50.82 |
| 5-9 | 40.55 | 6.67 | 57.52 | 49.73 | 64.86 |
| 5-10 | 39.62 | 5.65 | 56.99 | 47.24 | 61.83 |
| 6-7 | 88.95 | 86.24 | 85.46 | 82.97 | 90.53 |
| 6-8 | 57.90 | 49.40 | 61.73 | 48.26 | 68.28 |
| 6-9 | 5.14 | 2.80 | 55.38 | 26.03 | 56.61 |
| 6-10 | 3.66 | 2.39 | 54.41 | 25.27 | 53.14 |
| 6-11 | 64.29 | 51.17 | 2.67 | 56.67 | 83.12 |
| 6-12 | 40.48 | 14.45 | 75.85 | 59.01 | 76.52 |
| 7-1 | 55.25 | 2.38 | 62.71 | 60.39 | 86.63 |
| 7-2 | 29.60 | 3.17 | 63.49 | 37.72 | 59.87 |
| 7-3 | 59.56 | 63.21 | 73.54 | 53.88 | 79.78 |
| 7-4 | 71.98 | 3.07 | 77.84 | 67.69 | 59.82 |
| | 76.19 | 57.14 | 95.24 | 95.24 | 97.62 |
| Vim, BMP, Sep TFPI2 | | | | 100 | |

FIG. 3D

| | Twenty fold dilution at 37.5% specificity (+2SD of mean) | | | | |
|---|---|---|---|---|---|
| Cut off | 9.09 | 5.05 | 15.73 | 14.61 | 19.27 |
| Adenom. | Vim | BMP3 | Septin9 | TFPI2 | EYA4 |
| 3-4 | 5.38 | 2.86 | 9.79 | 9.74 | 7.05 |
| 3-5 | 6.16 | 3.09 | 10.24 | 10.64 | 8.93 |
| 3-6 | 5.14 | 3.48 | 8.62 | 8.83 | 10.05 |
| 3-7 | 5.87 | 4.86 | 8.98 | 9.40 | 10.47 |
| 3-8 | 5.97 | 3.00 | 10.43 | 10.74 | 10.11 |
| 3-9 | 3.90 | 2.90 | 9.28 | 8.88 | 7.09 |
| 3-10 | 3.88 | 2.87 | 9.29 | 8.80 | 7.01 |
| 3-11 | 7.00 | 2.99 | 10.39 | 11.01 | 10.28 |
| 3-12 | 8.07 | 2.96 | 10.65 | 10.88 | 9.32 |
| 5-1 | 7.17 | 6.98 | 10.40 | 10.66 | 9.91 |
| 5-3 | 5.37 | 4.23 | 9.13 | 9.62 | 9.30 |
| 5-4 | 5.04 | 2.93 | 10.81 | 11.36 | 7.74 |
| 5-11 | 7.11 | 3.79 | 10.39 | 10.36 | 9.80 |
| 5-12 | 7.39 | 3.51 | 10.66 | 10.93 | 9.47 |
| 6-1 | 7.96 | 7.14 | 10.73 | 11.11 | 10.49 |
| 6-2 | 5.71 | 2.85 | 8.92 | 9.37 | 10.01 |
| 6-3 | 8.65 | 6.73 | 10.01 | 10.33 | 10.42 |
| 6-4 | 6.09 | 2.83 | 9.20 | 9.11 | 7.58 |
| 6-5 | 4.01 | 2.82 | 7.82 | 7.56 | 6.57 |
| 6-6 | 5.92 | 3.94 | 8.62 | 9.31 | 10.01 |
| 7-5 | 7.18 | 4.73 | 9.88 | 9.70 | 10.33 |
| 7-6 | 6.17 | 6.19 | 9.65 | 9.38 | 10.23 |
| 7-7 | 4.41 | 3.38 | 8.24 | 7.87 | 8.83 |
| 7-8 | 4.65 | 3.29 | 9.90 | 8.42 | 6.77 |
| 7-9 | 7.55 | 3.73 | 10.37 | 10.15 | 9.67 |
| 7-10 | 7.62 | 3.44 | 10.37 | 10.04 | 9.54 |
| 7-11 | 4.18 | 2.95 | 10.05 | 9.72 | 8.44 |
| 7-12 | 5.31 | 4.04 | 7.70 | 8.12 | 9.41 |
| 8-1 | 6.20 | 5.49 | 8.68 | 8.78 | 10.23 |
| 8-2 | 7.79 | 6.79 | 10.22 | 7.11 | 10.57 |
| 8-3 | 6.90 | 2.79 | 9.97 | 7.36 | 9.48 |
| | 0.00 | 12.90 | 0.00 | 0.00 | 0.00 |
| Vim, BMP, Sep TFPI2 | | | | 12.90 | |

FIG. 3E

| | | Twenty fold dilution | | | | |
| --- | --- | --- | --- | --- | --- | --- |
| | | at 97.5% specificity (+2SD of mean) | | | | |
| | Cancer | Vim | BMP3 | Septin9 | TFPI2 | EYA4 |
| | | 5.67 | 2.86 | 9.94 | 10.64 | 10.42 |
| | | 5.46 | 2.80 | 9.51 | 9.83 | 10.27 |
| | | 4.39 | 2.85 | 10.14 | 10.29 | 10.43 |
| | | 7.61 | 2.97 | 10.02 | 10.75 | 9.92 |
| | | 7.97 | 6.93 | 10.40 | 10.78 | 10.56 |
| | | 7.37 | 6.14 | 9.95 | 10.44 | 10.43 |
| | | 4.14 | 2.87 | 9.24 | 8.74 | 7.31 |
| | | 3.89 | 2.83 | 8.27 | 8.38 | 7.67 |
| | | 8.06 | 3.71 | 10.66 | 11.11 | 10.37 |
| | | 8.06 | 3.65 | 10.68 | 11.07 | 10.38 |
| | | 7.33 | 3.06 | 10.87 | 10.28 | 10.48 |
| | | 6.19 | 2.84 | 8.93 | 10.18 | 10.10 |
| | | 3.87 | 2.80 | 9.23 | 7.52 | 6.90 |
| | | 4.99 | 2.82 | 9.01 | 7.76 | 7.44 |
| | | 6.20 | 5.06 | 8.79 | 9.07 | 9.72 |
| | | 3.98 | 3.06 | 8.49 | 9.03 | 9.03 |
| | | 3.90 | 6.41 | 9.62 | 9.94 | 10.25 |
| | | 5.64 | 4.85 | 7.24 | 8.38 | 10.09 |
| | | 6.43 | 5.54 | 8.41 | 9.05 | 9.62 |
| | | 6.80 | 3.08 | 9.74 | 9.96 | 9.86 |
| | | 3.91 | 6.86 | 9.86 | 10.57 | 10.38 |
| | | 3.88 | 6.84 | 9.83 | 10.40 | 10.38 |
| | | 6.94 | 5.78 | 7.40 | 9.72 | 9.61 |
| | | 5.90 | 2.86 | 9.19 | 9.48 | 9.12 |
| | | 5.99 | 5.32 | 8.64 | 9.00 | 9.83 |
| | S-3 | 5.19 | 4.03 | 8.72 | 8.70 | 8.53 |
| | S-5 | 4.16 | 3.53 | 7.76 | 9.68 | 8.86 |
| | S-6 | 4.13 | 2.83 | 9.53 | 8.53 | 8.66 |
| | S-7 | 5.75 | 2.89 | 9.20 | 9.90 | 9.33 |
| | S-8 | 4.76 | 4.51 | 7.87 | 7.86 | 8.54 |
| | S-9 | 5.75 | 3.03 | 9.18 | 9.37 | 9.24 |
| | S-10 | 5.71 | 2.98 | 9.15 | 9.24 | 9.09 |
| | | 8.17 | 7.01 | 10.58 | 11.03 | 10.52 |
| | | 6.62 | 5.17 | 9.39 | 9.29 | 8.41 |
| | | 3.98 | 2.84 | 9.07 | 8.18 | 8.82 |
| | | 3.91 | 2.81 | 9.03 | 8.14 | 8.65 |
| | | 6.94 | 5.26 | 6.44 | 9.71 | 10.15 |
| | | 5.75 | 3.42 | 10.10 | 9.83 | 8.82 |
| | | 6.49 | 2.82 | 9.44 | 9.90 | 10.32 |
| | | 5.21 | 2.86 | 9.48 | 8.77 | 8.79 |
| | | 6.70 | 5.86 | 9.98 | 9.57 | 9.98 |
| | | 7.33 | 2.85 | 10.20 | 10.26 | 8.99 |
| | | | | | | |
| | | 0.00 | 23.81 | 0.00 | 0.00 | 0.00 |
| | | | | | | |
| | Vim, BMP, Sep TFPI2 | | | | 23.81 | |

FIG. 3F

| | Ten Fold dilution at 97.5% specificity (+2SD of mean) | | | | |
|---|---|---|---|---|---|
| Cut off | 9.09 | 5.05 | 15.73 | 14.61 | 19.27 |
| Adenom. | Vim | BMP3 | Septin9 | TFPI2 | EYA4 |
| 3-4 | 7.03 | 3.02 | 13.28 | 12.60 | 8.10 |
| 3-5 | 8.60 | 3.47 | 14.17 | 14.40 | 11.87 |
| 3-6 | 6.54 | 4.25 | 10.93 | 10.78 | 14.10 |
| 3-7 | 8.02 | 7.02 | 11.66 | 11.92 | 14.94 |
| 3-8 | 8.21 | 3.31 | 14.55 | 14.59 | 14.23 |
| 3-9 | 4.07 | 3.09 | 12.26 | 10.88 | 8.19 |
| 3-10 | 4.03 | 3.04 | 12.27 | 10.72 | 8.02 |
| 3-11 | 10.28 | 3.27 | 14.47 | 15.14 | 14.56 |
| 3-12 | 12.41 | 3.22 | 15.00 | 14.87 | 12.65 |
| 5-1 | 10.61 | 11.36 | 14.50 | 14.44 | 13.83 |
| 5-2 | 7.01 | 5.76 | 11.96 | 12.36 | 12.60 |
| 5-4 | 6.35 | 3.15 | 15.31 | 15.83 | 9.49 |
| 5-11 | 10.49 | 4.88 | 14.47 | 13.83 | 13.60 |
| 5-12 | 11.05 | 4.33 | 15.01 | 14.98 | 12.94 |
| 6-1 | 12.20 | 11.58 | 15.15 | 15.34 | 14.99 |
| 6-2 | 7.69 | 3.00 | 11.53 | 11.87 | 14.03 |
| 6-3 | 9.57 | 10.76 | 13.71 | 13.78 | 14.84 |
| 6-4 | 8.45 | 2.97 | 12.09 | 11.34 | 9.16 |
| 6-5 | 4.29 | 2.95 | 9.34 | 8.24 | 7.14 |
| 6-6 | 8.12 | 5.19 | 10.93 | 11.73 | 14.02 |
| 7-5 | 10.63 | 6.76 | 13.45 | 12.52 | 14.67 |
| 7-6 | 8.62 | 9.68 | 13.00 | 11.88 | 14.46 |
| 7-7 | 5.09 | 4.06 | 10.18 | 8.86 | 11.64 |
| 7-8 | 5.57 | 3.89 | 13.50 | 9.95 | 7.55 |
| 7-9 | 11.37 | 4.75 | 14.44 | 13.41 | 13.34 |
| 7-10 | 11.51 | 4.18 | 14.44 | 13.19 | 13.08 |
| 7-11 | 4.63 | 3.21 | 13.80 | 12.55 | 6.89 |
| 7-12 | 6.90 | 5.38 | 9.10 | 9.37 | 12.83 |
| 8-1 | 8.67 | 8.29 | 11.05 | 10.68 | 14.47 |
| 8-2 | 11.85 | 10.87 | 14.14 | 7.35 | 15.14 |
| 8-3 | 10.06 | 2.88 | 13.63 | 7.83 | 12.97 |
| | 38.71 | 35.48 | 0.00 | 16.13 | 0.00 |
| Vim, BMP, Sep TFPI2 | | | | 61.29 | |

FIG. 3G

| | | Ten Fold dilution | | | |
| --- | --- | --- | --- | --- | --- |
| | | at 97.5% specificity (+2SD of mean) | | | |
| | Cancer | Vim | BMP3 | Septin9 | TFPI2 | EYA4 |
| | | 7.61 | 3.01 | 13.57 | 14.41 | 14.85 |
| | | 7.20 | 2.90 | 12.72 | 12.79 | 14.54 |
| | | 5.05 | 3.00 | 13.98 | 13.69 | 14.30 |
| | | 11.49 | 3.25 | 13.73 | 14.63 | 13.86 |
| | | 12.22 | 11.17 | 14.51 | 14.68 | 15.14 |
| | | 11.02 | 9.59 | 13.59 | 14.00 | 14.87 |
| | | 4.56 | 3.03 | 12.17 | 10.61 | 8.63 |
| | | 4.05 | 2.97 | 10.23 | 9.88 | 9.35 |
| | | 12.40 | 4.73 | 15.02 | 15.34 | 14.74 |
| | | 12.40 | 4.60 | 15.05 | 15.26 | 14.77 |
| | | 10.93 | 3.42 | 15.43 | 13.67 | 14.36 |
| | | 8.65 | 2.98 | 11.56 | 13.47 | 14.21 |
| | | 4.01 | 2.90 | 12.15 | 8.16 | 7.81 |
| | | 6.26 | 2.95 | 11.71 | 8.64 | 8.89 |
| | | 8.67 | 7.42 | 11.27 | 11.25 | 13.44 |
| | | 8.23 | 3.42 | 10.67 | 11.19 | 12.06 |
| | | 4.07 | 10.12 | 12.93 | 13.01 | 14.50 |
| | | 7.55 | 6.99 | 8.17 | 9.88 | 14.19 |
| | | 9.13 | 8.37 | 10.52 | 11.22 | 13.25 |
| | | 9.88 | 3.46 | 13.18 | 13.05 | 13.72 |
| | | 4.09 | 11.02 | 13.43 | 14.26 | 14.77 |
| | | 4.03 | 10.98 | 13.36 | 13.93 | 14.76 |
| | | 10.16 | 8.85 | 8.49 | 12.56 | 13.23 |
| | | 8.08 | 3.02 | 12.07 | 12.09 | 12.25 |
| | | 8.25 | 7.94 | 10.97 | 11.11 | 13.66 |
| | S-3 | 6.65 | 5.36 | 11.14 | 10.52 | 11.07 |
| | S-5 | 4.60 | 4.36 | 9.22 | 12.48 | 11.72 |
| | S-6 | 4.53 | 2.96 | 12.75 | 10.18 | 11.33 |
| | S-7 | 7.78 | 3.09 | 12.09 | 12.91 | 12.67 |
| | S-8 | 5.80 | 6.31 | 9.43 | 8.83 | 11.08 |
| | S-9 | 7.78 | 3.37 | 12.06 | 11.85 | 12.48 |
| | S-10 | 7.69 | 3.26 | 12.00 | 11.60 | 12.18 |
| | | 12.62 | 11.32 | 14.85 | 15.18 | 15.05 |
| | | 9.52 | 7.64 | 12.48 | 11.71 | 12.82 |
| | | 4.24 | 2.98 | 11.84 | 9.48 | 11.65 |
| | | 4.09 | 2.93 | 11.75 | 9.41 | 11.31 |
| | | 10.16 | 7.83 | 6.57 | 12.55 | 14.31 |
| | | 7.77 | 4.14 | 13.89 | 12.78 | 13.65 |
| | | 9.25 | 2.94 | 12.58 | 12.92 | 14.64 |
| | | 6.69 | 3.02 | 12.65 | 10.65 | 11.58 |
| | | 9.68 | 9.02 | 13.66 | 12.27 | 13.97 |
| | | 10.92 | 3.01 | 14.09 | 13.65 | 11.98 |
| | | | | | | |
| | | 35.71 | 38.10 | 0.00 | 11.90 | 0.00 |
| | | | | | | |
| | Vim, BMP, Sep TFPI2 | | | | 54.76 | |

FIG. 3H

| | Five Fold dilution | | | | |
|---|---|---|---|---|---|
| | at 97.5% specificity (+2SD of mean) | | | | |
| | | | | | |
| Cut off | 9.09 | 5.05 | 15.73 | 14.61 | 19.27 |
| Adenom. | Vim | BMP3 | Septin9 | TFPI2 | EYA4 |
| 3-4 | 10.33 | 3.34 | 20.25 | 18.31 | 10.22 |
| 3-5 | 13.47 | 4.24 | 22.03 | 21.93 | 17.75 |
| 3-6 | 9.36 | 5.80 | 15.56 | 14.68 | 22.20 |
| 3-7 | 12.31 | 11.34 | 17.01 | 16.95 | 23.89 |
| 3-8 | 12.69 | 3.91 | 22.79 | 22.30 | 22.47 |
| 3-9 | 4.42 | 3.48 | 18.22 | 14.89 | 10.38 |
| 3-10 | 4.34 | 3.39 | 18.23 | 14.56 | 10.04 |
| 3-11 | 16.84 | 3.85 | 22.63 | 23.41 | 23.13 |
| 3-12 | 21.10 | 3.73 | 23.69 | 22.86 | 19.30 |
| 5-1 | 17.50 | 19.81 | 22.70 | 22.00 | 21.67 |
| 5-2 | 10.29 | 8.82 | 17.62 | 17.85 | 19.20 |
| 5-4 | 8.97 | 3.61 | 24.31 | 24.79 | 12.99 |
| 5-11 | 17.25 | 7.06 | 22.63 | 20.78 | 21.20 |
| 5-12 | 18.37 | 5.96 | 23.71 | 23.07 | 19.88 |
| 6-1 | 20.67 | 20.47 | 24.00 | 23.79 | 23.98 |
| 6-2 | 11.64 | 3.31 | 16.75 | 16.85 | 22.06 |
| 6-3 | 15.41 | 18.83 | 21.12 | 20.68 | 23.68 |
| 6-4 | 13.17 | 3.24 | 17.87 | 15.80 | 12.33 |
| 6-5 | 4.85 | 3.20 | 12.38 | 9.59 | 8.28 |
| 6-6 | 12.51 | 7.67 | 15.56 | 16.58 | 22.04 |
| 7-5 | 17.53 | 10.81 | 20.59 | 18.16 | 23.34 |
| 7-6 | 13.52 | 16.66 | 19.70 | 16.88 | 22.92 |
| 7-7 | 6.45 | 5.42 | 14.05 | 10.84 | 17.29 |
| 7-8 | 7.40 | 5.07 | 20.70 | 13.03 | 9.11 |
| 7-9 | 19.02 | 6.61 | 22.58 | 19.95 | 20.69 |
| 7-10 | 19.30 | 6.66 | 22.57 | 19.50 | 20.16 |
| 7-11 | 5.54 | 3.72 | 21.30 | 18.22 | 7.78 |
| 7-12 | 10.08 | 8.07 | 11.89 | 11.86 | 19.67 |
| 8-1 | 13.62 | 13.87 | 15.79 | 14.48 | 22.95 |
| 8-2 | 19.98 | 19.05 | 21.97 | 7.81 | 24.29 |
| 8-3 | 16.40 | 3.07 | 20.96 | 8.78 | 19.94 |
| | | | | | |
| | 77.42 | 51.61 | 83.87 | 70.97 | 64.52 |
| | | | | | |
| Vim, BMP, Sep TFPI2 | | | | | 96.77 |

FIG. 3I

| Cancer | Five fold dilution at 97.5% specificity (+2SD of mean) | | | | |
|---|---|---|---|---|---|
| | Vim | BMP3 | Septin9 | TFPI2 | EYA4 |
| | 11.49 | 3.32 | 20.84 | 21.94 | 23.70 |
| | 10.67 | 3.10 | 19.14 | 18.70 | 23.08 |
| | 6.36 | 3.30 | 21.86 | 20.59 | 23.86 |
| | 19.25 | 3.80 | 21.16 | 22.37 | 21.72 |
| | 20.71 | 19.64 | 22.71 | 22.47 | 24.28 |
| | 18.31 | 16.48 | 20.87 | 21.12 | 23.75 |
| | 5.40 | 3.37 | 18.04 | 14.34 | 11.26 |
| | 4.36 | 3.24 | 14.16 | 12.88 | 12.71 |
| | 21.06 | 6.76 | 23.73 | 23.80 | 23.48 |
| | 21.07 | 6.51 | 23.79 | 23.64 | 23.54 |
| | 18.13 | 4.14 | 24.56 | 20.46 | 23.93 |
| | 13.58 | 3.26 | 16.82 | 20.06 | 22.42 |
| | 4.29 | 3.09 | 18.00 | 9.43 | 9.62 |
| | 8.79 | 3.20 | 17.12 | 10.40 | 11.79 |
| | 13.61 | 12.14 | 16.23 | 15.62 | 20.88 |
| | 12.73 | 4.13 | 15.03 | 15.49 | 18.12 |
| | 4.41 | 17.53 | 19.56 | 19.13 | 23.01 |
| | 11.38 | 11.28 | 10.03 | 12.87 | 22.39 |
| | 14.54 | 14.05 | 14.74 | 15.56 | 20.51 |
| | 16.04 | 4.23 | 20.05 | 19.21 | 21.45 |
| | 4.44 | 19.34 | 20.55 | 21.65 | 23.55 |
| | 4.34 | 19.26 | 20.41 | 20.98 | 23.53 |
| | 16.58 | 15.01 | 10.68 | 18.25 | 20.48 |
| | 12.43 | 3.34 | 17.84 | 17.39 | 18.50 |
| | 12.77 | 13.18 | 15.65 | 15.34 | 21.33 |
| S-3 | 9.58 | 8.03 | 15.98 | 14.16 | 16.14 |
| S-5 | 5.47 | 6.02 | 12.13 | 18.08 | 17.44 |
| S-6 | 5.33 | 3.22 | 19.19 | 13.49 | 16.66 |
| S-7 | 11.83 | 3.47 | 17.87 | 18.95 | 19.35 |
| S-8 | 7.88 | 9.92 | 12.55 | 10.78 | 16.16 |
| S-9 | 11.84 | 4.03 | 17.81 | 16.83 | 18.97 |
| S-10 | 11.65 | 3.83 | 17.70 | 16.33 | 18.36 |
| | 21.52 | 19.95 | 23.40 | 23.46 | 24.10 |
| | 15.31 | 12.58 | 18.65 | 16.53 | 19.65 |
| | 4.75 | 3.26 | 17.38 | 12.09 | 17.32 |
| | 4.46 | 3.16 | 17.19 | 11.93 | 16.62 |
| | 16.58 | 12.93 | 6.84 | 18.32 | 22.62 |
| | 11.82 | 5.59 | 21.47 | 18.68 | 21.30 |
| | 14.78 | 3.18 | 18.85 | 18.96 | 23.30 |
| | 9.65 | 3.33 | 18.00 | 14.42 | 17.17 |
| | 15.64 | 15.34 | 21.01 | 17.66 | 21.85 |
| | 18.12 | 3.31 | 21.87 | 20.42 | 17.96 |
| | | | | | |
| | 69.05 | 47.62 | 78.57 | 59.52 | 59.52 |
| Vim, BMP, Sep TFPI2 | | | | 97.62 | |

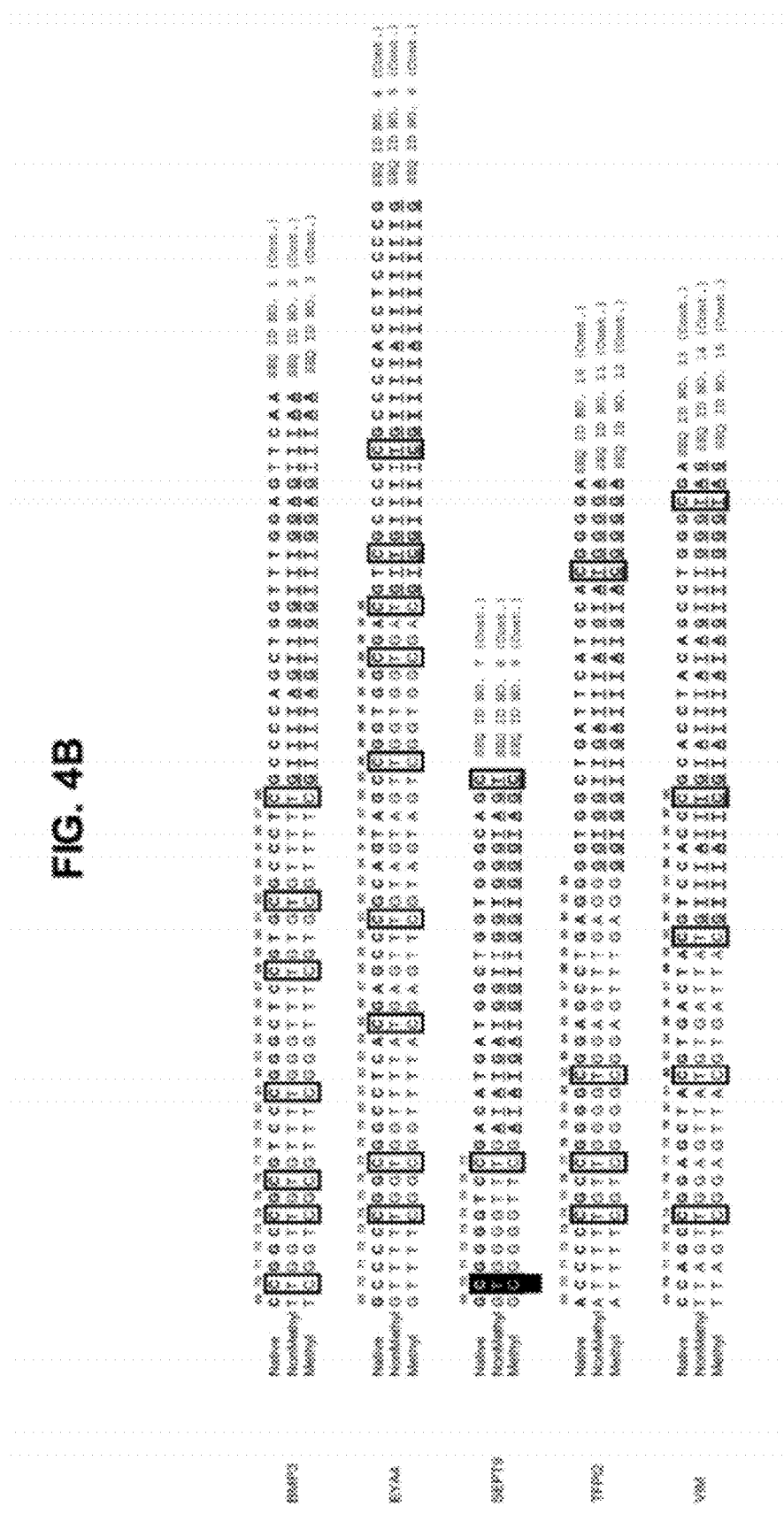

FIG. 5A

| Methylation for specific sequence identified | | | | | | |
|---|---|---|---|---|---|---|
| | | Vim | BMP3 | SEPTIN9 | TFPI2 | EYA4 |
| | CpG loci: | 37,40,45 | 34,53,61 | 59,61,68,71 | 55,59,63,6 | 31,34,37,44 |
| Normal | | | | | | |
| 8-4 | | | 1.20% | 0.18% | 0.56% | 5.46% | 3.17% |
| 8-5 | | | 0.20% | 0.38% | 0.71% | 3.28% | 0.03% |
| 8-6 | | | 1.89% | 0.02% | 0.78% | 0.74% | 0.00% |
| 8-7 | | | 1.62% | 0.02% | 3.77% | 0.84% | 3.85% |
| 8-8 | | | 0.14% | 0.01% | 1.19% | 0.13% | 0.39% |
| 8-9 | | | 0.01% | 0.01% | 0.07% | 0.82% | 0.09% |
| 8-10 | | | 0.04% | 0.01% | 0.13% | 0.91% | 0.09% |
| 8-11 | | | 0.40% | 0.12% | 1.52% | 0.72% | 8.49% |
| 8-12 | | | 0.47% | 0.12% | 0.29% | 0.05% | 0.06% |
| | | | | | | | |
| Mean (M) | | | 0.65% | 0.10% | 1.00% | 1.44% | 1.80% |
| Std Dev | | | 0.72% | 0.12% | 1.14% | 1.77% | 2.92% |
| M+2SD | | | 2.10% | 0.34% | 3.29% | 4.99% | 7.63% |
| M+3SD | | | 2.82% | 0.46% | 4.43% | 6.76% | 10.55% |

FIG. 5B

| Cut off | 2.82% | 0.46% | 4.43% | 6.76% | 10.55% |
|---|---|---|---|---|---|
| Adenoma | Vim | BMP3 | Septin9 | TFPI2 | EYA4 |
| 3-4 | 19.13% | 0.24% | 60.96% | 39.99% | 2.07% |
| 3-5 | 47.82% | 0.90% | 72.27% | 63.44% | 32.24% |
| 3-6 | 21.85% | 0.52% | 39.62% | 30.80% | 84.77% |
| 3-7 | 39.45% | 37.77% | 47.14% | 39.66% | 89.11% |
| 3-8 | 39.08% | 0.01% | 77.07% | 67.72% | 43.80% |
| 3-9 | 0.39% | 0.28% | 55.75% | 32.78% | 1.43% |
| 3-10 | 0.03% | 0.01% | 55.92% | 32.13% | 0.38% |
| 3-11 | 39.51% | 0.03% | 77.15% | 76.22% | 77.21% |
| 3-12 | 65.15% | 0.01% | 76.97% | 58.54% | 54.28% |
| 5-1 | 61.69% | 81.06% | 76.07% | 64.26% | 27.66% |
| 5-2 | 26.34% | 17.95% | 47.65% | 43.47% | 16.19% |
| 5-4 | 11.27% | 0.00% | 82.45% | 74.81% | 3.10% |
| 5-11 | 61.64% | 10.99% | 74.59% | 56.40% | 34.88% |
| 5-12 | 71.24% | 2.97% | 79.10% | 68.40% | 9.72% |
| 6-1 | 83.10% | 85.08% | 84.48% | 76.31% | 87.64% |
| 6-2 | 34.40% | 0.42% | 44.25% | 41.48% | 76.82% |
| 6-3 | 52.17% | 77.28% | 65.30% | 60.27% | 88.40% |
| 6-4 | 37.43% | 0.07% | 34.06% | 24.61% | 2.53% |
| 6-5 | 1.08% | 0.04% | 10.43% | 2.12% | 0.69% |
| 6-6 | 41.40% | 21.23% | 39.85% | 41.53% | 80.47% |
| 7-5 | 57.63% | 37.63% | 65.54% | 48.68% | 87.46% |
| 7-6 | 40.31% | 64.61% | 61.84% | 44.08% | 80.73% |
| 7-7 | 8.25% | 10.01% | 31.53% | 11.86% | 51.78% |
| 7-8 | 11.07% | 6.96% | 50.61% | 11.99% | 0.34% |
| 7-9 | 75.10% | 14.42% | 72.15% | 46.46% | 59.02% |
| 7-10 | 76.96% | 7.96% | 70.54% | 42.87% | 53.10% |
| 7-11 | 3.41% | 0.08% | 50.03% | 30.58% | 0.39% |
| 7-12 | 29.62% | 23.60% | 33.02% | 17.75% | 69.49% |
| 8-1 | 45.04% | 52.59% | 42.61% | 32.02% | 88.68% |
| 8-2 | 80.42% | 78.85% | 73.17% | 0.36% | 89.99% |
| 8-3 | 61.90% | 0.01% | 69.09% | 2.59% | 52.72% |
| | | | | | |
| Sensitivity | | | | | |
| | 90.32 | 58.06 | 100.00 | 90.32 | 70.97 |
| | | | | | |
| vim,BMP3,Sep,TFPI2 | | | 100.00% | | |

FIG. 5C

| Cancer | Vim | BMP3 | Septin9 | TFPI2 | EYA4 |
|---|---|---|---|---|---|
| 1-1 | 33.41% | 0.13% | 61.93% | 67.12% | 85.88% |
| 1-2 | 17.64% | 0.06% | 59.03% | 52.16% | 88.01% |
| 1-3 | 1.73% | 0.04% | 65.33% | 58.72% | 89.62% |
| 1-4 | 64.08% | 0.31% | 57.10% | 45.72% | 82.91% |
| 1-5 | 82.75% | 81.13% | 71.85% | 66.41% | 94.37% |
| 1-6 | 72.60% | 65.11% | 67.97% | 64.34% | 90.24% |
| 1-7 | 1.69% | 0.09% | 53.46% | 18.01% | 1.49% |
| 1-8 | 0.56% | 0.27% | 36.22% | 23.61% | 5.03% |
| 1-9 | 87.66% | 10.27% | 80.69% | 81.23% | 84.91% |
| 1-10 | 88.29% | 8.62% | 51.50% | 80.11% | 85.49% |
| 1-11 | 82.28% | 0.03% | 78.50% | 43.16% | 92.99% |
| 1-12 | 43.33% | 0.10% | 38.16% | 56.35% | 88.09% |
| 2-1 | 0.49% | 0.14% | 45.78% | 8.88% | 17.66% |
| 2-2 | 32.24% | 0.13% | 36.09% | 1.25% | 24.55% |
| 2-3 | 48.22% | 35.76% | 45.63% | 38.24% | 64.33% |
| 2-4 | 49.22% | 0.78% | 26.66% | 35.78% | 66.08% |
| 2-5 | 1.11% | 65.66% | 62.58% | 55.66% | 80.10% |
| 2-6 | 37.83% | 41.06% | 6.66% | 25.54% | 78.16% |
| 2-7 | 52.55% | 59.57% | 38.93% | 84.37% | 55.16% |
| 2-8 | 56.80% | 0.86% | 62.42% | 48.30% | 82.57% |
| 2-9 | 0.59% | 80.67% | 51.00% | 64.49% | 85.96% |
| 2-10 | 0.05% | 79.46% | 53.89% | 61.26% | 85.68% |
| 2-11 | 56.80% | 50.98% | 0.75% | 41.21% | 65.12% |
| 2-12 | 28.56% | 0.15% | 49.26% | 39.41% | 38.31% |
| 3-2 | 43.57% | 49.35% | 43.20% | 36.53% | 80.82% |
| 5-3 | 26.24% | 15.25% | 45.03% | 20.39% | 17.11% |
| 5-5 | 1.95% | 13.60% | 19.90% | 40.01% | 12.29% |
| 5-6 | 1.18% | 0.04% | 56.10% | 2.94% | 15.86% |
| 5-7 | 37.04% | 0.22% | 51.90% | 49.43% | 23.85% |
| 5-8 | 17.47% | 31.77% | 26.86% | 12.76% | 18.66% |
| 5-9 | 38.11% | 0.64% | 51.60% | 38.45% | 26.48% |
| 5-10 | 38.54% | 0.32% | 52.78% | 36.60% | 23.79% |
| 6-7 | 86.89% | 83.13% | 74.34% | 72.65% | 89.23% |
| 6-8 | 51.90% | 36.83% | 56.44% | 38.21% | 52.14% |
| 6-9 | 1.38% | 0.48% | 52.25% | 4.93% | 60.56% |
| 6-10 | 0.67% | 0.09% | 51.43% | 4.31% | 56.33% |
| 6-11 | 57.37% | 32.79% | 0.50% | 51.88% | 84.29% |
| 6-12 | 28.81% | 11.47% | 72.37% | 51.57% | 72.63% |
| 7-1 | 48.16% | 0.22% | 53.59% | 52.32% | 86.00% |
| 7-2 | 22.43% | 0.05% | 56.56% | 26.31% | 48.43% |
| 7-3 | 58.13% | 60.11% | 70.26% | 47.15% | 78.31% |
| 7-4 | 73.59% | 0.21% | 72.36% | 47.18% | 8.20% |
| Sensitivity | 73.81 | 57.14 | 97.62 | 80.48 | 92.86 |
| vim bmp3, sep, TFPI2 | | | | 100.00% | |

FIG. 5D

| | Twenty fold dilution | | | | | |
|---|---|---|---|---|---|---|
| | at 97.5% specificity (+2SD of mean) | | | | | |
| | | | | | | |
| Cut off | 2.10% | 0.34% | 3.29% | 4.99% | 7.63% | |
| Adenoma | Vim | BMP3 | Septin9 | TFPI2 | EYA4 | |
| 3-4 | 1.61% | 0.11% | 4.05% | 3.44% | 1.90% | |
| 3-5 | 3.04% | 0.14% | 4.61% | 4.61% | 3.41% | |
| 3-6 | 1.74% | 0.57% | 2.98% | 2.98% | 6.04% | |
| 3-7 | 2.62% | 1.98% | 3.30% | 3.42% | 6.25% | |
| 3-8 | 2.60% | 0.10% | 4.85% | 4.82% | 3.99% | |
| 3-9 | 0.67% | 0.11% | 3.79% | 3.08% | 1.87% | |
| 3-10 | 0.65% | 0.10% | 3.80% | 3.04% | 1.82% | |
| 3-11 | 2.63% | 0.10% | 4.86% | 5.25% | 5.66% | |
| 3-12 | 4.91% | 0.10% | 4.95% | 4.36% | 4.51% | |
| 5-1 | 3.73% | 4.15% | 4.80% | 4.65% | 3.18% | |
| 5-2 | 1.97% | 0.99% | 3.38% | 3.61% | 2.61% | |
| 5-4 | 1.31% | 0.10% | 5.12% | 5.18% | 1.95% | |
| 5-11 | 3.73% | 0.65% | 4.73% | 4.25% | 3.04% | |
| 5-12 | 4.21% | 0.25% | 4.96% | 4.86% | 2.28% | |
| 6-1 | 4.81% | 4.35% | 5.23% | 5.25% | 6.18% | |
| 6-2 | 2.37% | 0.12% | 3.21% | 3.51% | 5.64% | |
| 6-3 | 3.77% | 3.96% | 4.27% | 4.45% | 8.77% | |
| 6-4 | 2.52% | 0.10% | 2.70% | 2.67% | 1.93% | |
| 6-5 | 0.70% | 0.10% | 1.92% | 1.54% | 1.83% | |
| 6-6 | 2.73% | 1.16% | 2.99% | 3.51% | 5.82% | |
| 7-5 | 3.53% | 1.98% | 4.29% | 3.87% | 6.17% | |
| 7-6 | 2.99% | 3.30% | 4.99% | 3.64% | 5.83% | |
| 7-7 | 1.11% | 0.60% | 2.58% | 3.03% | 4.39% | |
| 7-8 | 1.20% | 0.44% | 3.53% | 2.04% | 1.82% | |
| 7-9 | 4.41% | 0.82% | 4.61% | 3.76% | 4.75% | |
| 7-10 | 4.50% | 0.49% | 4.53% | 3.58% | 4.45% | |
| 7-11 | 0.82% | 0.10% | 3.80% | 2.97% | 1.82% | |
| 7-12 | 2.13% | 1.28% | 2.15% | 2.32% | 5.27% | |
| 8-1 | 2.90% | 2.72% | 3.13% | 3.04% | 6.23% | |
| 8-2 | 4.67% | 4.04% | 4.66% | 1.46% | 6.25% | |
| 8-3 | 3.75% | 0.10% | 4.40% | 1.57% | 4.43% | |
| | Sensitivity | | | | | |
| | 67.74 | 54.84 | 74.19 | 6.45 | 0.00 | |
| | | | | | | |
| | v+B+S+TFPI2 | | | 96.77% | | |

FIG. 5E

| | Twenty fold dilution | | | | | |
|---|---|---|---|---|---|---|
| | at 97.5% specificity (+2SD of mean) | | | | | |
| Cancer | Vim | BMP3 | Septin9 | TFPI2 | EYA4 | |
| 1-1 | 3.32% | 0.10% | 4.10% | 4.79% | 6.00% | |
| 1-2 | 1.54% | 0.10% | 3.95% | 4.05% | 6.20% | |
| 1-3 | 0.74% | 0.10% | 4.17% | 4.42% | 6.28% | |
| 1-4 | 3.85% | 0.11% | 3.86% | 3.72% | 5.94% | |
| 1-5 | 4.79% | 4.15% | 4.59% | 4.75% | 6.52% | |
| 1-6 | 4.28% | 3.36% | 4.90% | 4.65% | 6.31% | |
| 1-7 | 0.73% | 0.10% | 3.87% | 2.34% | 1.87% | |
| 1-8 | 0.68% | 0.11% | 2.31% | 2.62% | 2.05% | |
| 1-9 | 5.03% | 0.61% | 5.04% | 5.50% | 6.04% | |
| 1-10 | 5.06% | 0.53% | 5.08% | 5.44% | 6.07% | |
| 1-11 | 4.76% | 0.10% | 4.93% | 3.59% | 6.45% | |
| 1-12 | 2.77% | 0.10% | 2.91% | 4.35% | 6.20% | |
| 2-1 | 0.67% | 0.10% | 3.29% | 1.88% | 2.68% | |
| 2-2 | 1.76% | 0.10% | 2.81% | 1.50% | 3.03% | |
| 2-3 | 3.06% | 1.39% | 3.29% | 3.35% | 5.01% | |
| 2-4 | 3.66% | 0.14% | 2.33% | 3.23% | 5.10% | |
| 2-5 | 0.71% | 3.58% | 4.13% | 4.22% | 5.80% | |
| 2-6 | 3.54% | 3.15% | 1.33% | 2.71% | 5.71% | |
| 2-7 | 3.38% | 2.78% | 2.45% | 3.15% | 4.56% | |
| 2-8 | 3.57% | 0.14% | 4.12% | 3.86% | 4.93% | |
| 2-9 | 0.68% | 4.13% | 3.56% | 4.66% | 6.10% | |
| 2-10 | 0.65% | 4.07% | 3.70% | 4.50% | 6.06% | |
| 2-11 | 3.49% | 3.64% | 1.04% | 3.50% | 5.05% | |
| 2-12 | 2.08% | 0.10% | 3.80% | 3.41% | 1.72% | |
| 5-2 | 2.83% | 2.56% | 3.16% | 3.26% | 5.84% | |
| 5-3 | 1.96% | 0.86% | 3.25% | 2.46% | 2.65% | |
| 5-5 | 0.75% | 0.78% | 2.30% | 3.44% | 2.41% | |
| 5-6 | 0.71% | 0.10% | 3.81% | 1.58% | 2.59% | |
| 5-7 | 2.00% | 0.11% | 3.58% | 3.91% | 2.99% | |
| 5-8 | 1.52% | 1.68% | 2.34% | 2.08% | 2.73% | |
| 5-9 | 3.56% | 0.13% | 3.66% | 3.36% | 3.12% | |
| 5-10 | 3.58% | 0.11% | 3.64% | 3.27% | 3.98% | |
| 6-7 | 4.99% | 4.29% | 4.73% | 5.07% | 6.26% | |
| 6-8 | 3.25% | 1.94% | 3.82% | 3.35% | 4.41% | |
| 6-9 | 0.72% | 0.12% | 3.81% | 1.68% | 4.83% | |
| 6-10 | 0.68% | 0.10% | 3.57% | 1.65% | 4.62% | |
| 6-11 | 3.52% | 1.74% | 1.03% | 4.03% | 6.01% | |
| 6-12 | 2.09% | 0.67% | 4.81% | 4.02% | 5.43% | |
| 7-1 | 3.06% | 0.11% | 3.68% | 4.05% | 6.10% | |
| 7-2 | 1.77% | 0.10% | 3.83% | 2.75% | 4.24% | |
| 7-3 | 3.58% | 3.10% | 4.81% | 3.79% | 5.71% | |
| 7-4 | 4.39% | 0.11% | 4.62% | 3.54% | 2.21% | |
| | | | | | | |
| Sensitivity | | | | | | |
| | 59.52 | 45.24 | 69.05 | 4.76 | 0.00 | |
| | | | | | | |
| vim bmp3, sep, TFPI2 | | | | 97.62% | | |

FIG. 5F

| | Ten Fold dilution at 97.5% specificity (+2SD of mean) | | | | |
|---|---|---|---|---|---|
| Cut off | 2.10% | 0.34% | 5.29% | 4.99% | 7.63% |
| Adenoma | Vim | BMP3 | Septin9 | TFPI2 | EYA4 |
| 3-4 | 2.56% | 0.12% | 7.10% | 5.44% | 2.01% |
| 3-5 | 5.43% | 0.19% | 8.23% | 7.78% | 5.02% |
| 3-6 | 2.84% | 1.05% | 4.96% | 4.53% | 10.28% |
| 3-7 | 4.60% | 3.87% | 5.71% | 5.40% | 10.71% |
| 3-8 | 4.56% | 0.10% | 6.71% | 8.21% | 6.19% |
| 3-9 | 0.69% | 0.12% | 6.58% | 4.72% | 1.94% |
| 3-10 | 0.65% | 0.10% | 6.59% | 4.65% | 1.84% |
| 3-11 | 4.60% | 0.10% | 6.72% | 9.06% | 9.52% |
| 3-12 | 9.16% | 0.10% | 6.90% | 7.29% | 7.23% |
| 5-1 | 6.82% | 8.30% | 6.61% | 7.87% | 4.56% |
| 5-2 | 3.38% | 1.89% | 5.77% | 5.78% | 3.42% |
| 5-4 | 1.78% | 0.10% | 6.25% | 8.52% | 2.11% |
| 5-11 | 6.61% | 1.05% | 6.46% | 7.07% | 4.28% |
| 5-12 | 7.77% | 0.35% | 6.91% | 8.29% | 2.77% |
| 6-1 | 8.96% | 8.60% | 9.45% | 9.07% | 10.56% |
| 6-2 | 4.09% | 0.14% | 5.43% | 5.59% | 9.48% |
| 6-3 | 5.80% | 7.82% | 7.51% | 7.46% | 10.75% |
| 6-4 | 4.39% | 0.10% | 4.41% | 3.90% | 2.05% |
| 6-5 | 0.76% | 0.10% | 2.04% | 1.65% | 1.87% |
| 6-6 | 4.79% | 2.23% | 6.98% | 5.59% | 9.85% |
| 7-5 | 6.41% | 3.86% | 7.55% | 6.30% | 10.55% |
| 7-6 | 4.87% | 6.56% | 7.18% | 5.85% | 9.87% |
| 7-7 | 1.57% | 1.10% | 6.15% | 2.62% | 6.98% |
| 7-8 | 1.76% | 0.79% | 6.06% | 2.64% | 1.83% |
| 7-9 | 6.16% | 1.54% | 6.22% | 6.06% | 7.79% |
| 7-10 | 6.35% | 0.89% | 6.05% | 5.72% | 7.11% |
| 7-11 | 0.99% | 0.10% | 6.20% | 4.50% | 1.84% |
| 7-12 | 3.61% | 2.46% | 5.30% | 3.21% | 8.75% |
| 8-1 | 5.19% | 5.35% | 5.26% | 4.64% | 10.67% |
| 8-2 | 8.69% | 7.98% | 6.32% | 1.47% | 10.70% |
| 8-3 | 6.84% | 0.10% | 7.91% | 1.70% | 7.07% |
| | Sensitivity | | | | |
| | 77.42 | 58.06 | 93.55 | 61.29 | 38.71 |
| | V+B+S+TFPI2 | | | 96.77% | |

FIG. 5G

| Cancer | Ten Fold dilution at 97.5% specificity (+2SD of mean) | | | | |
|---|---|---|---|---|---|
| | Vim | BMP3 | Septin9 | TFPI2 | EYA4 |
| 1-1 | | 0.11% | | | |
| 1-2 | | 0.10% | | | |
| 1-3 | 0.82% | 0.10% | | 7.41% | |
| 1-4 | | 0.13% | | 6.01% | |
| 1-5 | | | | | |
| 1-6 | | | | | |
| 1-7 | 0.82% | 0.10% | | 3.24% | 1.95% |
| 1-8 | 0.71% | 0.12% | | 3.80% | 2.30% |
| 1-9 | | | | | |
| 1-10 | | | | | |
| 1-11 | | 0.10% | | 5.75% | |
| 1-12 | | 0.11% | | 7.27% | |
| 2-1 | 0.70% | 0.11% | | 2.33% | 3.57% |
| 2-2 | | 0.11% | | 1.56% | 4.25% |
| 2-3 | | | | 5.26% | |
| 2-4 | | 0.17% | | 5.01% | |
| 2-5 | 0.76% | | | 7.00% | |
| 2-6 | | | 1.67% | 3.99% | |
| 2-7 | | | | 4.86% | 7.32% |
| 2-8 | | 0.18% | | 6.27% | |
| 2-9 | 0.71% | | | 7.89% | |
| 2-10 | 0.66% | | | 7.56% | |
| 2-11 | | | 1.08% | | |
| 2-12 | | 0.11% | | | |
| 3-2 | | | | | |
| 5-3 | | | | 3.48% | 3.51% |
| 5-5 | 0.84% | | 2.99% | | 3.03% |
| 5-6 | 0.77% | 0.10% | | 1.73% | 3.38% |
| 5-7 | | 0.12% | | | 4.18% |
| 5-8 | | | | 2.71% | 3.67% |
| 5-9 | | 0.16% | | | 4.45% |
| 5-10 | | 0.13% | | | 4.18% |
| 6-7 | | | | 6.70% | |
| 6-8 | | | | 5.26% | 7.01% |
| 6-9 | 0.79% | 0.14% | | 1.93% | |
| 6-10 | 0.72% | 0.11% | | 1.87% | 7.43% |
| 6-11 | | | 1.05% | | |
| 6-12 | | | | | |
| 7-1 | | 0.12% | | 6.67% | |
| 7-2 | | 0.10% | | 4.07% | 6.69% |
| 7-3 | | | | | |
| 7-4 | | 0.12% | | 5.65% | 2.62% |
| Sensitivity | 73.81 | 47.62 | 90.48 | 69.05 | 59.52 |
| vim bmp3, sep, TFPI2 | | | 100.00% | | |

FIG. 5H

| | Five Fold dilution | | | | |
|---|---|---|---|---|---|
| | at 97.5% specificity (+2SD of mean) | | | | |
| Cut off | 2.10% | 0.34% | 3.29% | 4.99% | 7.63% |
| Adenoma | Vim | BMP3 | Septin9 | TFPI2 | EYA4 |
| 3-4 | 4.47% | 0.14% | 13.19% | 9.43% | 2.21% |
| 3-5 | 10.22% | 0.26% | 15.46% | 14.13% | 8.26% |
| 3-6 | 5.02% | 2.00% | 8.92% | 7.61% | 10.75% |
| 3-7 | 8.54% | 7.65% | 10.43% | 9.37% | 13.62% |
| 3-8 | 8.47% | 0.10% | 16.41% | 14.38% | 10.58% |
| 3-9 | 0.73% | 0.15% | 12.15% | 7.99% | 2.08% |
| 3-10 | 0.66% | 0.10% | 12.18% | 7.80% | 1.87% |
| 3-11 | 8.55% | 0.10% | 16.43% | 16.66% | 17.24% |
| 3-12 | 17.66% | 0.10% | 16.80% | 13.14% | 12.65% |
| 5-1 | 12.99% | 16.31% | 16.21% | 14.29% | 7.33% |
| 5-2 | 5.92% | 3.69% | 10.53% | 10.13% | 5.04% |
| 5-4 | 7.90% | 0.10% | 17.49% | 16.40% | 2.42% |
| 5-11 | 12.98% | 3.29% | 15.02% | 12.70% | 6.76% |
| 5-12 | 14.90% | 0.69% | 16.82% | 15.13% | 3.74% |
| 6-1 | 17.27% | 17.11% | 17.90% | 16.70% | 19.33% |
| 6-2 | 7.53% | 0.18% | 9.85% | 9.73% | 17.16% |
| 6-3 | 11.13% | 15.56% | 14.06% | 13.66% | 19.70% |
| 6-4 | 8.14% | 0.11% | 7.81% | 6.36% | 2.30% |
| 6-5 | 0.87% | 0.10% | 3.09% | 1.86% | 1.94% |
| 6-6 | 8.93% | 4.34% | 8.97% | 9.74% | 17.89% |
| 7-5 | 12.18% | 7.62% | 14.11% | 11.17% | 19.30% |
| 7-6 | 8.69% | 13.02% | 13.37% | 10.25% | 17.94% |
| 7-7 | 3.90% | 2.10% | 7.31% | 3.81% | 12.16% |
| 7-8 | 2.86% | 1.49% | 11.12% | 3.83% | 1.87% |
| 7-9 | 15.67% | 7.98% | 15.43% | 10.73% | 13.86% |
| 7-10 | 16.04% | 1.66% | 15.11% | 10.01% | 12.42% |
| 7-11 | 1.33% | 0.11% | 11.41% | 7.55% | 1.88% |
| 7-12 | 6.57% | 4.82% | 5.60% | 4.93% | 15.70% |
| 8-1 | 9.66% | 10.60% | 9.52% | 7.84% | 19.54% |
| 8-2 | 16.74% | 15.87% | 15.83% | 1.51% | 19.60% |
| 8-3 | 13.03% | 0.10% | 14.82% | 1.96% | 12.34% |
| | Sensitivity | | | | |
| | 87.10 | 58.06 | 96.77 | 80.65 | 61.29 |
| | v+B+S+TFPI2 | | 96.77% | | |

FIG. 5I

| Cancer | Vim | BMP3 | Septin9 | TFPI2 | EYA4 |
|---|---|---|---|---|---|
| | Five Fold dilution | | | | |
| | at 97.5% specificity (+2SD of mean) | | | | |
| 1-1 | 7.18% | 0.12% | 13.38% | 14.86% | 18.07% |
| 1-2 | 4.22% | 0.11% | 12.81% | 11.87% | 19.40% |
| 1-3 | 1.00% | 0.10% | 13.67% | 13.38% | 19.72% |
| 1-4 | 13.47% | 0.16% | 12.42% | 10.58% | 18.38% |
| 1-5 | 17.20% | 16.32% | 15.17% | 14.68% | 20.67% |
| 1-6 | 15.17% | 13.16% | 14.60% | 14.31% | 19.85% |
| 1-7 | 0.99% | 0.11% | 11.69% | 5.04% | 2.09% |
| 1-8 | 0.76% | 0.15% | 6.24% | 6.16% | 2.80% |
| 1-9 | 18.18% | 2.15% | 17.14% | 17.68% | 18.78% |
| 1-10 | 18.31% | 1.82% | 17.30% | 17.46% | 18.90% |
| 1-11 | 17.11% | 0.10% | 16.70% | 10.07% | 20.40% |
| 1-12 | 9.12% | 0.12% | 8.63% | 13.11% | 18.41% |
| 2-1 | 0.75% | 0.13% | 10.16% | 3.21% | 5.33% |
| 2-2 | 5.10% | 0.12% | 8.22% | 1.69% | 6.71% |
| 2-3 | 10.29% | 5.25% | 10.13% | 9.08% | 14.65% |
| 2-4 | 8.69% | 0.25% | 6.33% | 8.59% | 15.02% |
| 2-5 | 0.87% | 14.03% | 13.62% | 12.57% | 17.82% |
| 2-6 | 8.22% | 8.31% | 2.33% | 6.55% | 17.43% |
| 2-7 | 11.16% | 10.81% | 6.79% | 8.29% | 12.84% |
| 2-8 | 12.33% | 0.27% | 13.49% | 13.11% | 14.31% |
| 2-9 | 0.77% | 16.23% | 11.20% | 14.33% | 18.99% |
| 2-10 | 0.66% | 15.99% | 11.78% | 13.69% | 18.93% |
| 2-11 | 12.01% | 10.29% | 1.15% | 9.68% | 14.82% |
| 2-12 | 6.96% | 0.13% | 10.65% | 9.32% | 9.30% |
| 3-2 | 8.16% | 8.07% | 9.64% | 8.74% | 17.06% |
| 5-3 | 5.80% | 3.15% | 10.01% | 5.53% | 5.22% |
| 5-5 | 1.04% | 2.82% | 4.38% | 9.44% | 4.26% |
| 5-6 | 0.89% | 0.10% | 12.22% | 2.02% | 4.97% |
| 5-7 | 6.06% | 0.14% | 11.30% | 11.32% | 6.57% |
| 5-8 | 4.14% | 6.44% | 6.38% | 3.99% | 5.53% |
| 5-9 | 8.27% | 0.22% | 11.72% | 9.13% | 7.09% |
| 5-10 | 8.16% | 0.16% | 11.55% | 8.76% | 6.56% |
| 6-7 | 18.05% | 16.72% | 15.87% | 15.97% | 19.64% |
| 6-8 | 11.03% | 7.46% | 12.29% | 9.08% | 12.33% |
| 6-9 | 0.93% | 0.19% | 11.45% | 2.42% | 13.91% |
| 6-10 | 0.78% | 0.12% | 11.29% | 2.30% | 13.07% |
| 6-11 | 12.13% | 6.66% | 1.10% | 11.81% | 18.65% |
| 6-13 | 6.41% | 2.39% | 15.46% | 11.75% | 16.32% |
| 7-1 | 10.28% | 0.14% | 11.72% | 11.46% | 19.06% |
| 7-2 | 5.14% | 0.11% | 13.31% | 6.79% | 11.58% |
| 7-3 | 12.28% | 12.12% | 15.06% | 10.87% | 17.46% |
| 7-4 | 15.37% | 0.14% | 15.47% | 9.87% | 3.44% |
| Sensitivity | 73.81 | 47.62 | 95.24 | 83.33 | 71.43 |
| vim bmp3, sep, TFPI2 | | | 100.00% | | |

DIGITAL SEQUENCE ANALYSIS OF DNA METHYLATION

CROSS-REFERENCE TO RELATED APPLICATIONS

The present application claims the benefit of U.S. Provisional Patent Application Ser. No. 61/438,649, filed Feb. 2, 2011, which is incorporated by reference in its entirety.

FIELD OF THE INVENTION

The present invention relates to methods and compositions for determination of and uses of specific methylation patterns indicative of adenoma and carcinoma. In particular, the invention relates to analysis of defined CpG loci that are coordinately methylated in DNAs from cancer and adenoma samples, methods for identifying coordinately methylated loci, and methods of using analysis of coordinately methylated loci in one or more marker regions in the design of assays for adenoma and cancer having improved sensitivity and specificity.

BACKGROUND OF THE INVENTION

In higher order eukaryotes, DNA may be methylated at cytosines located 5' to guanosine in CpG dinucleotides. This modification has important regulatory effects on gene expression, especially when involving CpG rich areas, known as CpG islands, often found in the promoter regions of genes. While approximately 75% of the CpG sites throughout the human genome are methylated, CpG sites within CpG islands are normally unmethylated, and aberrant methylation of CpG islands has been associated with certain diseases, including cancers. For example, CpG island hypermethylation is associated with transcriptional inactivation of defined tumor suppressor genes in human cancers, e.g., colorectal cancer. Therefore, detection of hypermethylated nucleic acid could indicate susceptibility or onset of various forms of cancers.

Despite indications suggesting a link between CpG island methylator phenotype (CIMP) and cancers (see, e.g., Baylin S B, et al., Adv Cancer Res 1998; 72:141-196 and Jones P A, et al., Nat Rev Genet 2002; 3:415-428), the idea that analysis of methylation status alone could be a useful diagnostic or prognostic tool has been controversial. As discussed by Issa, et al. in an editorial in Gastroenterology 179(3):2005, researchers had mixed results in confirming the link between CI,MP and cancers. Although CIMP was reportedly demonstrated in multiple other malignancies (Shen, I., et al. J Natl Cancer Inst 2002; 94:755-761; Garcia-Manero G, et al., Clin Cancer Res 2002; 8:2217-2224; Toyota M, et al., Blood 2001; 97:2823-2829; Ueki T, et al., Cancer Res 2000;60:1835-1839; Toyota M, et al., Cancer Res 1999; 59:5438-5442; Strathdee G, et al., Am J Pathol 2001; 158:1121-1127; Abe M, et al., Cancer Res 2005; 65:828-834) and several groups confirmed the original findings using similar markers and technology (Whitehall VL, et al., Cancer Res 2002; 62:6011-6014; van Rijnsoever M, et al., Gut 2002; 51:797-802) other groups were not able to establish such links (Eads C A, et al., Cancer Res 2001; 61:3410-3418; Esteller M, et al., Cancer Res 2000; 60:129-133). As late as 2003, a publication concluded that all methylation events in colorectal cancer were related to aging rather than neoplasia (Yamashita K, et al., Cancer Cell 2003; 4:121-131).

The discrepant results have been attributed in part to the fact that it has been demonstrated that 70% to 80% of aberrant DNA methylation events in colorectal cancer are age-related (Toyota M, et al., Proc Natl Acad Sci USA 1999; 96:8681-8686) and that cancer-linked phenotypes are only clear when these are filtered out. It has also been noted that overly sensitive, non-quantitative methods can overestimate methylation and mask the distinctions between methylation that is associated with cancer and that which is not. Issa states that "methylation events (alone) may not provide the ideal universal cancer marker they were once thought to be because CIMP target genes will not be useful to screen for all colorectal cancers (many false negatives are predicted), and non-CIMP target genes will likely yield a high rate of false-positives because they are also methylated in normal appearing mucosa of older individuals without tumors" (Issa, et al., supra).

One approach to increase the clinical specificity of methylation analyses in cancer detection is to look at multiple marker genes. For example, Zou, et al., examined the methylation status of BMP3, EYA2, ALX4, and vimentin in cancer samples. While methylation levels were significantly higher in both cancer and adenoma than in normal epithelium, for each of the four genes, the sensitivity as determined by receiver operating curves was not significantly improved by combining any or all markers compared with the best single marker. (Zou, et al., Cancer Epidemiol Biomarkers Prey 2007; 16(12):2686).

Zou also looked at neoplasims showing methylation in more than one of the marker genes and found that co-methylation was frequent, with 72% of the cancers and 84% of the adenomas tested showing hypermethylation in two or more of the genes. Zou reported that methylation of one or more of four (at least one), two or more of four, three or more of four, or four of four of these marker genes was noted in 88%, 72%, 53%, and 41% of 74 cancers and 98%, 84%, 60%, and 39% of 62 adenomas, compared with 24%, 7%, 3%, and 0% of 70 normal epithelia, respectively, demonstrating that although the assay gets progressively more specific as when more genes are included in the comethylation set, the sensitivity declines precipitously.

SUMMARY OF THE INVENTION

The present invention relates to the methods of identifying regions of specific genes and specific regions of genomic nucleic acid useful in the detection of methylation associated with colorectal cancer. Methods comprise, e.g., detecting methylated sequences in, for example, tissue biopsy, stool extract, or other body fluids with improved sensitivity and specificity. In preferred embodiments, the present invention provides methods of methylation analysis comprising identifying methylation loci showing advantageous methylation ratios when methylation in non-normal cells, e.g., cancer or adenoma cells is compared to background methylation in normal cells. In some embodiments, the present invention relates to methods of analyzing methylation at each of several loci in a set of possible methylation sites within a marker sequence, wherein the presence of methylation at all of the loci within the defined set of sites occurs more frequently in cancer and adenoma cells than in normal cells, such that a finding of methylation at all of the loci in the defined subset of loci in a sample is indicative of adenoma or cancer.

In some embodiments, the present invention provides a method of identifying a set of methylated CpG loci in a marker nucleic acid wherein methylation is indicative of adenoma, comprising:

a) determining the methylation status of a defined set of CpG loci in each of a plurality of individual copies of a marker nucleic acid from a plurality of normal samples;

b) determining the methylation status of said defined set of CpG loci in each of a plurality of individual copies of said marker nucleic acid from a plurality of non-normal (e.g., adenoma or cancer) samples to identify a defined subset of CpG loci from within said defined set, wherein the percentage of individual copies of said marker nucleic acid from said plurality of normal samples that are methylated at all of said CpG loci in said defined subset is less than the percentage of individual copies of said marker nucleic acid from said plurality of non-normal samples that are methylated at all of said CpG loci in said defined subset, and wherein methylation at all of said CpG loci in said defined subset in said marker nucleic acid is indicative of a non-normal state, e.g., adenoma and/or cancer. In certain embodiments, the mean percentage of individual copies of the marker nucleic acid methylated at all loci in said defined set of CpG loci in said plurality of non-normal samples is greater than the mean percentage of individual copies of the marker nucleic acid methylated at all loci in said defined set of CpG loci in the plurality of normal samples. In preferred embodiments, the mean percentage of individual copies of the marker nucleic acid methylated at all loci in said defined set of CpG loci in the plurality of non-normal samples is at least one standard deviation, preferably two standard deviations, more preferably three standard deviations greater than the mean percentage of individual copies of said marker nucleic acid methylated at all loci in said defined set of CpG loci in said plurality of normal samples.

In some embodiments, the defined subset of CpG loci consists of the same loci in the defined set of CpG loci.

Determination of the methylation status of the set of CpG loci may be accomplished by any method known to those of skill in the art. In some embodiments, the method comprises treating DNA from the samples with bisulfite. Bisulfite modification treatment is described, e.g., in U.S. Pat. No. 6,017,704, the entire disclosure of which is incorporated herein by reference. In some embodiments, determining the methylation status of the defined set of CpG loci comprises digital analysis of each of a plurality of CpG loci in a plurality of individual copies of a marker nucleic acid. In some preferred embodiments, digital analysis comprise digital sequencing, and/or digital PCR.

In certain preferred embodiments, non-normal sample comprises an adenoma sample, and in particular preferred embodiments, comprises a colorectal adenoma sample. In some preferred embodiments, a non-normal sampled comprises a cancer sample, and in certain preferred embodiments, comprises a colorectal cancer sample.

The present invention provides methods of detecting cancer or adenoma in a sample, e.g., from a subject. In some embodiments, the present invention provides methods comprising determining the methylation status of each CpG locus in a defined subset of CpG loci in at least one cancer or adenoma marker nucleic acid molecule, wherein methylation at each of the CpG loci in the defined subset of CpG loci in the cancer or adenoma marker nucleic acid molecule is indicative of cancer or adenoma in the sample. In certain preferred embodiments, the defined subset comprises at least three CpG loci, while in some preferred embodiments, the defined subset comprises at least four CpG loci or at least five CpG loci.

In certain embodiments, the determining comprises analysis of the CpG loci in a nucleic acid detection assay configured to determine the methylation status of each of the loci in a single nucleic acid detection assay. In some preferred embodiments, the determining comprises analysis of the CpG loci in a nucleic acid detection assay configured to determine the methylation status of each of said loci in a single reaction mixture. In some embodiments, the nucleic acid detection assay comprises a primer extension assay. In certain preferred embodiments, the nucleic acid detection assay may comprise one or more of a nucleic acid amplification assay, a nucleic acid sequencing assay, a structure-specific cleavage assay, a 5' nuclease cleavage assay, an invasive cleavage assay and/or a ligation assay.

The methods of the present invention are not limited to the analysis of a single cancer or adenoma marker nucleic acid. For example, in some embodiments, the methylation status of each CpG locus in a defined subset of CpG loci in at least one cancer or adenoma marker nucleic acid molecule comprises analysis of nucleic acid molecules from a plurality of cancer or adenoma markers. In some embodiments, the plurality of cancer or adenoma markers comprises at least three cancer or adenoma markers, while in some embodiments, the plurality comprises at least four cancer or adenoma markers. In some preferred embodiments, the cancer or adenoma markers and nucleic acid molecules are selected from the group comprising Vimentin, BMP3, Septin 9, TFPI2, 2 regions of LRAT, and EYA4 markers and nucleic acid molecules. In some embodiments, the assay methods of the present invention are combined with the analysis of one or more other cancer markers, such as fecal occult blood markers (e.g., hemoglobin, alpha-defensin, calprotectin, α1-antitrypsin, albumin, MCM2, transferrin, lactoferrin, and lysozyme).

In certain preferred embodiments of the method described herein, a cancer or adenoma marker nucleic acid molecule comprises a vimentin nucleic acid molecule, and in some particularly preferred embodiments, the defined subset of CpG loci in the vimentin nucleic acid molecule comprises loci 37, 40, and 45.

In certain preferred embodiments of the method described herein, a cancer or adenoma marker nucleic acid molecule comprises a BMP3 nucleic acid molecule, and in some particularly preferred embodiments, the defined subset of CpG loci in the BMP3 nucleic acid molecule comprises loci 34, 53, and 61.

In certain preferred embodiments of the method described herein, a cancer or adenoma marker nucleic acid molecule comprises a Septin9 nucleic acid molecule, and in some particularly preferred embodiments, the defined subset of CpG loci in said Septin9 nucleic acid molecule comprises loci 59, 61, 68, and 70.

In certain preferred embodiments of the method described herein, a cancer or adenoma marker nucleic acid molecule comprises a TFPI2 nucleic acid molecule and in some particularly preferred embodiments, the defined subset of CpG loci in said TFPI2 nucleic acid molecule comprises loci 55, 59, 63, and 67.

In certain preferred embodiments of the method described herein, a cancer or adenoma marker nucleic acid molecule comprises an EYA4 nucleic acid molecule, and in some particularly preferred embodiments, the defined subset of CpG loci in said EYA4 nucleic acid molecule comprises loci 31, 34, 37, and 44.

In certain preferred embodiments of the method described herein, the at least one cancer or adenoma marker or nucleic acid molecule comprises a plurality markers or nucleic acid molecules comprising Vimentin, BMP3, Septin9, and TFPI2 markers or nucleic acid molecules.

The present invention further provides methods of selecting a defined set of CpG loci in a marker nucleic acid wherein methylation is indicative of non-normal status, e.g., adenoma or cancer, comprising a) determining the methylation status of a plurality of CpG loci in each of a plurality of individual copies of a marker nucleic acid from a plurality of normal samples; b) determining the methylation status of the plurality of CpG loci in each of a plurality of individual copies of said marker nucleic acid from a plurality of non-normal (e.g., adenoma or cancer) samples; c) determining methylation ratios for each locus in the plurality of said CpG loci in the marker nucleic acid; and d) selecting a defined set of CpG loci in the marker nucleic acid, wherein the defined set of CpG loci comprises a plurality of CpG loci having advantageous methylation ratios correlating with non-normal status (e.g., adenoma or cancer).

In some embodiments, determining the methylation ratios comprises determining the ratio between the mean methylation at each of the plurality of CpG loci in the normal samples to the mean methylation at each corresponding CpG locus in said plurality of CpG loci in the non-normal samples. In preferred embodiments, the plurality of individual copies of a marker nucleic acid analyzed in the normal and non-normal (e.g., adenoma or cancer) samples comprises at least 10, preferably at least 100, more preferably at least 1000, still more preferably at least 10,000 and still more preferably at least 100,000 copies. The number of copies analyzed is not limited to these whole numbers, but may be any integer above about 10. The number of copies from different sample types, e.g., normal and non-normal need not be equal.

In certain preferred embodiments of the methods of selecting a defined set of CpG loci in a marker nucleic acid described herein, the plurality of normal and non-normal (e.g., adenoma or cancer) samples compared comprises at least 10, preferably at least 25, still more preferably at least 100 samples. The number of samples analyzed in not limited to these whole numbers, but may be any integer above about 10. The number of different samples of the different sample types, e.g., normal and non-normal, need not be equal.

In certain embodiments, the defined set of CpG loci comprises at least three CpG loci, preferably at least four CpG loci, more preferably at least five CpG loci.

Determination of the methylation status of the plurality of CpG loci may be accomplished by any method known to those of skill in the art, including those described in more detail, below. In some embodiments, the method comprises treating DNA from the samples with bisulfite. In some embodiments, determining the methylation status of the defined set of CpG loci comprises digital analysis of each of a plurality of CpG loci in a plurality of individual copies of a marker nucleic acid. In some preferred embodiments, digital analysis comprises digital sequencing, and/or digital PCR. Methods of preparing samples, e.g., stool samples, for analysis are also known in the art. See, e.g., U.S. Pat. Nos. 7,005,266; 6,303,304; 5,741,650; 5,952,178; and 6,268,136, each incorporated herein by reference.

DEFINITIONS

To facilitate an understanding of the present invention, a number of terms and phrases are defined below.

As used herein, the terms "digital sequencing" and "single molecule sequencing" are used interchangeably and refer to determining the nucleotide sequence of individual nucleic acid molecules. Systems for individual molecule sequencing include but are not limited to the 454 FLX™ or 454 TITANIUM™ (Roche), the SOLEXA™/Illumina Genome Analyzer (Illumina), the HELISCOPE™ Single Molecule Sequencer (Helicos Biosciences), and the SOLID™ DNA Sequencer (Life Technologies/Applied Biosystems) instruments), as well as other platforms still under development by companies such as Intelligent Biosystems and Pacific Biosystems.

As used herein, the term "background" as used in reference to methylation of a locus or region refers to methylation observed in a normal cell or sample at a nucleic acid locus or region that is generally unmethylated in normal cells. For example, CpG islands are generally considered unmethylated in normal human cells but methylation is not completely absent in the CpG islands of normal cells.

As used herein, "methylation" or "methylated," as used in reference to the methylation status of a cytosine, e.g., in a CpG locus, generally refers to the presence or absence of a methyl group at position 5 of the cytosine residue (i.e., whether a particular cytosine is 5-methylcytosine). Methylation may be determined directly, e.g., as evidenced by routine methods for analysis of methylation status of cytosines, e.g., by determining the sensitivity (or lack thereof) of a particular C-residue to conversion to uracil by treatment with bisulfite. For example, a cytosine residue in a sample that is not converted to uracil when the sample is treated with bisulfite in a manner that would be expected to convert that residue if non-methylated (e.g., under conditions in which a majority or all of the non-methylated cytosines in the sample are converted to uracils) may generally be deemed "methylated".

As used herein, the terms "digital PCR", "single molecule PCR" and "single molecule amplification" refer to PCR and other nucleic acid amplification methods that are configured to provide amplification product or signal from a single starting molecule. Typically, samples are divided, e.g., by serial dilution or by partition into small enough portions (e.g., in microchambers or in emulsions) such that each portion or dilution has, on average, no more than a single copy of the target nucleic acid. Methods of single molecule PCR are described, e.g., in U.S. Pat. No. 6,143,496, which relates to a method comprising dividing a sample into multiple chambers such that at least one chamber has at least one target, and amplifying the target to determine how many chambers had a target molecule; U.S. Pat. No. 6,391,559; which relates to an assembly for containing and portioning fluid; and U.S. Pat. No. 7,459,315, which relates to a method of dividing a sample into an assembly with sample chambers where the samples are partitioned by surface affinity to the chambers, then sealing the chambers with a curable "displacing fluid." See also U.S. Pat. No. 6,440,706 and U.S. Pat. No. 6,753,147, and Vogelstein, et al., Proc. Natl. Acad. Sci. USA Vol. 96, pp. 9236-9241, August 1999. See also US 20080254474, describing a combination of digital PCR combined with methylation detection.

As used herein, "sensitivity" as used in reference to a diagnostic assay, e.g., a methylation assay, refers to clinical sensitivity—the proportion of positive samples that give a positive result using a diagnostic assay. Sensitivity is generally calculated as the number of true positives identified by the assay, divided by the sum of the number of true positives and the number of false negatives determined by the assay on known positive samples. Similarly, the term "specificity" refers to the proportion or number of true negatives determined by the assay divided by the sum of the number of true negatives and the number of false positives determined by the assay on known negative sample(s).

As used herein in reference to diagnostic or analysis assays, the term "complementary" refers to different assays that, when used together, provide a more sensitive and/or specific result than can be provided by any one of the different assays used alone.

As used herein, the term "informative" or "informativeness" refers to a quality of a marker or panel of markers, and specifically to the likelihood of finding a marker (or panel of markers) in a positive sample.

The term "sample" as used herein is used in its broadest sense. For example, a sample suspected of containing a human gene or chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like.

As used herein, the term "CpG island" refers to a genomic DNA region that contains a high percentage of CpG sites relative to the average genomic CpG incidence (per same species, per same individual, or per subpopulation (e.g., strain, ethnic subpopulation, or the like). Various parameters and definitions for CpG islands exist; for example, in some embodiments, CpG islands are defined as having a GC percentage that is greater than 50% and with an observed/ expected CpG ratio that is greater than 60% (Gardiner-Garden et al. (1987) J Mol. Biol. 196:261-282; Baylin et al. (2006) Nat. Rev. Cancer 6:107-116; Irizarry et al. (2009) Nat. Genetics 41:178-186; each herein incorporated by reference in its entirety). In some embodiments, CpG islands may have a GC content >55% and observed CpG/expected CpG of 0.65 (Takai et al. (2007) PNAS 99:3740-3745; herein incorporated by reference in its entirety). Various parameters also exist regarding the length of CpG islands. As used herein, CpG islands may be less than 100 bp; 100-200 bp, 200-300 bp, 300-500 bp, 500-750 bp; 750-1000 bp; 1000 or more by in length. In some embodiments, CpG islands show altered methylation patterns relative to controls (e.g., altered methylation in cancer subjects relative to subjects without cancer; tissue-specific altered methylation patterns; altered methylation in stool from subjects with colorectal neoplasia (e.g., colorectal cancer, colorectal adenoma) relative to subjects without colorectal neoplasia). In some embodiments, altered methylation involves hypermethylation. In some embodiments, altered methylation involves hypomethylation.

As used herein, the term "CpG shore" or "CpG island shore" refers to a genomic region external to a CpG island that is or that has potential to have altered methylation patterns (see, e.g., Irizarry et al. (2009) Nat. Genetics 41:178-186; herein incorporated by reference in its entirety). CpG island shores may show altered methylation patterns relative to controls (e.g., altered methylation in cancer subjects relative to subjects without cancer; tissue-specific altered methylation patterns; altered methylation in stool from subjects with colorectal neoplasia (e.g., colorectal cancer, colorectal adenoma) relative to subjects without colorectal neoplasia). In some embodiments, altered methylation involves hypermethylation. In some embodiments, altered methylation involves hypomethylation. CpG island shores may be located in various regions relative to CpG islands (see, e.g., Irizarry et al. (2009) Nat. Genetics 41; 178-186; herein incorporated by reference in its entirety). Accordingly, in some embodiments, CpG island shores are located less than 100 bp; 100-250 bp; 250-500 bp; 500-1000 bp; 1000-1500 bp; 1500-2000 bp; 2000-3000 bp; 3000 bp or more away from a CpG island.

The term "target," when used in reference to a nucleic acid detection or analysis method, refers to a nucleic acid having a particular sequence of nucleotides to be detected or analyzed, e.g., in a sample suspected of containing the target nucleic acid. In some embodiments, a target is a nucleic acid having a particular sequence for which it is desirable to determine a methylation status. When used in reference to the polymerase chain reaction, "target" generally refers to the region of nucleic acid bounded by the primers used for polymerase chain reaction. Thus, the "target" is sought to be sorted out from other nucleic acid sequences that may be present in a sample. A "segment" is defined as a region of nucleic acid within the target sequence. The term "sample template" refers to nucleic acid originating from a sample that is analyzed for the presence of a target.

As used herein, the term "locus" refers to a particular position, e.g., of a mutation, polymorphism, or a C residue in a CpG dinucleotide, within a defined region or segment of nucleic acid, such as a gene or any other characterized sequence on a chromosome or RNA molecule. A locus is not limited to any particular size or length, and may refer to a portion of a chromosome, a gene, functional genetic element, or a single nucleotide or basepair. As used herein in reference to CpG sites that may be methylated, a locus refers to the C residue in the CpG dinucleotide.

As used herein, the term "methylation ratio" refers to the amount or degree of methylation observed for particular methylation region or locus (e.g., a CpG locus in a marker gene or region) in a plurality of non-normal cells (e.g., cells in a particular disease state, such as cancerous or precancerous cells) compared to the amount or degree of methylation observed for the same region or locus in a plurality of normal cells (e.g., cells that are not in the particular disease state of interest). For example, for a CpG locus showing mean methylation of 8.39889% in a sampling of normal cells and a mean methylation of 74.0771% in a sampling of a plurality of adenoma cells, a methylation ratio may be expressed as the ratio of the means determined for normal cells:adenoma cells, or 0.11348. A methylation ratio need not be expressed in any particular manner or by any particular calculation. By way of example and not limitation, the methylation ratio above may alternatively be expressed, e.g., as 8.39889:74.0771; 8.39889/74.0771; 74.0771: 8.39889; as a calculated "fold methylation over background" 8.81987, etc.

As used herein, the term "advantageous methylation ratio" refers to a methylation ratio for a locus at which methylation correlates with a cellular status, e.g., a particular disease state (for example, normal, precancerous, cancerous) that, when compared to other methylation loci correlated with the same disease state, displays a higher percentage methylation in a population of non-normal cells compared to background levels of methylation at the same locus in a population of normal cells. In some instances, certain CpG loci e.g., within a methylation marker sequence, display a much greater signal-to-noise, i.e., degree in methylation compared to background than other loci in the same marker sequence. In other instances, certain disease-associated marker genes or regions display advantageous methylation ratios at some or all loci compared to the methylation ratios observed for some or all loci within another marker sequence.

As used herein, the term "coordinately methylated" is used in reference to methylation loci, e.g., CpG loci in a marker sequence, that exhibit a particular pattern of methylation that correlates with a cellular status, e.g., a particular disease state (for example, normal, precancerous, cancerous). In preferred embodiments, methylation loci that are all methylated in a manner correlated with a disease state may be deemed to be coordinately methylated in cells having that disease state. "Coordinate methylation" is not limited to situations in which all of the coordinated loci are methylated. Any pattern of methylation among a particular set of loci that correlates with a cellular status, including patterns in which all of the coordinate loci are methylated, patterns in which the loci exhibit a reproducible pattern of methylation and non-methylation, and patterns in which none of the loci within the set are methylated are all included within the meaning of "coordinately methylated."

As used herein, the term "coordinate methylation analysis" is used interchangeably with "multimethylation analysis" and refers to an assay in which the methylation statuses of a plurality of individual methylation loci in a marker sequence, e.g., CpG loci, are determined together. In preferred embodiments, coordinate methylation analysis is performed using a digital/single copy method (e.g., digital sequencing) or an assay method configured to interrogate all of the selected CpG loci on each molecule tested, such that the methylation pattern in each single molecule tested is revealed.

As used herein, the term "defined set" of CpG loci (or other methylation loci) refers to the set of CpG loci in a marker gene or region selected for methylation analysis. A defined set of CpG loci in a marker gene or region may comprise all CpG loci in the gene or region, or it may comprise fewer than all of the loci in that gene or region.

As used herein the term "defined subset" of CpG loci (or other methylation loci) refers to a subset of the defined set of CpG loci in a marker gene or region, the methylation of which has been determined to be indicative of a non-normal state, e.g., adenoma or cancer. For example, in coordinate methylation analysis to determine the presence of colorectal cancer, the methylation status of a defined subset of CpG loci in at least one cancer marker nucleic acid molecule is determined, with simultaneous methylation at all of said CpG loci in the defined subset being indicative of cancer in the sample. A defined subset of CpG loci in a marker gene or region may comprise all CpG loci in the defined set, or it may comprise fewer than all of the loci in the defined set of loci in that gene or region.

As used herein, the term "colorectal cancer" is meant to include the well-accepted medical definition that defines colorectal cancer as a medical condition characterized by cancer of cells of the intestinal tract below the small intestine (e.g., the large intestine (colon), including the cecum, ascending colon, transverse colon, descending colon, and sigmoid colon, and rectum). Additionally, as used herein, the term "colorectal cancer" is meant to further include medical conditions which are characterized by cancer of cells of the duodenum and small intestine (jejunum and ileum).

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body. As used herein, the term "metastasized colorectal cancer cells" is meant to refer to colorectal cancer cells which have metastasized; colorectal cancer cells localized in a part of the body other than the duodenum, small intestine (jejunum and ileum), large intestine (colon), including the cecum, ascending colon, transverse colon, descending colon, and sigmoid colon, and rectum.

As used herein, "an individual is suspected of being susceptible to metastasized colorectal cancer" is meant to refer to an individual who is at an above-average risk of developing metastasized colorectal cancer. Examples of individuals at a particular risk of developing metastasized colorectal cancer are those whose family medical history indicates above average incidence of colorectal cancer among family members and/or those who have already developed colorectal cancer and have been effectively treated who therefore face a risk of relapse and recurrence. Other factors which may contribute to an above-average risk of developing metastasized colorectal cancer which would thereby lead to the classification of an individual as being suspected of being susceptible to metastasized colorectal cancer may be based upon an individual's specific genetic, medical and/or behavioral background and characteristics.

The term "neoplasm" as used herein refers to any new and abnormal growth of tissue. Thus, a neoplasm can be a premalignant neoplasm or a malignant neoplasm.

The term "neoplasm-specific marker" refers to any biological material that can be used to indicate the presence of a neoplasm. Examples of biological materials include, without limitation, nucleic acids, polypeptides, carbohydrates, fatty acids, cellular components (e.g., cell membranes and mitochondria), and whole cells. In some instances, markers are particular nucleic acid regions, e.g., genes, intragenic regions, etc. Regions of nucleic acid that are markers may be referred to, e.g., as "marker genes," "marker regions," "marker sequences," etc.

The term "colorectal neoplasm-specific marker" refers to any biological material that can be used to indicate the presence of a colorectal neoplasm (e.g., a premalignant colorectal neoplasm; a malignant colorectal neoplasm). Examples of colorectal neoplasm-specific markers include, but are not limited to, exfoliated epithelial markers (e.g., bmp-3, bmp-4, SFRP2, vimentin, septin9, ALX4, EYA4, TFPI2, NDRG4, FOXE1, long DNA, BAT-26, K-ras, APC, melanoma antigen gene, p53, BRAF, and PIK3CA) and fecal occult blood markers (e.g., hemoglobin, alpha-defensin, calprotectin, α1-antitrypsin, albumin, MCM2, transferrin, lactoferrin, and lysozyme). See also U.S. Pat. Nos. 7,485,420; 7,432,050; 5,352,775; 5,648,212; U.S. RE36713; U.S. Pat. Nos. 5,527,676; 5,955,263; 6,090,566; 6,245,515; 6,677,312; 6,800,617; 7,087,583; and 7,267,955, each incorporated herein by reference.

Additional markers include but are not limited those in Table 1, below:

TABLE 1

| Accession | Symbol | GeneID | Reference |
|---|---|---|---|
| NM_000038 | APC | 324 | DNA Methylation And Cancer Therapy, Landes Bioscience 2005, ed. Moshe Szyf |
| NM_000044 | AR | 367 | DNA Methylation And Cancer Therapy, Landes Bioscience 2005, ed. Moshe Szyf |
| AB033043 | KIAA1217 | 56243 | www.methdb.de/ and/or www.mdanderson.org/ |
| AK055404 | KIAA0984 | 23329 | www.methdb.de/ and/or www.mdanderson.org/ |
| AK090480 | | | www.methdb.de/ and/or www.mdanderson.org/ |
| BC041476 | | | www.methdb.de/ and/or www.mdanderson.org/ |
| BX648962 | DKFZp686K1684 | 440034 | www.methdb.de/ and/or www.mdanderson.org/ |
| NM_000017 | ACADS | 35 | www.methdb.de/ and/or www.mdanderson.org/ |
| NM_000022 | ADA | 100; 79015 | www.methdb.de/ and/or www.mdanderson.org/ |
| NM_000038 | APC | 324 | www.methdb.de/ and/or www.mdanderson.org/ |
| NM_000038 | APC | 324 | Weber et al. Nature Genetics 37(8), 2005, 853-862 |
| NM_000043 | FAS | 355; 819114 | Weber et al. Nature Genetics 37(8), 2005, 853-862 |
| NM_000044 | AR | 367 | www.methdb.de/ and/or www.mdanderson.org/ |
| NM_000044 | AR | 367 | Weber et al. Nature Genetics 37(8), 2005, 853-862 |
| NM_000076 | CDKN1C | 1028 | www.methdb.de/ and/or www.mdanderson.org/ |
| NM_000077 | CDKN2A | 1029; 51198 | DNA Methylation And Cancer Therapy, Landes Bioscience 2005, ed. Moshe Szyf |
| NM_000077 | CDKN2A | 1029; 51198 | www.methdb.de/ and/or www.mdanderson.org/ |
| NM_000077 | CDKN2A | 1029; 51198 | Weber et al. Nature Genetics 37(8), 2005, 853-862 |
| NM_000088 | COL1A1 | 1277 | www.methdb.de/ and/or www.mdanderson.org/ |
| NM_000095 | COMP | 1311 | www.methdb.de/ and/or www.mdanderson.org/ |
| NM_000104 | CYP1B1 | 1545 | www.methdb.de/ and/or www.mdanderson.org/ |
| NM_000115 | EDNRB | 1910 | www.methdb.de/ and/or www.mdanderson.org/ |
| NM_000115 | EDNRB | 1910 | Weber et al. Nature Genetics 37(8), 2005, 853-862 |
| NM_000115 | EDNRB | 1910 | www.methdb.de/ and/or www.mdanderson.org/ |
| NM_000125 | ESR1 | 2099 | DNA Methylation And Cancer Therapy, Landes Bioscience 2005, ed. Moshe Szyf |
| NM_000125 | ESR1 | 2099 | DNA Methylation And Cancer Therapy, Landes Bioscience 2005, ed. Moshe Szyf |
| NM_000125 | ESR1 | 2099 | www.methdb.de/ and/or www.mdanderson.org/ |
| NM_000125 | ESR1 | 2099 | Weber et al. Nature Genetics 37(8), 2005, 853-862 |
| NM_000182 | HADHA | 3030 | www.methdb.de/ and/or www.mdanderson.org/ |
| NM_000193 | SHH | 6469 | Keshet et al. Nature Genetics 38(2), 2006, 149-153 |
| NM_000249 | MLH1 | 4292 | DNA Methylation And Cancer Therapy, Landes Bioscience 2005, ed. Moshe Szyf |
| NM_000249 | MLH1 | 4292 | www.methdb.de/ and/or www.mdanderson.org/ |
| NM_000280 | PAX6 | 5080 | www.methdb.de/ and/or www.mdanderson.org/ |
| NM_000280 | PAX6 | 5080 | Keshet et al. Nature Genetics 38(2), 2006, 149-153 |
| NM_000280 | PAX6 | 5080 | Weber et al. Nature Genetics 37(8), 2005, 853-862 |
| NM_000308 | PPGB | 5476 | www.methdb.de/ and/or www.mdanderson.org/ |
| NM_000314 | PTEN | 5728 | DNA Methylation And Cancer Therapy, Landes Bioscience 2005, ed. Moshe Szyf |
| NM_000321 | RB1 | 5925 | DNA Methylation And Cancer Therapy, Landes Bioscience 2005, ed. Moshe Szyf |
| NM_000321 | RB1 | 5925 | www.methdb.de/ and/or www.mdanderson.org/ |
| NM_000336 | SCNN1B | 6338 | www.methdb.de/ and/or www.mdanderson.org/ |
| NM_000362 | TIMP3 | 7078 | DNA Methylation And Cancer Therapy, Landes Bioscience 2005, ed. Moshe Szyf |
| NM_000362 | TIMP3 | 7078 | www.methdb.de/ and/or www.mdanderson.org/ |
| NM_000362 | TIMP3 | 7078 | Weber et al. Nature Genetics 37(8), 2005, 853-862 |
| NM_000378 | WT1 | 7490 | www.methdb.de/ and/or www.mdanderson.org/ |
| NM_000402 | G6PD | 2539 | www.methdb.de/ and/or www.mdanderson.org/ |
| NM_000438 | PAX3 | 5077 | www.methdb.de/ and/or www.mdanderson.org/ |
| NM_000443 | ABCB4 | 5244 | www.methdb.de/ and/or www.mdanderson.org/ |
| NM_000453 | SLC5A5 | 6528 | www.methdb.de/ and/or www.mdanderson.org/ |
| NM_000453 | SLC5A5 | 6528 | www.methdb.de/ and/or www.mdanderson.org/ |
| NM_000475 | NR0B1 | 190 | www.methdb.de/ and/or www.mdanderson.org/ |
| NM_000492 | CFTR | 1080 | www.methdb.de/ and/or www.mdanderson.org/ |
| NM_000492 | CFTR | 1080 | Keshet et al. Nature Genetics 38(2), 2006, 149-153 |
| NM_000514 | GDNF | 2668 | Keshet et al. Nature Genetics 38(2), 2006, 149-153 |
| NM_000517 | HBA2 | 3040 | Keshet et al. Nature Genetics 38(2), 2006, 149-153 |
| NM_000520 | HEXA | 3073; 80072 | Keshet et al. Nature Genetics 38(2), 2006, 149-153 |
| NM_000524 | HTR1A | 3350 | Keshet et al. Nature Genetics 38(2), 2006, 149-153 |
| NM_000551 | VHL | 7428 | DNA Methylation And Cancer Therapy, Landes Bioscience 2005, ed. Moshe Szyf |
| NM_000551 | VHL | 7428 | www.methdb.de/ and/or www.mdanderson.org/ |
| NM_000551 | VHL | 7428 | Weber et al. Nature Genetics 37(8), 2005, 853-862 |
| NM_000610 | CD44 | 960 | Weber et al. Nature Genetics 37(8), 2005, 853-862 |
| NM_000610 | CD44 | 960 | www.methdb.de/ and/or www.mdanderson.org/ |
| NM_000612 | IGF2 | 3481; 492304 | www.methdb.de/ and/or www.mdanderson.org/ |
| NM_000620 | NOS1 | 4842 | Keshet et al. Nature Genetics 38(2), 2006, 149-153 |

TABLE 1-continued

| Accession | Symbol | GeneID | Reference |
|---|---|---|---|
| NM_000680 | ADRA1A | 148 | Keshet et al. Nature Genetics 38(2), 2006, 149-153 |
| NM_000717 | CA4 | 762 | Keshet et al. Nature Genetics 38(2), 2006, 149-153 |
| NM_000721 | CACNA1E | 777 | Keshet et al. Nature Genetics 38(2), 2006, 149-153 |
| NM_000782 | CYP24A1 | 1591 | Keshet et al. Nature Genetics 38(2), 2006, 149-153 |
| NM_000799 | EPO | 2056 | www.methdb.de/ and/or www.mdanderson.org/ |
| NM_000813 | GABRB2 | 2561 | Keshet et al. Nature Genetics 38(2), 2006, 149-153 |
| NM_000818 | GAD2 | 2572 | Keshet et al. Nature Genetics 38(2), 2006, 149-153 |
| NM_000829 | GRIA4 | 2893 | Keshet et al. Nature Genetics 38(2), 2006, 149-153 |
| NM_000830 | GRIK1 | 2897 | Keshet et al. Nature Genetics 38(2), 2006, 149-153 |
| NM_000834 | GRIN2B | 2904 | Keshet et al. Nature Genetics 38(2), 2006, 149-153 |
| NM_000843 | GRM6 | 2916 | Keshet et al. Nature Genetics 38(2), 2006, 149-153 |
| NM_000852 | GSTP1 | 2950 | DNA Methylation And Cancer Therapy, Landes Bioscience 2005, ed. Moshe Szyf |
| NM_000852 | GSTP1 | 2950 | www.methdb.de/ and/or www.mdanderson.org/ |
| NM_000852 | GSTP1 | 2950 | Weber et al. Nature Genetics 37(8), 2005, 853-862 |
| NM_000857 | GUCY1B3 | 2983 | Keshet et al. Nature Genetics 38(2), 2006, 149-153 |
| NM_000863 | HTR1B | 3351 | Keshet et al. Nature Genetics 38(2), 2006, 149-153 |
| NM_000902 | MME | 4311 | www.methdb.de/ and/or www.mdanderson.org/ |
| NM_000914 | OPRM1 | 4988 | Keshet et al. Nature Genetics 38(2), 2006, 149-153 |
| NM_000915 | OXT | 5020 | Keshet et al. Nature Genetics 38(2), 2006, 149-153 |
| NM_000926 | PGR | 5241 | www.methdb.de/ and/or www.mdanderson.org/ |
| NM_000927 | ABCB1 | 5243 | www.methdb.de/ and/or www.mdanderson.org/ |
| NM_000959 | PTGFR | 5737 | Keshet et al. Nature Genetics 38(2), 2006, 149-153 |
| NM_000965 | RARB | 5915 | DNA Methylation And Cancer Therapy, Landes Bioscience 2005, ed. Moshe Szyf |
| NM_000965 | RARB | 5915 | www.methdb.de/ and/or www.mdanderson.org/ |
| NM_000965 | RARB | 5915 | Weber et al. Nature Genetics 37(8), 2005, 853-862 |
| NM_000997 | RPL37 | 6167 | Keshet et al. Nature Genetics 38(2), 2006, 149-153 |
| NM_001001336 | CYB5R2 | 51700 | Keshet et al. Nature Genetics 38(2), 2006, 149-153 |
| NM_001001723 | TMEM1 | 7109 | Keshet et al. Nature Genetics 38(2), 2006, 149-153 |
| NM_001002295 | GATA3 | 2625 | Keshet et al. Nature Genetics 38(2), 2006, 149-153 |
| NM_001003689 | L3MBTL2 | 83746 | Keshet et al. Nature Genetics 38(2), 2006, 149-153 |
| NM_001003891 | PCQAP | 51586 | DNA Methylation And Cancer Therapy, Landes Bioscience 2005, ed. Moshe Szyf |
| NM_001007792 | NTRK1 | 4914 | Keshet et al. Nature Genetics 38(2), 2006, 149-153 |
| NM_001008503 | OPRM1 | 4988 | Keshet et al. Nature Genetics 38(2), 2006, 149-153 |
| NM_001008504 | OPRM1 | 4988 | Keshet et al. Nature Genetics 38(2), 2006, 149-153 |
| NM_001008505 | OPRM1 | 4988 | Keshet et al. Nature Genetics 38(2), 2006, 149-153 |
| NM_001009598 | RXRG | 6258 | Keshet et al. Nature Genetics 38(2), 2006, 149-153 |
| NM_001011545 | BACH1 | 571 | Keshet et al. Nature Genetics 38(2), 2006, 149-153 |
| NM_001012331 | NTRK1 | 4914 | Keshet et al. Nature Genetics 38(2), 2006, 149-153 |
| NM_001013464 | LOC401363 | 401363; 441242; 402532 | www.methdb.de/ and/or www.mdanderson.org/ |
| NM_001018084 | SLC26A10 | 65012 | Keshet et al. Nature Genetics 38(2), 2006, 149-153 |
| NM_001020658 | PUM1 | 9698; 28997 | Keshet et al. Nature Genetics 38(2), 2006, 149-153 |
| NM_001024844 | CD82 | 3732 | www.methdb.de/ and/or www.mdanderson.org/ |
| NM_001025205 | AP2M1 | 1173 | Keshet et al. Nature Genetics 38(2), 2006, 149-153 |
| NM_001025604 | ARRDC2 | 27106 | Keshet et al. Nature Genetics 38(2), 2006, 149-153 |
| NM_001033044 | GLUL | 2752 | Keshet et al. Nature Genetics 38(2), 2006, 149-153 |
| NM_001033056 | GLUL | 2752 | Keshet et al. Nature Genetics 38(2), 2006, 149-153 |
| NM_001033518 | WIPI2 | 26100 | Keshet et al. Nature Genetics 38(2), 2006, 149-153 |
| NM_001033519 | WIPI2 | 26100 | Keshet et al. Nature Genetics 38(2), 2006, 149-153 |
| NM_001033520 | WIPI2 | 26100 | Keshet et al. Nature Genetics 38(2), 2006, 149-153 |
| NM_001033952 | CALCA | 796 | www.methdb.de/ and/or www.mdanderson.org/ |
| NM_001036 | RYR3 | 6263 | Keshet et al. Nature Genetics 38(2), 2006, 149-153 |
| NM_001043 | SLC6A2 | 6530 | Keshet et al. Nature Genetics 38(2), 2006, 149-153 |
| NM_001053 | SSTR5 | 6755 | Keshet et al. Nature Genetics 38(2), 2006, 149-153 |
| NM_001059 | TACR3 | 6870 | Keshet et al. Nature Genetics 38(2), 2006, 149-153 |
| NM_001063 | TF | 7018 | Keshet et al. Nature Genetics 38(2), 2006, 149-153 |
| NM_001100 | ACTA1 | 58 | Keshet et al. Nature Genetics 38(2), 2006, 149-153 |
| NM_001109 | ADAM8 | 101 | Keshet et al. Nature Genetics 38(2), 2006, 149-153 |
| NM_001176 | ARHGDIG | 398 | Keshet et al. Nature Genetics 38(2), 2006, 149-153 |
| NM_001186 | BACH1 | 571 | Keshet et al. Nature Genetics 38(2), 2006, 149-153 |
| NM_001204 | BMPR2 | 659 | Keshet et al. Nature Genetics 38(2), 2006, 149-153 |
| NM_001228 | CASP8 | 841 | www.methdb.de/ and/or www.mdanderson.org/ |
| NM_001250 | CD40 | 958 | Keshet et al. Nature Genetics 38(2), 2006, 149-153 |
| NM_001257 | CDH13 | 1012 | www.methdb.de/ and/or www.mdanderson.org/ |
| NM_001319 | CSNK1G2 | 1455 | Keshet et al. Nature Genetics 38(2), 2006, 149-153 |
| NM_001325 | CSTF2 | 1478 | Keshet et al. Nature Genetics 38(2), 2006, 149-153 |
| NM_001385 | DPYS | 1807; 55412 | Keshet et al. Nature Genetics 38(2), 2006, 149-153 |
| NM_001451 | FOXF1 | 2294 | Keshet et al. Nature Genetics 38(2), 2006, 149-153 |
| NM_001454 | FOXJ1 | 2302 | Keshet et al. Nature Genetics 38(2), 2006, 149-153 |
| NM_001458 | FLNC | 2318 | Keshet et al. Nature Genetics 38(2), 2006, 149-153 |
| NM_001480 | GALR1 | 2587 | Keshet et al. Nature Genetics 38(2), 2006, 149-153 |
| NM_001538 | HSF4 | 3299 | Keshet et al. Nature Genetics 38(2), 2006, 149-153 |

TABLE 1-continued

| Accession | Symbol | GeneID | Reference |
|---|---|---|---|
| NM_001553 | IGFBP7 | 3490; 818325 | www.methdb.de/ and/or www.mdanderson.org/ |
| NM_001572 | IRF7 | 3665 | www.methdb.de/ and/or www.mdanderson.org/ |
| NM_001628 | AKR1B1 | 231 | Keshet et al. Nature Genetics 38(2), 2006, 149-153 |
| NM_001635 | AMPH | 273 | Keshet et al. Nature Genetics 38(2), 2006, 149-153 |
| NM_001651 | AQP5 | 362 | Keshet et al. Nature Genetics 38(2), 2006, 149-153 |
| NM_001718 | BMP6 | 654 | DNA Methylation And Cancer Therapy, Landes Bioscience 2005, ed. Moshe Szyf |
| NM_001753 | CAV1 | 857 | DNA Methylation And Cancer Therapy, Landes Bioscience 2005, ed. Moshe Szyf |
| NM_001753 | CAV1 | 857 | www.methdb.de/ and/or www.mdanderson.org/ |
| NM_001768 | CD8A | 925 | Keshet et al. Nature Genetics 38(2), 2006, 149-153 |
| NM_001801 | CDO1 | 1036 | Keshet et al. Nature Genetics 38(2), 2006, 149-153 |
| NM_001851 | COL9A1 | 1297 | Keshet et al. Nature Genetics 38(2), 2006, 149-153 |
| NM_001883 | CRHR2 | 1395 | Keshet et al. Nature Genetics 38(2), 2006, 149-153 |
| NM_001884 | HAPLN1 | 1404 | Keshet et al. Nature Genetics 38(2), 2006, 149-153 |
| NM_001927 | DES | 1674 | Keshet et al. Nature Genetics 38(2), 2006, 149-153 |
| NM_001954 | DDR1 | 780 | DNA Methylation And Cancer Therapy, Landes Bioscience 2005, ed. Moshe Szyf |
| NM_001958 | EEF1A2 | 1917 | Keshet et al. Nature Genetics 38(2), 2006, 149-153 |
| NM_001972 | ELA2 | 1991 | Keshet et al. Nature Genetics 38(2), 2006, 149-153 |
| NM_001975 | ENO2 | 2026 | Keshet et al. Nature Genetics 38(2), 2006, 149-153 |
| NM_001989 | EVX1 | 2128 | Keshet et al. Nature Genetics 38(2), 2006, 149-153 |
| NM_002007 | FGF4 | 2249 | Keshet et al. Nature Genetics 38(2), 2006, 149-153 |
| NM_002012 | FHIT | 2272; 246734 | www.methdb.de/ and/or www.mdanderson.org/ |
| NM_002024 | FMR1 | 2332 | www.methdb.de/ and/or www.mdanderson.org/ |
| NM_002065 | GLUL | 2752 | Keshet et al. Nature Genetics 38(2), 2006, 149-153 |
| NM_002110 | HCK | 3055 | Keshet et al. Nature Genetics 38(2), 2006, 149-153 |
| NM_002127 | HLA-G | 3135 | Keshet et al. Nature Genetics 38(2), 2006, 149-153 |
| NM_002148 | HOXD10 | 3236 | Keshet et al. Nature Genetics 38(2), 2006, 149-153 |
| NM_002155 | HSPA6 | 3310 | Keshet et al. Nature Genetics 38(2), 2006, 149-153 |
| NM_002191 | INHA | 3623 | DNA Methylation And Cancer Therapy, Landes Bioscience 2005, ed. Moshe Szyf |
| NM_002212 | ITGB4BP | 3692 | Keshet et al. Nature Genetics 38(2), 2006, 149-153 |
| NM_002221 | ITPKB | 3707 | Keshet et al. Nature Genetics 38(2), 2006, 149-153 |
| NM_002235 | KCNA6 | 3742 | Keshet et al. Nature Genetics 38(2), 2006, 149-153 |
| NM_002253 | KDR | 3791 | Keshet et al. Nature Genetics 38(2), 2006, 149-153 |
| NM_002344 | LTK | 4058 | Keshet et al. Nature Genetics 38(2), 2006, 149-153 |
| NM_002412 | MGMT | 4255 | www.methdb.de/ and/or www.mdanderson.org/ |
| NM_002457 | MUC2 | 4583 | www.methdb.de/ and/or www.mdanderson.org/ |
| NM_002478 | MYOD1 | 4654 | www.methdb.de/ and/or www.mdanderson.org/ |
| NM_002529 | NTRK1 | 4914 | Keshet et al. Nature Genetics 38(2), 2006, 149-153 |
| NM_002588 | PCDHGC3 | 5098; 26025; 56108; 56112; 9708; 56109 | Keshet et al. Nature Genetics 38(2), 2006, 149-153 |
| NM_002658 | PLAU | 5328; 414236 | www.methdb.de/ and/or www.mdanderson.org/ |
| NM_002700 | POU4F3 | 5459 | Keshet et al. Nature Genetics 38(2), 2006, 149-153 |
| NM_002807 | PSMD1 | 5707; 7410 | Keshet et al. Nature Genetics 38(2), 2006, 149-153 |
| NM_002848 | PTPRO | 5800 | Keshet et al. Nature Genetics 38(2), 2006, 149-153 |
| NM_002873 | RAD17 | 5884 | Keshet et al. Nature Genetics 38(2), 2006, 149-153 |
| NM_002923 | RGS2 | 5997 | Keshet et al. Nature Genetics 38(2), 2006, 149-153 |
| NM_003027 | SH3GL3 | 6457 | Keshet et al. Nature Genetics 38(2), 2006, 149-153 |
| NM_003088 | FSCN1 | 6624 | Keshet et al. Nature Genetics 38(2), 2006, 149-153 |
| NM_003097 | SNRPN | 6638; 8926; 145624; 8123; 63968; 3653 | www.methdb.de/ and/or www.mdanderson.org/ |
| NM_003149 | STAC | 6769 | Keshet et al. Nature Genetics 38(2), 2006, 149-153 |
| NM_003204 | NFE2L1 | 4779 | Keshet et al. Nature Genetics 38(2), 2006, 149-153 |
| NM_003219 | TERT | 7015 | www.methdb.de/ and/or www.mdanderson.org/ |
| NM_003238 | TGFB2 | 7042 | Keshet et al. Nature Genetics 38(2), 2006, 149-153 |
| NM_003238 | TGFB2 | 7042 | Keshet et al. Nature Genetics 38(2), 2006, 149-153 |
| NM_003246 | THBS1 | 7057 | www.methdb.de/ and/or www.mdanderson.org/ |
| NM_003274 | TMEM1 | 7109 | Keshet et al. Nature Genetics 38(2), 2006, 149-153 |
| NM_003277 | CLDN5 | 7122 | Keshet et al. Nature Genetics 38(2), 2006, 149-153 |
| NM_003295 | TPT1 | 7178; 51447; 2982 | Keshet et al. Nature Genetics 38(2), 2006, 149-153 |
| NM_003300 | TRAF3 | 7187 | Keshet et al. Nature Genetics 38(2), 2006, 149-153 |
| NM_003391 | WNT2 | 7472 | Keshet et al. Nature Genetics 38(2), 2006, 149-153 |
| NM_003392 | WNT5A | 7474 | Keshet et al. Nature Genetics 38(2), 2006, 149-153 |

TABLE 1-continued

| Accession | Symbol | GeneID | Reference |
|---|---|---|---|
| NM_003408 | ZFP37 | 7539; 7551 | Keshet et al. Nature Genetics 38(2), 2006, 149-153 |
| NM_003417 | ZNF264 | 9422 | Keshet et al. Nature Genetics 38(2), 2006, 149-153 |
| NM_003426 | ZNF74 | 7625 | Keshet et al. Nature Genetics 38(2), 2006, 149-153 |
| NM_003435 | ZNF134 | 7693 | Keshet et al. Nature Genetics 38(2), 2006, 149-153 |
| NM_003451 | ZNF177 | 7730 | Keshet et al. Nature Genetics 38(2), 2006, 149-153 |
| NM_003474 | ADAM12 | 8038 | Keshet et al. Nature Genetics 38(2), 2006, 149-153 |
| NM_003508 | FZD9 | 8326 | Keshet et al. Nature Genetics 38(2), 2006, 149-153 |
| NM_003539 | HIST1H4D | 8360 | Keshet et al. Nature Genetics 38(2), 2006, 149-153 |
| NM_003540 | HIST1H4F | 8361 | Keshet et al. Nature Genetics 38(2), 2006, 149-153 |
| NM_003541 | HIST1H4K | 8362 | Keshet et al. Nature Genetics 38(2), 2006, 149-153 |
| NM_003546 | HIST1H4L | 8368 | Keshet et al. Nature Genetics 38(2), 2006, 149-153 |
| NM_003666 | BLZF1 | 8548 | Keshet et al. Nature Genetics 38(2), 2006, 149-153 |
| NM_003735 | PCDHGC3 | 5098; 26025; 56108; 56112; 9708; 56109 | Keshet et al. Nature Genetics 38(2), 2006, 149-153 |
| NM_003736 | PCDHGC3 | 5098; 26025; 56108; 56112; 9708; 56109 | Keshet et al. Nature Genetics 38(2), 2006, 149-153 |
| NM_003775 | EDG6 | 8698 | Keshet et al. Nature Genetics 38(2), 2006, 149-153 |
| NM_003777 | DNAH11 | 8701; 9026 | Keshet et al. Nature Genetics 38(2), 2006, 149-153 |
| NM_003806 | HRK | 8739 | www.methdb.de/ and/or www.mdanderson.org/ |
| NM_003823 | TNFRSF6B | 8771; 51750; 10139 | Keshet et al. Nature Genetics 38(2), 2006, 149-153 |
| NM_003888 | ALDH1A2 | 8854 | Keshet et al. Nature Genetics 38(2), 2006, 149-153 |
| NM_003914 | CCNA1 | 8900 | www.methdb.de/ and/or www.mdanderson.org/ |
| NM_003923 | FOXH1 | 8928 | Keshet et al. Nature Genetics 38(2), 2006, 149-153 |
| NM_003984 | SLC13A2 | 9058 | www.methdb.de/ and/or www.mdanderson.org/ |
| NM_003991 | EDNRB | 1910 | Keshet et al. Nature Genetics 38(2), 2006, 149-153 |
| NM_003999 | OSMR | 9180 | Keshet et al. Nature Genetics 38(2), 2006, 149-153 |
| NM_004004 | GJB2 | 2706 | www.methdb.de/ and/or www.mdanderson.org/ |
| NM_004064 | CDKN1B | 1027 | www.methdb.de/ and/or www.mdanderson.org/ |
| NM_004068 | AP2M1 | 1173 | Keshet et al. Nature Genetics 38(2), 2006, 149-153 |
| NM_004102 | FABP3 | 2170 | www.methdb.de/ and/or www.mdanderson.org/ |
| NM_004113 | FGF12 | 2257 | Keshet et al. Nature Genetics 38(2), 2006, 149-153 |
| NM_004122 | GHSR | 2693 | Keshet et al. Nature Genetics 38(2), 2006, 149-153 |
| NM_004135 | IDH3G | 3421 | Keshet et al. Nature Genetics 38(2), 2006, 149-153 |
| NM_004181 | UCHL1 | 7345 | Keshet et al. Nature Genetics 38(2), 2006, 149-153 |
| NM_004230 | EDG5 | 9294 | Keshet et al. Nature Genetics 38(2), 2006, 149-153 |
| NM_004248 | PRLHR | 2834 | Keshet et al. Nature Genetics 38(2), 2006, 149-153 |
| NM_004267 | CHST2 | 9435 | Keshet et al. Nature Genetics 38(2), 2006, 149-153 |
| NM_004291 | CART | 9607 | Keshet et al. Nature Genetics 38(2), 2006, 149-153 |
| NM_004297 | GNA14 | 9630 | Keshet et al. Nature Genetics 38(2), 2006, 149-153 |
| NM_004327 | BCR | 613; 26226 | www.methdb.de/ and/or www.mdanderson.org/ |
| NM_004360 | CDH1 | 999 | DNA Methylation And Cancer Therapy, Landes Bioscience 2005, ed. Moshe Szyf |
| NM_004360 | CDH1 | 999 | www.methdb.de/ and/or www.mdanderson.org/ |
| NM_004360 | CDH1 | 999 | DNA Methylation And Cancer Therapy, Landes Bioscience 2005, ed. Moshe Szyf |
| NM_004378 | CRABP1 | 1381 | Keshet et al. Nature Genetics 38(2), 2006, 149-153 |
| NM_004385 | CSPG2 | 1462 | www.methdb.de/ and/or www.mdanderson.org/ |
| NM_004387 | NKX2-5 | 1482 | www.methdb.de/ and/or www.mdanderson.org/ |
| NM_004394 | DAP | 1611 | Keshet et al. Nature Genetics 38(2), 2006, 149-153 |
| NM_004411 | DYNC1I1 | 1780 | Keshet et al. Nature Genetics 38(2), 2006, 149-153 |
| NM_004441 | EPHB1 | 2047 | Keshet et al. Nature Genetics 38(2), 2006, 149-153 |
| NM_004464 | FGF5 | 2250 | Keshet et al. Nature Genetics 38(2), 2006, 149-153 |
| NM_004477 | FRG1 | 2483 | Keshet et al. Nature Genetics 38(2), 2006, 149-153 |
| NM_004480 | FUT8 | 2530 | Keshet et al. Nature Genetics 38(2), 2006, 149-153 |
| NM_004484 | GPC3 | 2719 | www.methdb.de/ and/or www.mdanderson.org/ |
| NM_004525 | LRP2 | 4036 | www.methdb.de/ and/or www.mdanderson.org/ |
| NM_004530 | MMP2 | 4313 | Keshet et al. Nature Genetics 38(2), 2006, 149-153 |
| NM_004612 | TGFBR1 | 7046 | www.methdb.de/ and/or www.mdanderson.org/ |
| NM_004621 | TRPC6 | 7225 | Keshet et al. Nature Genetics 38(2), 2006, 149-153 |
| NM_004714 | DYRK1B | 9149 | Keshet et al. Nature Genetics 38(2), 2006, 149-153 |
| NM_004737 | LARGE | 9215 | Keshet et al. Nature Genetics 38(2), 2006, 149-153 |
| NM_004787 | SLIT2 | 9353 | Keshet et al. Nature Genetics 38(2), 2006, 149-153 |
| NM_004817 | TJP2 | 9414 | www.methdb.de/ and/or www.mdanderson.org/ |
| NM_004865 | TBPL1 | 9519 | Keshet et al. Nature Genetics 38(2), 2006, 149-153 |
| NM_004887 | CXCL14 | 9547 | Keshet et al. Nature Genetics 38(2), 2006, 149-153 |
| NM_004929 | CALB1 | 793 | Keshet et al. Nature Genetics 38(2), 2006, 149-153 |
| NM_004936 | CDKN2B | 1030 | DNA Methylation And Cancer Therapy, Landes Bioscience 2005, ed. Moshe Szyf |

TABLE 1-continued

| Accession | Symbol | GeneID | Reference |
|---|---|---|---|
| NM_004936 | CDKN2B | 1030 | www.methdb.de/ and/or www.mdanderson.org/ |
| NM_004938 | DAPK1 | 1612 | DNA Methylation And Cancer Therapy, Landes Bioscience 2005, ed. Moshe Szyf |
| NM_004975 | KCNB1 | 3745 | Keshet et al. Nature Genetics 38(2), 2006, 149-153 |
| NM_004976 | KCNC1 | 3746 | Keshet et al. Nature Genetics 38(2), 2006, 149-153 |
| NM_004988 | MAGEA1 | 4100 | www.methdb.de/ and/or www.mdanderson.org/ |
| NM_005032 | PLS3 | 5358 | www.methdb.de/ and/or www.mdanderson.org/ |
| NM_005048 | PTHR2 | 5746 | Keshet et al. Nature Genetics 38(2), 2006, 149-153 |
| NM_005073 | SLC15A1 | 6564 | Keshet et al. Nature Genetics 38(2), 2006, 149-153 |
| NM_005100 | AKAP12 | 9590 | Keshet et al. Nature Genetics 38(2), 2006, 149-153 |
| NM_005117 | FGF19 | 9965 | www.methdb.de/ and/or www.mdanderson.org/ |
| NM_005117 | FGF19 | 9965 | Keshet et al. Nature Genetics 38(2), 2006, 149-153 |
| NM_005157 | ABL1 | 25 | www.methdb.de/ and/or www.mdanderson.org/ |
| NM_005159 | ACTC | 70 | Keshet et al. Nature Genetics 38(2), 2006, 149-153 |
| NM_005181 | CA3 | 761 | Keshet et al. Nature Genetics 38(2), 2006, 149-153 |
| NM_005233 | EPHA3 | 2042 | www.methdb.de/ and/or www.mdanderson.org/ |
| NM_005284 | GPR6 | 2830 | Keshet et al. Nature Genetics 38(2), 2006, 149-153 |
| NM_005285 | NPBWR1 | 2831 | Keshet et al. Nature Genetics 38(2), 2006, 149-153 |
| NM_005286 | NPBWR2 | 2832 | Keshet et al. Nature Genetics 38(2), 2006, 149-153 |
| NM_005346 | HSPA1B | 3304 | Keshet et al. Nature Genetics 38(2), 2006, 149-153 |
| NM_005382 | NEF3 | 4741 | Keshet et al. Nature Genetics 38(2), 2006, 149-153 |
| NM_005386 | NNAT | 4826 | Keshet et al. Nature Genetics 38(2), 2006, 149-153 |
| NM_005398 | PPP1R3C | 5507 | Keshet et al. Nature Genetics 38(2), 2006, 149-153 |
| NM_005427 | TP73 | 7161 | DNA Methylation And Cancer Therapy, Landes Bioscience 2005, ed. Moshe Szyf |
| NM_005437 | NCOA4 | 8031 | DNA Methylation And Cancer Therapy, Landes Bioscience 2005, ed. Moshe Szyf |
| NM_005523 | HOXA11 | 3207 | Keshet et al. Nature Genetics 38(2), 2006, 149-153 |
| NM_005556 | KRT7 | 3855 | Keshet et al. Nature Genetics 38(2), 2006, 149-153 |
| NM_005584 | MAB21L1 | 4081 | Keshet et al. Nature Genetics 38(2), 2006, 149-153 |
| NM_005638 | SYBL1 | 6845 | www.methdb.de/ and/or www.mdanderson.org/ |
| NM_005668 | ST8SIA4 | 7903 | Keshet et al. Nature Genetics 38(2), 2006, 149-153 |
| NM_005806 | OLIG2 | 10215 | Keshet et al. Nature Genetics 38(2), 2006, 149-153 |
| NM_005825 | RASGRP2 | 10235 | Keshet et al. Nature Genetics 38(2), 2006, 149-153 |
| NM_005946 | MT1A | 4489 | www.methdb.de/ and/or www.mdanderson.org/ |
| NM_005959 | MTNR1B | 4544 | Keshet et al. Nature Genetics 38(2), 2006, 149-153 |
| NM_006000 | TUBA1 | 7277; 84854 | www.methdb.de/ and/or www.mdanderson.org/ |
| NM_006019 | TCIRG1 | 10312 | Keshet et al. Nature Genetics 38(2), 2006, 149-153 |
| NM_006041 | HS3ST3B1 | 9953; 84815 | Keshet et al. Nature Genetics 38(2), 2006, 149-153 |
| NM_006043 | HS3ST2 | 9956 | Keshet et al. Nature Genetics 38(2), 2006, 149-153 |
| NM_006053 | TCIRG1 | 10312 | Keshet et al. Nature Genetics 38(2), 2006, 149-153 |
| NM_006142 | SFN | 2810 | www.methdb.de/ and/or www.mdanderson.org/ |
| NM_006158 | NEFL | 4747 | Keshet et al. Nature Genetics 38(2), 2006, 149-153 |
| NM_006158 | NEFL | 4747 | www.methdb.de/ and/or www.mdanderson.org/ |
| NM_006161 | NEUROG1 | 4762 | Keshet et al. Nature Genetics 38(2), 2006, 149-153 |
| NM_006194 | PAX9 | 5083 | Keshet et al. Nature Genetics 38(2), 2006, 149-153 |
| NM_006211 | PENK | 5179 | Keshet et al. Nature Genetics 38(2), 2006, 149-153 |
| NM_006306 | SMC1L1 | 8243 | Keshet et al. Nature Genetics 38(2), 2006, 149-153 |
| NM_006307 | SRPX | 8406 | Keshet et al. Nature Genetics 38(2), 2006, 149-153 |
| NM_006463 | STAMBP | 10617 | Keshet et al. Nature Genetics 38(2), 2006, 149-153 |
| NM_006483 | DYRK1B | 9149 | Keshet et al. Nature Genetics 38(2), 2006, 149-153 |
| NM_006484 | DYRK1B | 9149 | Keshet et al. Nature Genetics 38(2), 2006, 149-153 |
| NM_006497 | HIC1 | 3090 | DNA Methylation And Cancer Therapy, Landes Bioscience 2005, ed. Moshe Szyf |
| NM_006497 | HIC1 | 3090 | www.methdb.de/ and/or www.mdanderson.org/ |
| NM_006539 | CACNG3 | 10368 | Keshet et al. Nature Genetics 38(2), 2006, 149-153 |
| NM_006587 | CORIN | 10699 | Keshet et al. Nature Genetics 38(2), 2006, 149-153 |
| NM_006614 | CHL1 | 10752 | Keshet et al. Nature Genetics 38(2), 2006, 149-153 |
| NM_006735 | HOXA2 | 3199 | Keshet et al. Nature Genetics 38(2), 2006, 149-153 |
| NM_006765 | TUSC3 | 7991 | www.methdb.de/ and/or www.mdanderson.org/ |
| NM_006788 | RALBP1 | 10928 | Keshet et al. Nature Genetics 38(2), 2006, 149-153 |
| NM_006874 | ELF2 | 1998; 26472 | Keshet et al. Nature Genetics 38(2), 2006, 149-153 |
| NM_006898 | HOXD3 | 3232 | Keshet et al. Nature Genetics 38(2), 2006, 149-153 |
| NM_006917 | RXRG | 6258 | Keshet et al. Nature Genetics 38(2), 2006, 149-153 |
| NM_007117 | TRH | 7200 | Keshet et al. Nature Genetics 38(2), 2006, 149-153 |
| NM_007181 | MAP4K1 | 11184 | Keshet et al. Nature Genetics 38(2), 2006, 149-153 |
| NM_007182 | RASSF1 | 11186 | DNA Methylation And Cancer Therapy, Landes Bioscience 2005, ed. Moshe Szyf |
| NM_007182 | RASSF1 | 11186 | DNA Methylation And Cancer Therapy, Landes Bioscience 2005, ed. Moshe Szyf |
| NM_007182 | RASSF1 | 11186 | www.methdb.de/ and/or www.mdanderson.org/ |
| NM_007197 | FZD10 | 11211 | Keshet et al. Nature Genetics 38(2), 2006, 149-153 |
| NM_007294 | BRCA1 | 672 | DNA Methylation And Cancer Therapy, Landes Bioscience 2005, ed. Moshe Szyf |
| NM_007294 | BRCA1 | 672 | www.methdb.de/ and/or www.mdanderson.org/ |

TABLE 1-continued

| Accession | Symbol | GeneID | Reference |
|---|---|---|---|
| NM_007332 | TRPA1 | 8989 | Keshet et al. Nature Genetics 38(2), 2006, 149-153 |
| NM_007345 | ZNF236 | 7776 | Keshet et al. Nature Genetics 38(2), 2006, 149-153 |
| NM_007361 | NID2 | 22795 | Keshet et al. Nature Genetics 38(2), 2006, 149-153 |
| NM_012200 | B3GAT3 | 26229 | Keshet et al. Nature Genetics 38(2), 2006, 149-153 |
| NM_012202 | GNG3 | 2785 | Keshet et al. Nature Genetics 38(2), 2006, 149-153 |
| NM_012261 | C20orf103 | 24141 | Keshet et al. Nature Genetics 38(2), 2006, 149-153 |
| NM_012295 | CABIN1 | 23523 | www.methdb.de/ and/or www.mdanderson.org/ |
| NM_012295 | CABIN1 | 23523 | Keshet et al. Nature Genetics 38(2), 2006, 149-153 |
| NM_012301 | MAGI2 | 9863 | Keshet et al. Nature Genetics 38(2), 2006, 149-153 |
| NM_012309 | SHANK2 | 22941 | www.methdb.de/ and/or www.mdanderson.org/ |
| NM_012309 | SHANK2 | 22941 | Keshet et al. Nature Genetics 38(2), 2006, 149-153 |
| NM_012399 | PITPNB | 23760 | Keshet et al. Nature Genetics 38(2), 2006, 149-153 |
| NM_012444 | SPO11 | 23626 | Keshet et al. Nature Genetics 38(2), 2006, 149-153 |
| NM_012458 | TIMM13 | 26517 | Keshet et al. Nature Genetics 38(2), 2006, 149-153 |
| NM_013250 | ZNF215 | 7762 | Keshet et al. Nature Genetics 38(2), 2006, 149-153 |
| NM_013291 | CPSF1 | 29894 | Keshet et al. Nature Genetics 38(2), 2006, 149-153 |
| NM_013381 | TRHDE | 29953 | Keshet et al. Nature Genetics 38(2), 2006, 149-153 |
| NM_013435 | RAX | 30062 | Keshet et al. Nature Genetics 38(2), 2006, 149-153 |
| NM_013942 | PAX3 | 5077 | Keshet et al. Nature Genetics 38(2), 2006, 149-153 |
| NM_014020 | LR8 | 28959 | Keshet et al. Nature Genetics 38(2), 2006, 149-153 |
| NM_014080 | DUOX2 | 50506 | Keshet et al. Nature Genetics 38(2), 2006, 149-153 |
| NM_014155 | BTBD15 | 29068 | Keshet et al. Nature Genetics 38(2), 2006, 149-153 |
| NM_014228 | SLC6A7 | 6534 | Keshet et al. Nature Genetics 38(2), 2006, 149-153 |
| NM_014234 | HSD17B8 | 7923 | Keshet et al. Nature Genetics 38(2), 2006, 149-153 |
| NM_014325 | CORO1C | 23603 | Keshet et al. Nature Genetics 38(2), 2006, 149-153 |
| NM_014379 | KCNV1 | 27012 | Keshet et al. Nature Genetics 38(2), 2006, 149-153 |
| NM_014386 | PKD2L2 | 27039 | Keshet et al. Nature Genetics 38(2), 2006, 149-153 |
| NM_014459 | PCDH17 | 27253; 144997 | Keshet et al. Nature Genetics 38(2), 2006, 149-153 |
| NM_014468 | VENTX | 27287 | Keshet et al. Nature Genetics 38(2), 2006, 149-153 |
| NM_014522 | PCDH11X | 27328; 83259 | Keshet et al. Nature Genetics 38(2), 2006, 149-153 |
| NM_014574 | STRN3 | 29966 | Keshet et al. Nature Genetics 38(2), 2006, 149-153 |
| NM_014587 | SOX8 | 30812 | Keshet et al. Nature Genetics 38(2), 2006, 149-153 |
| NM_014588 | VSX1 | 30813 | Keshet et al. Nature Genetics 38(2), 2006, 149-153 |
| NM_014618 | DBC1 | 1620 | Keshet et al. Nature Genetics 38(2), 2006, 149-153 |
| NM_014618 | DBC1 | 1620 | DNA Methylation And Cancer Therapy, Landes Bioscience 2005, ed. Moshe Szyf |
| NM_014631 | SH3PXD2A | 9644 | Keshet et al. Nature Genetics 38(2), 2006, 149-153 |
| NM_014653 | KIAA0789 | 9671 | Keshet et al. Nature Genetics 38(2), 2006, 149-153 |
| NM_014676 | PUM1 | 9698; 28997 | Keshet et al. Nature Genetics 38(2), 2006, 149-153 |
| NM_014710 | GPRASP1 | 9737 | Keshet et al. Nature Genetics 38(2), 2006, 149-153 |
| NM_014724 | ZNF96 | 9753 | Keshet et al. Nature Genetics 38(2), 2006, 149-153 |
| NM_014786 | ARHGEF17 | 9828 | Keshet et al. Nature Genetics 38(2), 2006, 149-153 |
| NM_014817 | KIAA0644 | 9865 | Keshet et al. Nature Genetics 38(2), 2006, 149-153 |
| NM_014979 | SV2C | 22987 | www.methdb.de/ and/or www.mdanderson.org/ |
| NM_015002 | FBXO21 | 23014 | Keshet et al. Nature Genetics 38(2), 2006, 149-153 |
| NM_015094 | HIC2 | 23119 | www.methdb.de/ and/or www.mdanderson.org/ |
| NM_015101 | GLT25D2 | 23127 | Keshet et al. Nature Genetics 38(2), 2006, 149-153 |
| NM_015163 | TRIM9 | 114088 | Keshet et al. Nature Genetics 38(2), 2006, 149-153 |
| NM_015472 | WWTR1 | 25937 | Keshet et al. Nature Genetics 38(2), 2006, 149-153 |
| NM_015507 | EGFL6 | 25975 | Keshet et al. Nature Genetics 38(2), 2006, 149-153 |
| NM_015610 | WIPI2 | 26100 | Keshet et al. Nature Genetics 38(2), 2006, 149-153 |
| NM_015641 | TES | 26136 | www.methdb.de/ and/or www.mdanderson.org/ |
| NM_015683 | ARRDC2 | 27106 | Keshet et al. Nature Genetics 38(2), 2006, 149-153 |
| NM_015722 | DRD1IP | 50632 | Keshet et al. Nature Genetics 38(2), 2006, 149-153 |
| NM_015920 | RPS27L | 51065 | Keshet et al. Nature Genetics 38(2), 2006, 149-153 |
| NM_016003 | WIPI2 | 26100 | Keshet et al. Nature Genetics 38(2), 2006, 149-153 |
| NM_016135 | ETV7 | 51513 | Keshet et al. Nature Genetics 38(2), 2006, 149-153 |
| NM_016157 | TRO | 7216 | Keshet et al. Nature Genetics 38(2), 2006, 149-153 |
| NM_016162 | ING4 | 51147 | Keshet et al. Nature Genetics 38(2), 2006, 149-153 |
| NM_016179 | TRPC4 | 7223 | Keshet et al. Nature Genetics 38(2), 2006, 149-153 |
| NM_016192 | TMEFF2 | 23671 | Keshet et al. Nature Genetics 38(2), 2006, 149-153 |
| NM_016192 | TMEFF2 | 23671 | www.methdb.de/ and/or www.mdanderson.org/ |
| NM_016223 | PACSIN3 | 29763 | Keshet et al. Nature Genetics 38(2), 2006, 149-153 |
| NM_016229 | CYB5R2 | 51700 | Keshet et al. Nature Genetics 38(2), 2006, 149-153 |
| NM_016301 | ATPBD1C | 51184 | Keshet et al. Nature Genetics 38(2), 2006, 149-153 |
| NM_016442 | ARTS-1 | 51752 | Keshet et al. Nature Genetics 38(2), 2006, 149-153 |
| NM_016521 | TFDP3 | 51270 | Keshet et al. Nature Genetics 38(2), 2006, 149-153 |
| NM_016535 | ZNF581 | 51545 | Keshet et al. Nature Genetics 38(2), 2006, 149-153 |
| NM_016538 | SIRT7 | 51547 | Keshet et al. Nature Genetics 38(2), 2006, 149-153 |
| NM_016540 | GPR83 | 10888 | Keshet et al. Nature Genetics 38(2), 2006, 149-153 |
| NM_016552 | ANKMY1 | 51281 | Keshet et al. Nature Genetics 38(2), 2006, 149-153 |
| NM_016568 | RLN3R1 | 51289 | Keshet et al. Nature Genetics 38(2), 2006, 149-153 |
| NM_016605 | FAM53C | 51307; 995 | Keshet et al. Nature Genetics 38(2), 2006, 149-153 |
| NM_016931 | NOX4 | 50507 | Keshet et al. Nature Genetics 38(2), 2006, 149-153 |
| NM_016950 | SPOCK3 | 50859 | Keshet et al. Nature Genetics 38(2), 2006, 149-153 |

TABLE 1-continued

| Accession | Symbol | GeneID | Reference |
|---|---|---|---|
| NM_016954 | TBX22 | 50945 | Keshet et al. Nature Genetics 38(2), 2006, 149-153 |
| NM_017514 | PLXNA3 | 55558 | Keshet et al. Nature Genetics 38(2), 2006, 149-153 |
| NM_017649 | CNNM2 | 54805 | Keshet et al. Nature Genetics 38(2), 2006, 149-153 |
| NM_017729 | EPS8L1 | 54869 | Keshet et al. Nature Genetics 38(2), 2006, 149-153 |
| NM_017798 | YTHDF1 | 54915 | Keshet et al. Nature Genetics 38(2), 2006, 149-153 |
| NM_017844 | ANKMY1 | 51281 | Keshet et al. Nature Genetics 38(2), 2006, 149-153 |
| NM_017847 | C1orf27 | 54953 | Keshet et al. Nature Genetics 38(2), 2006, 149-153 |
| NM_018061 | PRPF38B | 55119 | Keshet et al. Nature Genetics 38(2), 2006, 149-153 |
| NM_018074 | FLJ10374 | 55702 | Keshet et al. Nature Genetics 38(2), 2006, 149-153 |
| NM_018129 | PNPO | 55163 | Keshet et al. Nature Genetics 38(2), 2006, 149-153 |
| NM_018135 | MRPS18A | 55168 | Keshet et al. Nature Genetics 38(2), 2006, 149-153 |
| NM_018197 | ZFP64 | 55734 | Keshet et al. Nature Genetics 38(2), 2006, 149-153 |
| NM_018310 | BRF2 | 55290 | Keshet et al. Nature Genetics 38(2), 2006, 149-153 |
| NM_018354 | C20orf46 | 55321 | Keshet et al. Nature Genetics 38(2), 2006, 149-153 |
| NM_018401 | STK32B | 55351 | Keshet et al. Nature Genetics 38(2), 2006, 149-153 |
| NM_018431 | DOK5 | 55816 | Keshet et al. Nature Genetics 38(2), 2006, 149-153 |
| NM_018898 | PCDHA6 | 56142; 56145; 56134; 56147; 56146; 56139 | Keshet et al. Nature Genetics 38(2), 2006, 149-153 |
| NM_018899 | PCDHA6 | 56142; 56145; 56134; 56147; 56146; 56139 | Keshet et al. Nature Genetics 38(2), 2006, 149-153 |
| NM_018901 | PCDHA6 | 56142; 56145; 56134; 56147; 56146; 56139 | Keshet et al. Nature Genetics 38(2), 2006, 149-153 |
| NM_018906 | PCDHA6 | 56142; 56145; 56134; 56147; 56146; 56139 | Keshet et al. Nature Genetics 38(2), 2006, 149-153 |
| NM_018911 | PCDHA6 | 56142; 56145; 56134; 56147; 56146; 56139 | Keshet et al. Nature Genetics 38(2), 2006, 149-153 |
| NM_018920 | PCDHGC3 | 5098; 26025; 56108; 56112; 9708; 56109 | Keshet et al. Nature Genetics 38(2), 2006, 149-153 |
| NM_018925 | PCDHGC3 | 5098; 26025; 56108; 56112; 9708; 56109 | Keshet et al. Nature Genetics 38(2), 2006, 149-153 |
| NM_018926 | PCDHGC3 | 5098; 26025; 56108; 56112; 9708; 56109 | Keshet et al. Nature Genetics 38(2), 2006, 149-153 |
| NM_018927 | PCDHGC3 | 5098; 26025; 56108; 56112; 9708; 56109 | Keshet et al. Nature Genetics 38(2), 2006, 149-153 |
| NM_018928 | PCDHGC3 | 5098; 26025; 56108; 56112; 9708; 56109 | Keshet et al. Nature Genetics 38(2), 2006, 149-153 |
| NM_018950 | HLA-F | 3134 | Keshet et al. Nature Genetics 38(2), 2006, 149-153 |
| NM_018976 | SLC38A2 | 54407 | Keshet et al. Nature Genetics 38(2), 2006, 149-153 |

TABLE 1-continued

| Accession | Symbol | GeneID | Reference |
|---|---|---|---|
| NM_018997 | MRPS21 | 54460 | Keshet et al. Nature Genetics 38(2), 2006, 149-153 |
| NM_019043 | APBB1IP | 54518 | Keshet et al. Nature Genetics 38(2), 2006, 149-153 |
| NM_019102 | HOXA5 | 3202 | www.methdb.de/ and/or www.mdanderson.org/ |
| NM_020166 | MCCC1 | 56922 | Keshet et al. Nature Genetics 38(2), 2006, 149-153 |
| NM_020201 | NT5M | 56953 | Keshet et al. Nature Genetics 38(2), 2006, 149-153 |
| NM_020208 | SLC6A20 | 54716 | Keshet et al. Nature Genetics 38(2), 2006, 149-153 |
| NM_020226 | PRDM8 | 56978 | Keshet et al. Nature Genetics 38(2), 2006, 149-153 |
| NM_020230 | PPAN | 56342 | Keshet et al. Nature Genetics 38(2), 2006, 149-153 |
| NM_020348 | CNNM1 | 26507 | Keshet et al. Nature Genetics 38(2), 2006, 149-153 |
| NM_020469 | ABO | 28 | www.methdb.de/ and/or www.mdanderson.org/ |
| NM_020549 | CHAT | 1103 | Keshet et al. Nature Genetics 38(2), 2006, 149-153 |
| NM_020630 | RET | 5979 | www.methdb.de/ and/or www.mdanderson.org/ |
| NM_020650 | RCN3 | 57333 | Keshet et al. Nature Genetics 38(2), 2006, 149-153 |
| NM_020657 | ZNF304 | 57343 | Keshet et al. Nature Genetics 38(2), 2006, 149-153 |
| NM_020660 | CX36 | 57369 | Keshet et al. Nature Genetics 38(2), 2006, 149-153 |
| NM_020685 | C3orf14 | 57415 | Keshet et al. Nature Genetics 38(2), 2006, 149-153 |
| NM_020815 | PCDH10 | 57575 | Keshet et al. Nature Genetics 38(2), 2006, 149-153 |
| NM_020873 | LRRN1 | 57633 | www.methdb.de/ and/or www.mdanderson.org/ |
| NM_020984 | CHAT | 1103 | Keshet et al. Nature Genetics 38(2), 2006, 149-153 |
| NM_020985 | CHAT | 1103 | Keshet et al. Nature Genetics 38(2), 2006, 149-153 |
| NM_020986 | CHAT | 1103 | Keshet et al. Nature Genetics 38(2), 2006, 149-153 |
| NM_020999 | NEUROG3 | 50674 | Keshet et al. Nature Genetics 38(2), 2006, 149-153 |
| NM_021032 | FGF12 | 2257 | Keshet et al. Nature Genetics 38(2), 2006, 149-153 |
| NM_021101 | CLDN1 | 9076 | Keshet et al. Nature Genetics 38(2), 2006, 149-153 |
| NM_021179 | C1orf114 | 57821 | Keshet et al. Nature Genetics 38(2), 2006, 149-153 |
| NM_021193 | HOXD12 | 3238 | Keshet et al. Nature Genetics 38(2), 2006, 149-153 |
| NM_021216 | ZNF71 | 58491 | Keshet et al. Nature Genetics 38(2), 2006, 149-153 |
| NM_021257 | NGB | 58157 | Keshet et al. Nature Genetics 38(2), 2006, 149-153 |
| NM_021614 | KCNN2 | 3781 | Keshet et al. Nature Genetics 38(2), 2006, 149-153 |
| NM_021911 | GABRB2 | 2561 | Keshet et al. Nature Genetics 38(2), 2006, 149-153 |
| NM_021926 | ALX4 | 60529 | Keshet et al. Nature Genetics 38(2), 2006, 149-153 |
| NM_021956 | GRIK2 | 2898 | Keshet et al. Nature Genetics 38(2), 2006, 149-153 |
| NM_022076 | DUSP21 | 63904 | Keshet et al. Nature Genetics 38(2), 2006, 149-153 |
| NM_022088 | ZFP64 | 55734 | Keshet et al. Nature Genetics 38(2), 2006, 149-153 |
| NM_022169 | ABCG4 | 64137 | Keshet et al. Nature Genetics 38(2), 2006, 149-153 |
| NM_022405 | SLC6A20 | 54716 | Keshet et al. Nature Genetics 38(2), 2006, 149-153 |
| NM_022443 | MLF1 | 4291 | Keshet et al. Nature Genetics 38(2), 2006, 149-153 |
| NM_022468 | MMP25 | 64386; 4328 | Keshet et al. Nature Genetics 38(2), 2006, 149-153 |
| NM_022469 | GREM2 | 64388 | Keshet et al. Nature Genetics 38(2), 2006, 149-153 |
| NM_022718 | MMP25 | 64386; 4328 | Keshet et al. Nature Genetics 38(2), 2006, 149-153 |
| NM_022750 | PARP12 | 64761 | Keshet et al. Nature Genetics 38(2), 2006, 149-153 |
| NM_023926 | ZNF447 | 65982 | Keshet et al. Nature Genetics 38(2), 2006, 149-153 |
| NM_024012 | HTR5A | 3361 | Keshet et al. Nature Genetics 38(2), 2006, 149-153 |
| NM_024046 | CAMKV | 79012 | Keshet et al. Nature Genetics 38(2), 2006, 149-153 |
| NM_024101 | MLPH | 79083 | Keshet et al. Nature Genetics 38(2), 2006, 149-153 |
| NM_024306 | FA2H | 79152 | Keshet et al. Nature Genetics 38(2), 2006, 149-153 |
| NM_024409 | NPPC | 4880 | Keshet et al. Nature Genetics 38(2), 2006, 149-153 |
| NM_024504 | PRDM14 | 63978 | Keshet et al. Nature Genetics 38(2), 2006, 149-153 |
| NM_024593 | EFCAB1 | 79645 | Keshet et al. Nature Genetics 38(2), 2006, 149-153 |
| NM_024600 | C16orf30 | 79652 | Keshet et al. Nature Genetics 38(2), 2006, 149-153 |
| NM_024826 | ASAP | 79884 | Keshet et al. Nature Genetics 38(2), 2006, 149-153 |
| NM_024882 | C6orf155 | 79940 | Keshet et al. Nature Genetics 38(2), 2006, 149-153 |
| NM_024893 | C20orf39 | 79953 | Keshet et al. Nature Genetics 38(2), 2006, 149-153 |
| NM_024944 | CHODL | 140578 | Keshet et al. Nature Genetics 38(2), 2006, 149-153 |
| NM_025019 | TUBA4 | 80086 | Keshet et al. Nature Genetics 38(2), 2006, 149-153 |
| NM_025058 | TRIM46 | 80128 | Keshet et al. Nature Genetics 38(2), 2006, 149-153 |
| NM_025061 | LRRC8E | 80131 | Keshet et al. Nature Genetics 38(2), 2006, 149-153 |
| NM_025087 | FLJ21511 | 80157 | Keshet et al. Nature Genetics 38(2), 2006, 149-153 |
| NM_025197 | CDK5RAP3 | 80279 | Keshet et al. Nature Genetics 38(2), 2006, 149-153 |
| NM_025204 | RP3-402G11.12 | 80305 | Keshet et al. Nature Genetics 38(2), 2006, 149-153 |
| NM_025208 | PDGFD | 80310; 414301 | Keshet et al. Nature Genetics 38(2), 2006, 149-153 |
| NM_025218 | ULBP1 | 80329 | Keshet et al. Nature Genetics 38(2), 2006, 149-153 |
| NM_025263 | PRR3 | 80742 | Keshet et al. Nature Genetics 38(2), 2006, 149-153 |
| NM_030577 | MGC10993 | 80775 | Keshet et al. Nature Genetics 38(2), 2006, 149-153 |
| NM_030667 | PTPRO | 5800 | Keshet et al. Nature Genetics 38(2), 2006, 149-153 |
| NM_030668 | PTPRO | 5800 | Keshet et al. Nature Genetics 38(2), 2006, 149-153 |
| NM_030669 | PTPRO | 5800 | Keshet et al. Nature Genetics 38(2), 2006, 149-153 |
| NM_030670 | PTPRO | 5800 | Keshet et al. Nature Genetics 38(2), 2006, 149-153 |
| NM_030671 | PTPRO | 5800 | Keshet et al. Nature Genetics 38(2), 2006, 149-153 |
| NM_030760 | EDG8 | 53637 | Keshet et al. Nature Genetics 38(2), 2006, 149-153 |
| NM_030806 | C1orf21 | 81563; 116492 | Keshet et al. Nature Genetics 38(2), 2006, 149-153 |
| NM_030920 | ANP32E | 81611 | Keshet et al. Nature Genetics 38(2), 2006, 149-153 |
| NM_031277 | RNF17 | 56163 | Keshet et al. Nature Genetics 38(2), 2006, 149-153 |
| NM_031283 | TCF7L1 | 83439 | Keshet et al. Nature Genetics 38(2), 2006, 149-153 |

TABLE 1-continued

| Accession | Symbol | GeneID | Reference |
|---|---|---|---|
| NM_031424 | C20orf55 | 83541 | Keshet et al. Nature Genetics 38(2), 2006, 149-153 |
| NM_031466 | NIBP | 83696 | Keshet et al. Nature Genetics 38(2), 2006, 149-153 |
| NM_031488 | L3MBTL2 | 83746 | Keshet et al. Nature Genetics 38(2), 2006, 149-153 |
| NM_031497 | PCDHA6 | 56142; 56145; 56134; 56147; 56146; 56139 | Keshet et al. Nature Genetics 38(2), 2006, 149-153 |
| NM_031856 | PCDHA6 | 56142; 56145; 56134; 56147; 56146; 56139 | Keshet et al. Nature Genetics 38(2), 2006, 149-153 |
| NM_031859 | PCDHA6 | 56142; 56145; 56134; 56147; 56146; 56139 | Keshet et al. Nature Genetics 38(2), 2006, 149-153 |
| NM_031860 | PCDHA6 | 56142; 56145; 56134; 56147; 56146; 56139 | Keshet et al. Nature Genetics 38(2), 2006, 149-153 |
| NM_031882 | PCDHA6 | 56142; 56145; 56134; 56147; 56146; 56139 | Keshet et al. Nature Genetics 38(2), 2006, 149-153 |
| NM_031883 | PCDHA6 | 56142; 56145; 56134; 56147; 56146; 56139 | Keshet et al. Nature Genetics 38(2), 2006, 149-153 |
| NM_031901 | MRPS21 | 54460 | Keshet et al. Nature Genetics 38(2), 2006, 149-153 |
| NM_031912 | SYT15 | 83849 | www.methdb.de/ and/or www.mdanderson.org/ |
| NM_031922 | REPS1 | 85021 | Keshet et al. Nature Genetics 38(2), 2006, 149-153 |
| NM_031934 | RAB34 | 83871 | Keshet et al. Nature Genetics 38(2), 2006, 149-153 |
| NM_031994 | RNF17 | 56163 | Keshet et al. Nature Genetics 38(2), 2006, 149-153 |
| NM_032034 | SLC4A11 | 83959 | Keshet et al. Nature Genetics 38(2), 2006, 149-153 |
| NM_032087 | PCDHGC3 | 5098; 26025; 56108; 56112; 9708; 56109 | Keshet et al. Nature Genetics 38(2), 2006, 149-153 |
| NM_032094 | PCDHGC3 | 5098; 26025; 56108; 56112; 9708; 56109 | Keshet et al. Nature Genetics 38(2), 2006, 149-153 |
| NM_032098 | PCDHGC3 | 5098; 26025; 56108; 56112; 9708; 56109 | Keshet et al. Nature Genetics 38(2), 2006, 149-153 |
| NM_032099 | PCDHGC3 | 5098; 26025; 56108; 56112; 9708; 56109 | Keshet et al. Nature Genetics 38(2), 2006, 149-153 |
| NM_032100 | PCDHGC3 | 5098; 26025; 56108; 56112; 9708; 56109 | Keshet et al. Nature Genetics 38(2), 2006, 149-153 |

TABLE 1-continued

| Accession | Symbol | GeneID | Reference |
|---|---|---|---|
| NM_032101 | PCDHGC3 | 5098; 26025; 56108; 56112; 9708; 56109 | Keshet et al. Nature Genetics 38(2), 2006, 149-153 |
| NM_032109 | OTP | 23440 | www.methdb.de/ and/or www.mdanderson.org/ |
| NM_032134 | QRICH2 | 84074 | Keshet et al. Nature Genetics 38(2), 2006, 149-153 |
| NM_032140 | C16orf48 | 84080 | Keshet et al. Nature Genetics 38(2), 2006, 149-153 |
| NM_032192 | PPP1R1B | 84152 | Keshet et al. Nature Genetics 38(2), 2006, 149-153 |
| NM_032256 | TMEM117 | 84216 | Keshet et al. Nature Genetics 38(2), 2006, 149-153 |
| NM_032303 | HSDL2 | 84263 | Keshet et al. Nature Genetics 38(2), 2006, 149-153 |
| NM_032391 | PRAC | 84366 | Keshet et al. Nature Genetics 38(2), 2006, 149-153 |
| NM_032402 | PCDHGC3 | 5098; 26025; 56108; 56112; 9708; 56109 | Keshet et al. Nature Genetics 38(2), 2006, 149-153 |
| NM_032403 | PCDHGC3 | 5098; 26025; 56108; 56112; 9708; 56109 | Keshet et al. Nature Genetics 38(2), 2006, 149-153 |
| NM_032406 | PCDHGC3 | 5098; 26025; 56108; 56112; 9708; 56109 | Keshet et al. Nature Genetics 38(2), 2006, 149-153 |
| NM_032411 | ECRG4 | 84417 | Keshet et al. Nature Genetics 38(2), 2006, 149-153 |
| NM_032412 | ORF1-FL49 | 84418 | Keshet et al. Nature Genetics 38(2), 2006, 149-153 |
| NM_032603 | LOXL3 | 84695 | Keshet et al. Nature Genetics 38(2), 2006, 149-153 |
| NM_032625 | C7orf13 | 129790 | Keshet et al. Nature Genetics 38(2), 2006, 149-153 |
| NM_032803 | SLC7A3 | 84889 | Keshet et al. Nature Genetics 38(2), 2006, 149-153 |
| NM_032825 | ZNF382 | 84911 | Keshet et al. Nature Genetics 38(2), 2006, 149-153 |
| NM_032838 | ZNF566 | 84924 | Keshet et al. Nature Genetics 38(2), 2006, 149-153 |
| NM_032883 | C20orf100 | 84969 | Keshet et al. Nature Genetics 38(2), 2006, 149-153 |
| NM_032918 | RERG | 85004 | Keshet et al. Nature Genetics 38(2), 2006, 149-153 |
| NM_032945 | TNFRSF6B | 8771; 51750; 10139 | Keshet et al. Nature Genetics 38(2), 2006, 149-153 |
| NM_032961 | PCDH10 | 57575 | Keshet et al. Nature Genetics 38(2), 2006, 149-153 |
| NM_032967 | PCDH11X | 27328; 83259 | Keshet et al. Nature Genetics 38(2), 2006, 149-153 |
| NM_032968 | PCDH11X | 27328; 83259 | Keshet et al. Nature Genetics 38(2), 2006, 149-153 |
| NM_032969 | PCDH11X | 27328; 83259 | Keshet et al. Nature Genetics 38(2), 2006, 149-153 |
| NM_033126 | PSKH2 | 85481 | Keshet et al. Nature Genetics 38(2), 2006, 149-153 |
| NM_033135 | PDGFD | 80310; 414301 | Keshet et al. Nature Genetics 38(2), 2006, 149-153 |
| NM_033143 | FGF5 | 2250 | Keshet et al. Nature Genetics 38(2), 2006, 149-153 |
| NM_033224 | PURB | 5814 | Keshet et al. Nature Genetics 38(2), 2006, 149-153 |
| NM_033302 | ADRA1A | 148 | Keshet et al. Nature Genetics 38(2), 2006, 149-153 |
| NM_033303 | ADRA1A | 148 | Keshet et al. Nature Genetics 38(2), 2006, 149-153 |
| NM_033304 | ADRA1A | 148 | Keshet et al. Nature Genetics 38(2), 2006, 149-153 |
| NM_033445 | HIST3H2A | 92815 | Keshet et al. Nature Genetics 38(2), 2006, 149-153 |
| NM_033624 | FBXO21 | 23014 | Keshet et al. Nature Genetics 38(2), 2006, 149-153 |
| NM_052902 | STK11IP | 114790 | www.methdb.de/ and/or www.mdanderson.org/ |
| NM_052954 | CYYR1 | 116159 | Keshet et al. Nature Genetics 38(2), 2006, 149-153 |
| NM_052961 | SLC26A8 | 116369 | Keshet et al. Nature Genetics 38(2), 2006, 149-153 |
| NM_052978 | TRIM9 | 114088 | Keshet et al. Nature Genetics 38(2), 2006, 149-153 |
| NM_054021 | GPR101 | 83550 | Keshet et al. Nature Genetics 38(2), 2006, 149-153 |
| NM_054108 | HRASLS5 | 117245 | Keshet et al. Nature Genetics 38(2), 2006, 149-153 |
| NM_058165 | MOGAT1 | 116255 | Keshet et al. Nature Genetics 38(2), 2006, 149-153 |
| NM_078485 | COL9A1 | 1297 | Keshet et al. Nature Genetics 38(2), 2006, 149-153 |
| NM_080552 | SLC32A1 | 140679 | Keshet et al. Nature Genetics 38(2), 2006, 149-153 |
| NM_080617 | CBLN4 | 140689 | Keshet et al. Nature Genetics 38(2), 2006, 149-153 |
| NM_080671 | KCNE4 | 23704 | Keshet et al. Nature Genetics 38(2), 2006, 149-153 |
| NM_080742 | B3GAT2 | 135152 | Keshet et al. Nature Genetics 38(2), 2006, 149-153 |
| NM_130773 | CNTNAP5 | 129684 | Keshet et al. Nature Genetics 38(2), 2006, 149-153 |
| NM_130900 | RAET1L | 154064 | Keshet et al. Nature Genetics 38(2), 2006, 149-153 |
| NM_133180 | EPS8L1 | 54869 | Keshet et al. Nature Genetics 38(2), 2006, 149-153 |
| NM_133266 | SHANK2 | 22941 | Keshet et al. Nature Genetics 38(2), 2006, 149-153 |
| NM_133338 | RAD17 | 5884 | Keshet et al. Nature Genetics 38(2), 2006, 149-153 |
| NM_133339 | RAD17 | 5884 | Keshet et al. Nature Genetics 38(2), 2006, 149-153 |

TABLE 1-continued

| Accession | Symbol | GeneID | Reference |
|---|---|---|---|
| NM_133340 | RAD17 | 5884 | Keshet et al. Nature Genetics 38(2), 2006, 149-153 |
| NM_133341 | RAD17 | 5884 | Keshet et al. Nature Genetics 38(2), 2006, 149-153 |
| NM_133342 | RAD17 | 5884 | Keshet et al. Nature Genetics 38(2), 2006, 149-153 |
| NM_133343 | RAD17 | 5884 | Keshet et al. Nature Genetics 38(2), 2006, 149-153 |
| NM_133344 | RAD17 | 5884 | Keshet et al. Nature Genetics 38(2), 2006, 149-153 |
| NM_133489 | SLC26A10 | 65012 | Keshet et al. Nature Genetics 38(2), 2006, 149-153 |
| NM_133493 | CD109 | 135228 | Keshet et al. Nature Genetics 38(2), 2006, 149-153 |
| NM_133642 | LARGE | 9215 | Keshet et al. Nature Genetics 38(2), 2006, 149-153 |
| NM_138290 | RPIB9 | 154661 | Keshet et al. Nature Genetics 38(2), 2006, 149-153 |
| NM_138718 | SLC26A8 | 116369 | Keshet et al. Nature Genetics 38(2), 2006, 149-153 |
| NM_138996 | CNTNAP5 | 129684 | Keshet et al. Nature Genetics 38(2), 2006, 149-153 |
| NM_139204 | EPS8L1 | 54869 | Keshet et al. Nature Genetics 38(2), 2006, 149-153 |
| NM_139316 | AMPH | 273 | Keshet et al. Nature Genetics 38(2), 2006, 149-153 |
| NM_144497 | AKAP12 | 9590 | Keshet et al. Nature Genetics 38(2), 2006, 149-153 |
| NM_144725 | FLJ25439 | 153657 | Weber et al. Nature Genetics 37(8), 2005, 853-862 |
| NM_145725 | TRAF3 | 7187 | Keshet et al. Nature Genetics 38(2), 2006, 149-153 |
| NM_145726 | TRAF3 | 7187 | Keshet et al. Nature Genetics 38(2), 2006, 149-153 |
| NM_152562 | CDCA2 | 157313 | Weber et al. Nature Genetics 37(8), 2005, 853-862 |
| NM_152854 | CD40 | 958 | Keshet et al. Nature Genetics 38(2), 2006, 149-153 |
| NM_153819 | RASGRP2 | 10235 | Keshet et al. Nature Genetics 38(2), 2006, 149-153 |
| NM_170696 | ALDH1A2 | 8854 | Keshet et al. Nature Genetics 38(2), 2006, 149-153 |
| NM_170697 | ALDH1A2 | 8854 | Keshet et al. Nature Genetics 38(2), 2006, 149-153 |
| NM_170775 | KCNN2 | 3781 | Keshet et al. Nature Genetics 38(2), 2006, 149-153 |
| NM_171827 | CD8A | 925 | Keshet et al. Nature Genetics 38(2), 2006, 149-153 |
| NM_172337 | OTX2 | 5015 | www.methdb.de/ and/or www.mdanderson.org/ |
| NM_173479 | LOC126248 | 126248 | www.methdb.de/ and/or www.mdanderson.org/ |
| NM_174869 | IDH3G | 3421 | Keshet et al. Nature Genetics 38(2), 2006, 149-153 |
| NM_175052 | ST8SIA4 | 7903 | Keshet et al. Nature Genetics 38(2), 2006, 149-153 |
| NM_175611 | GRIK1 | 2897 | Keshet et al. Nature Genetics 38(2), 2006, 149-153 |
| NM_175709 | CBX7 | 23492 | www.methdb.de/ and/or www.mdanderson.org/ |
| NM_175768 | GRIK2 | 2898 | Keshet et al. Nature Genetics 38(2), 2006, 149-153 |
| NM_176095 | CDK5RAP3 | 80279 | Keshet et al. Nature Genetics 38(2), 2006, 149-153 |
| NM_176096 | CDK5RAP3 | 80279 | Keshet et al. Nature Genetics 38(2), 2006, 149-153 |
| NM_177555 | TRO | 7216 | Keshet et al. Nature Genetics 38(2), 2006, 149-153 |
| NM_177556 | TRO | 7216 | Keshet et al. Nature Genetics 38(2), 2006, 149-153 |
| NM_177557 | TRO | 7216 | Keshet et al. Nature Genetics 38(2), 2006, 149-153 |
| NM_177558 | TRO | 7216 | Keshet et al. Nature Genetics 38(2), 2006, 149-153 |
| NM_177959 | DOK5 | 55816 | Keshet et al. Nature Genetics 38(2), 2006, 149-153 |
| NM_178154 | FUT8 | 2530 | Keshet et al. Nature Genetics 38(2), 2006, 149-153 |
| NM_178155 | FUT8 | 2530 | Keshet et al. Nature Genetics 38(2), 2006, 149-153 |
| NM_178156 | FUT8 | 2530 | Keshet et al. Nature Genetics 38(2), 2006, 149-153 |
| NM_178157 | FUT8 | 2530 | Keshet et al. Nature Genetics 38(2), 2006, 149-153 |
| NM_181457 | PAX3 | 5077 | Keshet et al. Nature Genetics 38(2), 2006, 149-153 |
| NM_181458 | PAX3 | 5077 | Keshet et al. Nature Genetics 38(2), 2006, 149-153 |
| NM_181459 | PAX3 | 5077 | Keshet et al. Nature Genetics 38(2), 2006, 149-153 |
| NM_181460 | PAX3 | 5077 | Keshet et al. Nature Genetics 38(2), 2006, 149-153 |
| NM_181461 | PAX3 | 5077 | Keshet et al. Nature Genetics 38(2), 2006, 149-153 |
| NM_181466 | ITGB4BP | 3692 | Keshet et al. Nature Genetics 38(2), 2006, 149-153 |
| NM_181467 | ITGB4BP | 3692 | Keshet et al. Nature Genetics 38(2), 2006, 149-153 |
| NM_181468 | ITGB4BP | 3692 | Keshet et al. Nature Genetics 38(2), 2006, 149-153 |
| NM_181469 | ITGB4BP | 3692 | Keshet et al. Nature Genetics 38(2), 2006, 149-153 |
| NM_181505 | PPP1R1B | 84152 | Keshet et al. Nature Genetics 38(2), 2006, 149-153 |
| NM_181657 | LTB4R | 1241 | www.methdb.de/ and/or www.mdanderson.org/ |
| NM_181689 | NNAT | 4826 | Keshet et al. Nature Genetics 38(2), 2006, 149-153 |
| NM_182609 | ZNF677 | 342926 | Weber et al. Nature Genetics 37(8), 2005, 853-862 |
| NM_198265 | SPO11 | 23626 | Keshet et al. Nature Genetics 38(2), 2006, 149-153 |
| NM_198287 | ING4 | 51147 | Keshet et al. Nature Genetics 38(2), 2006, 149-153 |
| NM_198407 | GHSR | 2693 | Keshet et al. Nature Genetics 38(2), 2006, 149-153 |
| NM_198570 | UNQ739 | 375567 | www.methdb.de/ and/or www.mdanderson.org/ |
| NM_198849 | LOC283514 | 283514 | Weber et al. Nature Genetics 37(8), 2005, 853-862 |
| NM_199051 | FAM5C | 339479 | www.methdb.de/ and/or www.mdanderson.org/ |
| NM_199076 | CNNM2 | 54805 | Keshet et al. Nature Genetics 38(2), 2006, 149-153 |
| NM_199077 | CNNM2 | 54805 | Keshet et al. Nature Genetics 38(2), 2006, 149-153 |
| NM_199231 | GDNF | 2668 | Keshet et al. Nature Genetics 38(2), 2006, 149-153 |
| NM_199234 | GDNF | 2668 | Keshet et al. Nature Genetics 38(2), 2006, 149-153 |
| NM_199425 | VSX1 | 30813 | Keshet et al. Nature Genetics 38(2), 2006, 149-153 |
| NM_199426 | ZFP64 | 55734 | Keshet et al. Nature Genetics 38(2), 2006, 149-153 |
| NM_199427 | ZFP64 | 55734 | www.methdb.de/ and/or www.mdanderson.org/ |
| NM_199427 | ZFP64 | 55734 | Keshet et al. Nature Genetics 38(2), 2006, 149-153 |
| NM_201647 | STAMBP | 10617 | Keshet et al. Nature Genetics 38(2), 2006, 149-153 |
| NM_201999 | ELF2 | 1998; 26472 | Keshet et al. Nature Genetics 38(2), 2006, 149-153 |
| NM_206827 | RASL11A | 387496 | Weber et al. Nature Genetics 37(8), 2005, 853-862 |
| NM_206866 | BACH1 | 571 | Keshet et al. Nature Genetics 38(2), 2006, 149-153 |

TABLE 1-continued

| Accession | Symbol | GeneID | Reference |
|---|---|---|---|
| NM_206961 | LTK | 4058 | Keshet et al. Nature Genetics 38(2), 2006, 149-153 |
| NM_207121 | C20orf55 | 83541 | Keshet et al. Nature Genetics 38(2), 2006, 149-153 |
| NM_213622 | STAMBP | 10617 | Keshet et al. Nature Genetics 38(2), 2006, 149-153 |
| NP_536846 | | | www.methdb.de/ and/or www.mdanderson.org/ |
| NR_002196 | | | www.methdb.de/ and/or www.mdanderson.org/ |

See also Ilana Keshet, et al., Nature Genetics 38, 149-153 (1 Feb. 2006) and Gerd P Pfeifer, et al., Expert Opinion on Medical Diagnostics, September 2007, Vol. 1, No. 1, Pages 99-108, each of which is incorporated herein by reference.

As used herein, the term "adenoma" refers to a benign tumor of glandular origin. Although these growths are benign, over time they may progress to become malignant. As used herein the term "colorectal adenoma" refers to a benign colorectal tumor in which the cells form recognizable glandular structures or in which the cells are clearly derived from glandular epithelium.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), Hot-start PCR (see, e.g., U.S. Pat. Nos. 5,773,258 and 5,338,671; each herein incorporated by reference in their entireties), intersequence-specfic PCR, inverse PCR (see, e.g., Triglia, et alet al. (1988) Nucleic Acids Res., 16:8186; herein incorporated by reference in its entirety), ligation-mediated PCR (see, e.g., Guilfoyle, R. et alet al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et alet al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons."

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, (Hologic, Inc.) and are described, e.g., in U.S. Pat. Nos. 5,846,717, 5,985,557, 5,994,069, 6,001,567, 6,090,543, and 6,872,816; Lyamichev et al., Nat. Biotech., 17:292 (1999), Hall et al., PNAS, USA, 97:8272 (2000), and US 2009/0253142, each of which is herein incorporated by reference in its entirety for all purposes); enzyme mismatch cleavage methods (e.g., Variagenics, U.S. Pat. Nos. 6,110,684, 5,958,692, 5,851,770, herein incorporated by reference in their entireties); polymerase chain reaction; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Barnay Proc. Natl. Acad Sci. USA 88, 189-93 (1991)); and sandwich hybridization methods (e.g., U.S. Pat. No. 5,288,609, herein incorporated by reference in its entirety).

As used herein, the terms "complementary" or "complementarity" used in reference to polynucleotides (i.e., a sequence of nucleotides) refers to polynucleotides related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "primer" refers to an oligonucleotide, whether occurring naturally, as in a purified restriction digest, or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like). The primer is typically single stranded for maximum efficiency in amplification, but may alternatively be partially or completely double stranded. The portion of the primer that hybridizes to a template nucleic acid is sufficiently long to prime the synthesis of extension products in the presence of the inducing agent. The exact lengths of the primers will depend on many factors, including temperature, source of primer and the use of the method. Primers may comprise labels, tags, capture moieties, etc.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5-(carboxyhydroxyl-methyl)uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) Meth Enzymol. 68: 90-99; the phosphodiester method of Brown et al. (1979) Meth Enzymol. 68: 109-151; the diethylphosphoramidite method of Beaucage et al. (1981) Tetrahedron Lett. 22: 1859-1862; the triester method of Matteucci et al. (1981) J Am Chem Soc. 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

A "sequence" of a biopolymer refers to the order and identity of monomer units (e.g., nucleotides, amino acids, etc.) in the biopolymer. The sequence (e.g., base sequence) of a nucleic acid is typically read in the 5' to 3' direction.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," and "variant" refer to a gene or gene product that displays modifications in sequence and or functional properties (i.e., altered characteristics) when compared to the wild-type gene or gene product. It is noted that naturally occurring mutants can be isolated; these are identified by the fact that they have altered characteristics when compared to the wild-type gene or gene product.

As used herein, the term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment polypeptide are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (e.g., hnRNA); introns may contain regulatory elements (e.g., enhancers). Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

As used herein, the terms "multimethylation," "series methylation" and "specific methylation" are used interchangeably to refer to defined combinations of CpG sites or loci in a marker sequence must be methylated to call that sequence methylated in a coordinate or multimethylation assay. For example, a specific methylation assay of the CpG sites for BMP3 might require that the CpG positions at 23, 34, 53, 61, 70, and 74, numbered by reference to FIGS. 1A and 1B, all be methylated in order for a sample to be classified as methylated at the BMP3 marker. Specific methylation of BMP3 is not limited to this set of particular loci, but may include more, fewer, or a different collection of CpG loci. The CpG loci selected for co-analysis in a multimethylation assay are preferably selected. e.g., by analysis of normal (non-adenoma, non-cancer) samples to identify CpG methylation combinations that are less frequently represented in normal samples. In preferred embodiments, combinations of methylation sites are selected to produce good signal-to-noise in cancer and adenoma samples (i.e., the mean multimethylation at a particular combination of loci in cancer samples divided by the mean multimethylation in at those loci in normal samples is high).

As used herein, the terms "individual" and "average" methylation are used interchangeably to refer to analyses in which each CpG locus is analyzed individually, such that all molecules in which that base is methylated are included in a count, regardless of the methylation status of other loci, e.g., in the same marker. Generally, the methylation percentages of all the loci in a marker/region are then averaged, to produce a percent methylation figure for that marker.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to a delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

As used herein, the term "information" refers to any collection of facts or data. In reference to information stored or processed using a computer system(s), including but not limited to internets, the term refers to any data stored in any format (e.g., analog, digital, optical, etc.). As used herein, the term "information related to a subject" refers to facts or data pertaining to a subject (e.g., a human, plant, or animal). The term "genomic information" refers to information pertaining to a genome including, but not limited to, nucleic acid sequences, genes, allele frequencies, RNA expression levels, protein expression, phenotypes correlating to genotypes, etc. "Allele frequency information" refers to facts or data pertaining to allele frequencies, including, but not limited to, allele identities, statistical correlations between the presence of an allele and a characteristic of a subject (e.g., a human subject), the presence or absence of an allele in an individual or population, the percentage likelihood of an allele being present in an individual having one or more particular characteristics, etc.

DESCRIPTION OF THE DRAWINGS

FIGS. 1A and 1B provide sequence and CpG information for exemplary marker regions used in the present analysis. For each target gene, the native sequence of the region is shown in the top line. Unmethylated C-residues that would be converted by bisulfite and amplification to Ts are shown as T residues. Candidate methylation positions are shown boxed. Reference numbering for base and CpG positions is shown above each native sequence. Primer locations for amplification are shown as a row of underlined base positions.

FIGS. 2 A-J provide tables showing analyses of normal, adenoma, and cancer samples in which the average methylation was determined at each of the indicated CpG positions, in the indicated marker regions. For each marker, the numbered CpG positions are as indicated by the reference numbers in FIGS. 1A and 1B. The Mean methylation at each specific locus is shown at the bottom of each column for normal, adenoma, and cancer samples. The ratio of normal/ mutant methylation for each locus (a methylation ratio at each locus) is shown at the bottom of each column of the Adenoma and Cancer sample data. The Mean columns on the right of each table indicate the average of methylation across all indicated CpG loci for each of the samples. The Mean and SD values across all normal samples at all loci are as indicated below each table of values from normal samples.

FIGS. 3 A-I provide tables showing the analyses of normal, adenoma, and cancer samples in which average methylation across all of the CpG loci indicated in FIGS. 2A-J were calculated for each marker in each sample. For the normal samples in FIG. 3A, the average, standard deviation and the mean plus 2 or 3 standard deviations for each marker are indicated. For the adenoma and cancer samples, shaded cells in FIGS. 3B and 3C indicate a positive result, reflected as an average methylation value for that marker that is greater than the mean methylation+3 standard deviations determined for that marker in the normal samples.

FIGS. 3D and 3E show the calculated effect of a 20-fold dilution of adenoma and cancer DNA into normal DNA, FIGS. 3F and 3G show a calculated 10-fold dilution, and FIGS. 3H and 3I show a calculated 5-fold dilution. In each of the calculated dilutions, the average methylation for a marker is divided by the 20, 10, or 5, added to the mean methylation of the normal DNA for that marker. Shaded cells in FIGS. 3D-3I indicate an average methylation value for that marker that is greater than the mean methylation+2 standard deviations (specificity of 97.5%) determined for that marker in the normal samples.

Below each of FIGS. 3B-3I, the percentage of positive values for each marker in the sample type and dilution for that panel are indicated. The percentage of samples giving a positive signal for at least one of the Vimentin, BMP3, Septin 9 and TFPI2 markers are indicated at the bottom of each panel.

Figure 4A:
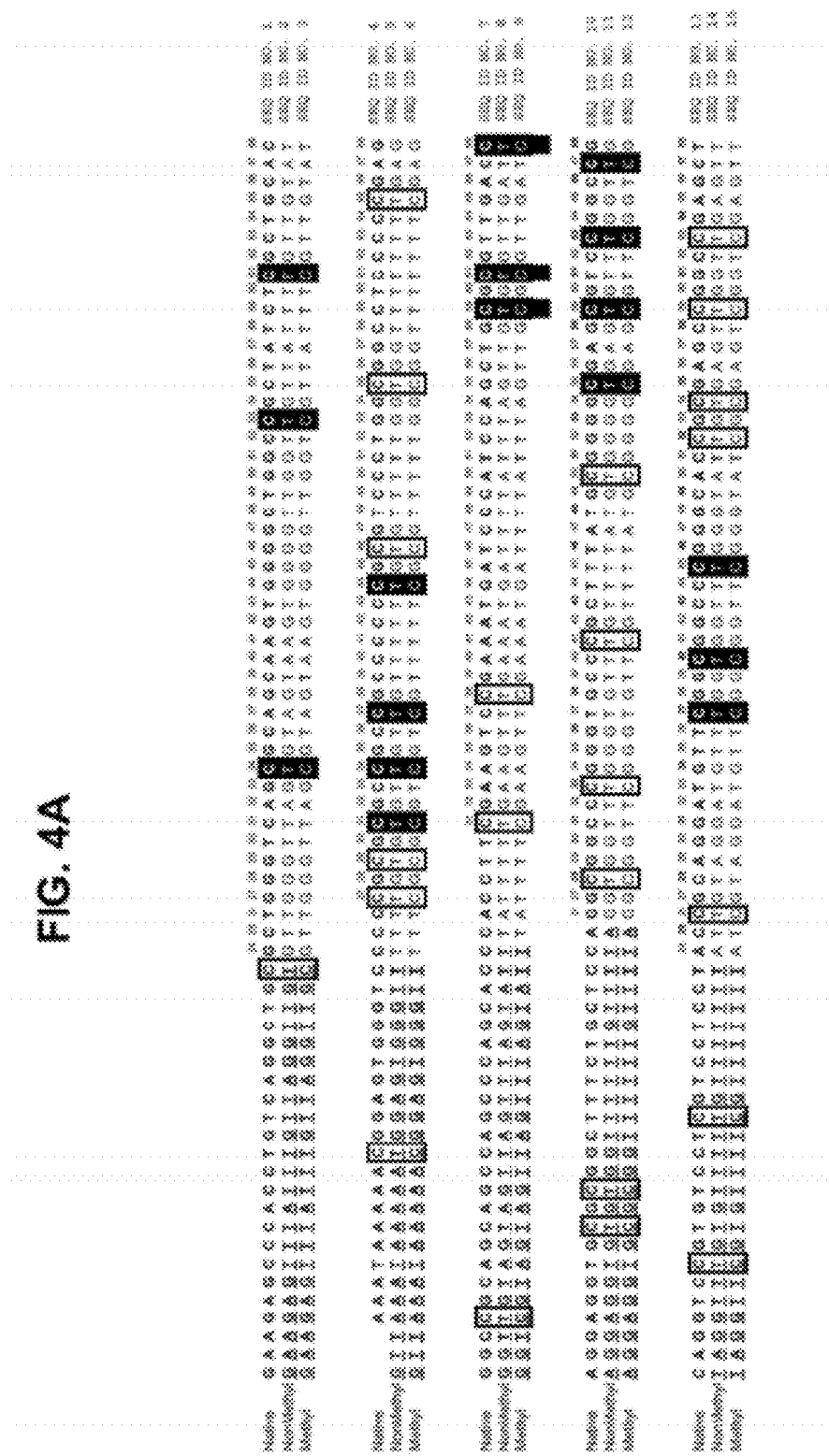

FIGS. 4A and 4B provide sequence and CpG information for exemplary genes used in the present analysis. The CpG loci in each marker gene included in the defined subsets of CpG loci for coordinate methylation analysis in colorectal adenoma and cancer samples are shown with a black background and in white typeface.

FIGS. 5 A-I provide tables showing the analyses of normal, adenoma, and cancer samples in which methylation was determined at each of the indicated CpG positions in the indicated marker regions (i.e., samples were assayed for the percentage of DNA copies that displayed methylation at all of the CpG loci in the defined subset). Each marker was tested at each of the CpG loci in the defined subsets indicated in FIGS. 4A and 4B and the percentage methylation data reflects the percentage of marker copies having methylation at all of the tested CpG loci (coordinate methylation or "multimethylation" analysis). For the normal samples in FIG. 5A, the mean multimethylation, standard deviation and the mean plus 2 or 3 standard deviations for each marker are indicated. For the adenoma and cancer samples, shaded cells in FIGS. 5B and 5C indicate a positive result, reflected as multimethylation value for that marker that is greater than the mean multimethylation+3 standard deviations determined for that marker in the normal samples.

FIGS. 5D and 5E show the calculated effect of a 20-fold dilution of adenoma and cancer DNA into normal DNA, FIGS. 5F and 5G show a calculated 10-fold dilution, and 5H and 5I show a calculated 5-fold dilution. In each of the calculated dilutions, the average multimethylation for a marker is divide by the 20, 10, or 5, added to the mean multimethylation of the normal DNA for that marker. Shaded cells in FIGS. 5D-5I indicate an average multimethylation value for that marker that is greater than the mean multimethylation+2 standard deviations (specificity of 97.5%) determined for that marker in the normal samples.

Below each of FIGS. 5B-5I, the percentage of positive values for each marker in the sample type and dilution for that panel are indicated. The percentage of samples giving a positive signal for at least one of the vimentin, BMP3, Septin 9 and TFPI2 markers are indicated at the bottom of each panel.

Figure 6:
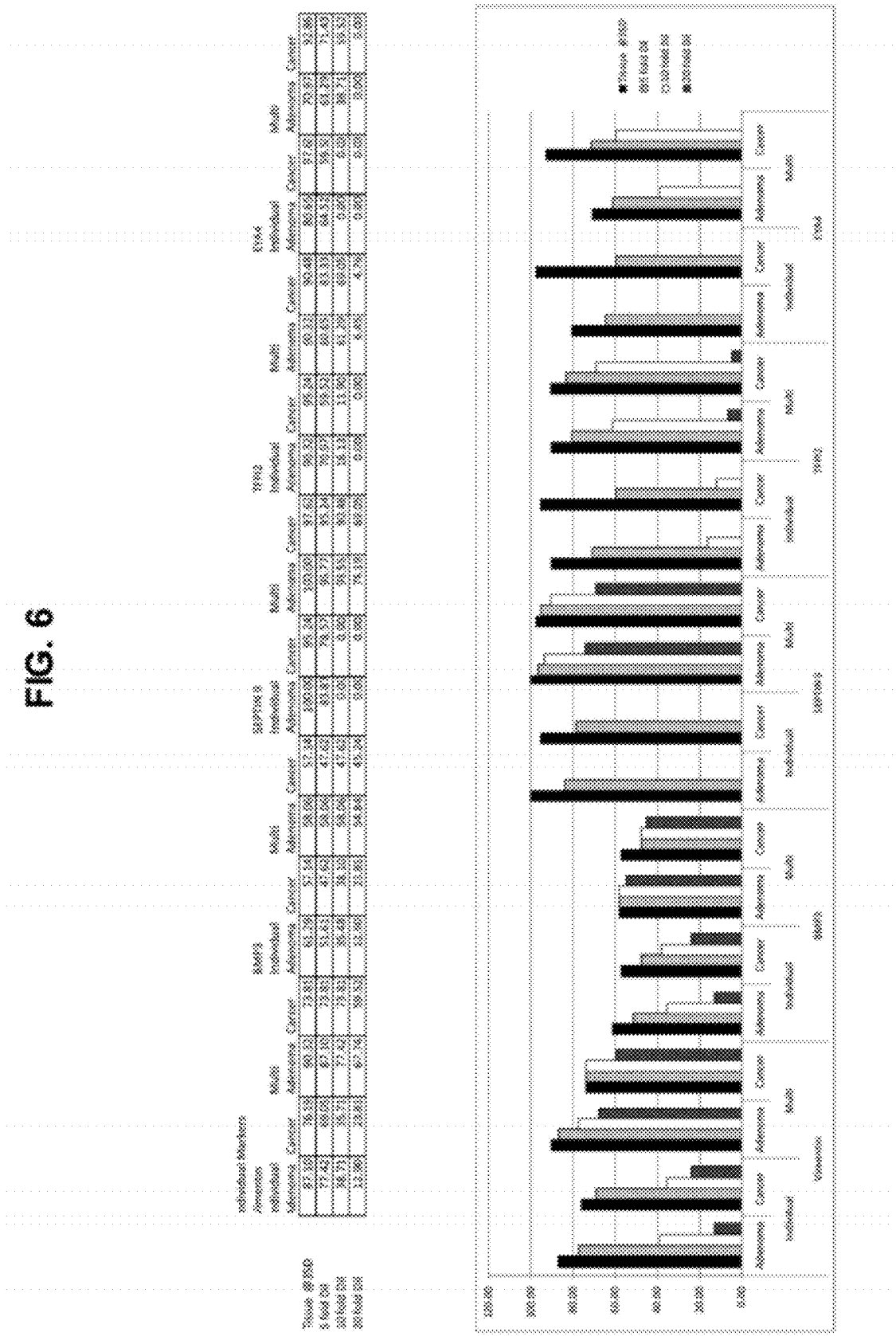

FIG. 6 shows a table and graph comparing the percent positive values calculated for each marker in adenoma and cancer samples, as indicated, using either individual/average methylation or multimethylation analysis methods to test each of the indicated markers, at each of the indicated calculated dilutions.

Figure 7:
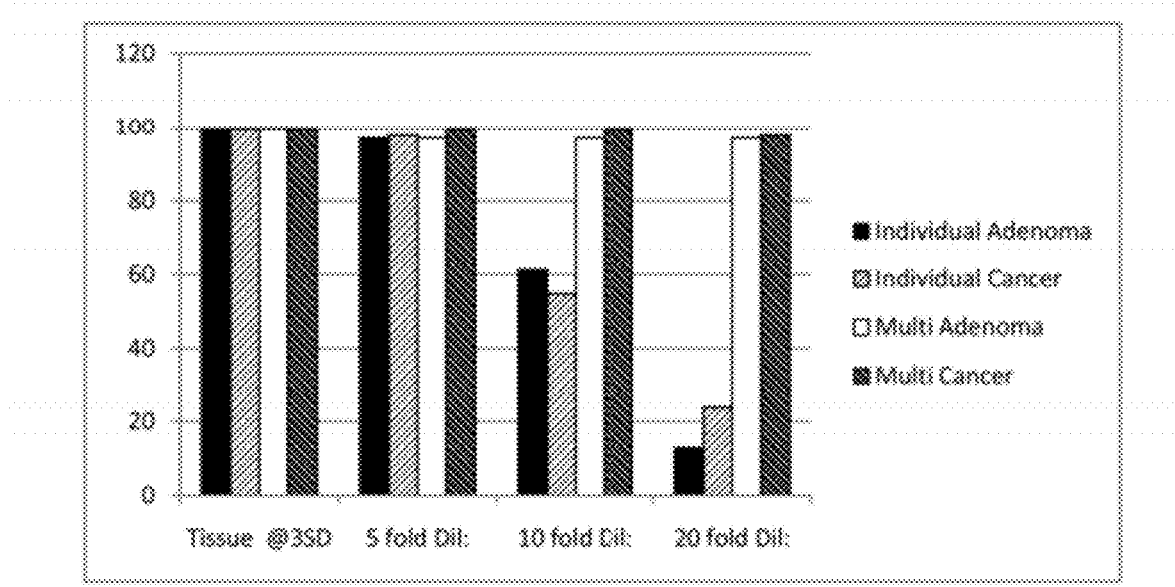

FIG. 7 shows a table and graph comparing the percent positive values determined in adenoma and cancer samples, determined using the four markers with the lowest mean background in these samples (vimentin, BMP3, Septin9, TFPI2), using either the individual/average methylation or the multimethylation analysis method, at each of the indicated calculated dilutions into normal DNA.

DETAILED DESCRIPTION OF THE INVENTION

Embodiments of the invention are described in this summary, and in the Summary of the Invention, above, which is incorporated here by reference. Although the invention has been described in connection with specific embodiments, it should be understood that the invention as claimed should not be unduly limited to such specific embodiments.

The present invention relates to methods and compositions for determination of, and uses of, specific methylation patterns indicative of adenoma and carcinoma. In particular, the invention relates to analysis of defined subsets of CpG loci that are coordinately methylated in DNAs from cancer and adenoma samples, methods for identifying coordinately methylated loci, and methods of using analysis of coordinately methylated loci in one or more markers or regions in the design of assays for adenoma and cancer having improved sensitivity and specificity.

The present invention relates to the observation that, within marker nucleic acids for which methylation status is indicative of cellular status, e.g., cancerous, pre-cancerous, normal, etc., a subset of the individual methylation loci, e.g., CpG loci, in non-normal cells generally displays a greater degree of methylation relative to the background levels of methylation observed at corresponding loci in normal cells, while other methylation loci in the non-normal cells may exhibit levels of methylation that are closer to background levels. In some embodiments, the degree of methylation observed for a particular locus in plurality of cancerous or pre-cancerous cells relative to normal cells is expressed as a methylation ratio.

Some embodiments of the present invention relate to screening known or suspected marker genes to identify specific methylation loci that exhibit greater ratios of disease-associated methylation relative to background methylation, as compared to other marker genes or other loci in the same marker gene. In some preferred embodiments, the present invention relates to coordinate methylation analysis, to measure the degree to which a marker molecule or a sample exhibits methylation at all of a plurality of selected loci.

The present invention relates to analyzing methylation statuses of a defined set of individual CpG loci in methylation markers (or target regions within such markers) in a significant enough number of individual DNA molecules in adenoma samples or cancer samples to identify defined subsets of CpG loci that have advantageous methylation ratios compared to other loci in the same adenoma or cancer samples. A defined subset of CpG loci that have advantageous methylation ratios in a sample may comprise the entirety of a set of CpG loci in a particular marker or target region of a marker, or it may be fewer than all of the CpG loci in the characterized region of the marker.

Conventional methods of analyzing methylation status of a marker generally involve analysis of a mixed population of molecules. For example, amplification of a marker nucleic acid from a sample generally produces a mixture of amplicons coming from many copies of a target molecule. If the amplification conditions are not selective for a gene variant, the amplicon product contains a mixture of the variant and the normal or wildtype DNA. Even if primers are specific for a mutation or for a particular methylation site, when DNA is amplified from many copies of target DNA derived from many cells, there can be heterogeneity in other base positions in the resulting amplicon. If these mixed amplicons are sequenced directly, the resulting sequence traces reveal the consensus sequence of the mixed population, and particular sequences or mutations present in a small portion of the population are essentially undetectable. Although some researchers have sequenced individual clones from such amplifications to examine sequence information for individual molecules from the mixture, only small numbers of molecules have been analyzed and the data gathered did not suggest any that any specific loci within the markers predictably exhibited advantageous methylation ratios compared to other methylated loci within the same target, or that coordindated analysis of loci having advantageous methylation ratios could be useful in improving the specificity and sensitivity of assays in detection of neoplasms. An aspect of the present invention is based on the observation that collecting methylation ratio information from a very large number of individual molecules in both normal and non-normal samples reveals that some methylation loci in marker regions or sequences exhibit a greater degree of methylation in non-normal cells compared to background (methylation at the same loci in normal cells) than do other individual loci in the same marker region or gene. These loci in non-normal sequences that have a greater level of methylation compared to background can be viewed as being particularly advantageous in that they are easier to identify over the background level of methylation observed in normal cells. One aspect of this advantage is that analysis of these particular loci permits identification of cancer-associated methylation with more sensitivity, and in a greater background of normal cells.

The present invention also relates to the observation that coordinated analysis of multiple loci provides a significantly enhanced level of sensitivity in the identification of cancerous or precancerous cells, especially in samples that may also comprise a significant number of normal cells. For example, FIG. 6 compares the sensitivity of detecting adenoma and cancer cells. For each of the indicated marker genes, the methylation was either determined as an average across the marker region (e.g., the mean methylation in the vimentin marker across all of loci 26, 37, 40, 45, 52, 54, 59, 63, and 74; see FIGS. 3A-I), indicated as "Individual" average methylation, or as a percentage of molecules displaying methylation at all of a subset of selected loci (e.g., methylation in the vimentin marker at all three of loci 37, 40 and 45; see FIGS. 5A-I), i.e., coordinate methylation analysis of multiple individual loci, indicated as "multi". The sensitivities for the same samples are also shown in calculated 5, 10 or 20-fold dilutions into normal DNA. FIG. 6 shows that, while assay sensitivities may be similar in DNA analyzed directly from tissue without dilution, as the amount background from normal DNA is increased at the larger dilutions, the coordinate methylation analysis is shown to be far more sensitive than the average methylation analysis. For example, in the analysis of Septin9, the adenoma and cancer samples can be detected above background only in the undiluted and 5-fold dilution profiles when average methylation across the marker is analyzed, while these same samples can be detected with over about 69-74% sensitivity at 20-fold dilution, and 90-93% sensitivity at 10-fold dilution, when coordinate methylation analysis of loci 37, 40 and 45 is used.

In some embodiments, the present invention provides a method for designing a methylation assay to identify a disease state, comprising I) selecting at least one sequence for analysis; II) determining the methylation status of a plurality of loci in the sequence in a population of normal cells and a population of non-normal cells to determine an average rate of methylation for each of the plurality of loci each both normal and non-normal cells; and III) identifying at least two loci in said plurality of loci having advantageous methylation ratios.

Figure 1A:
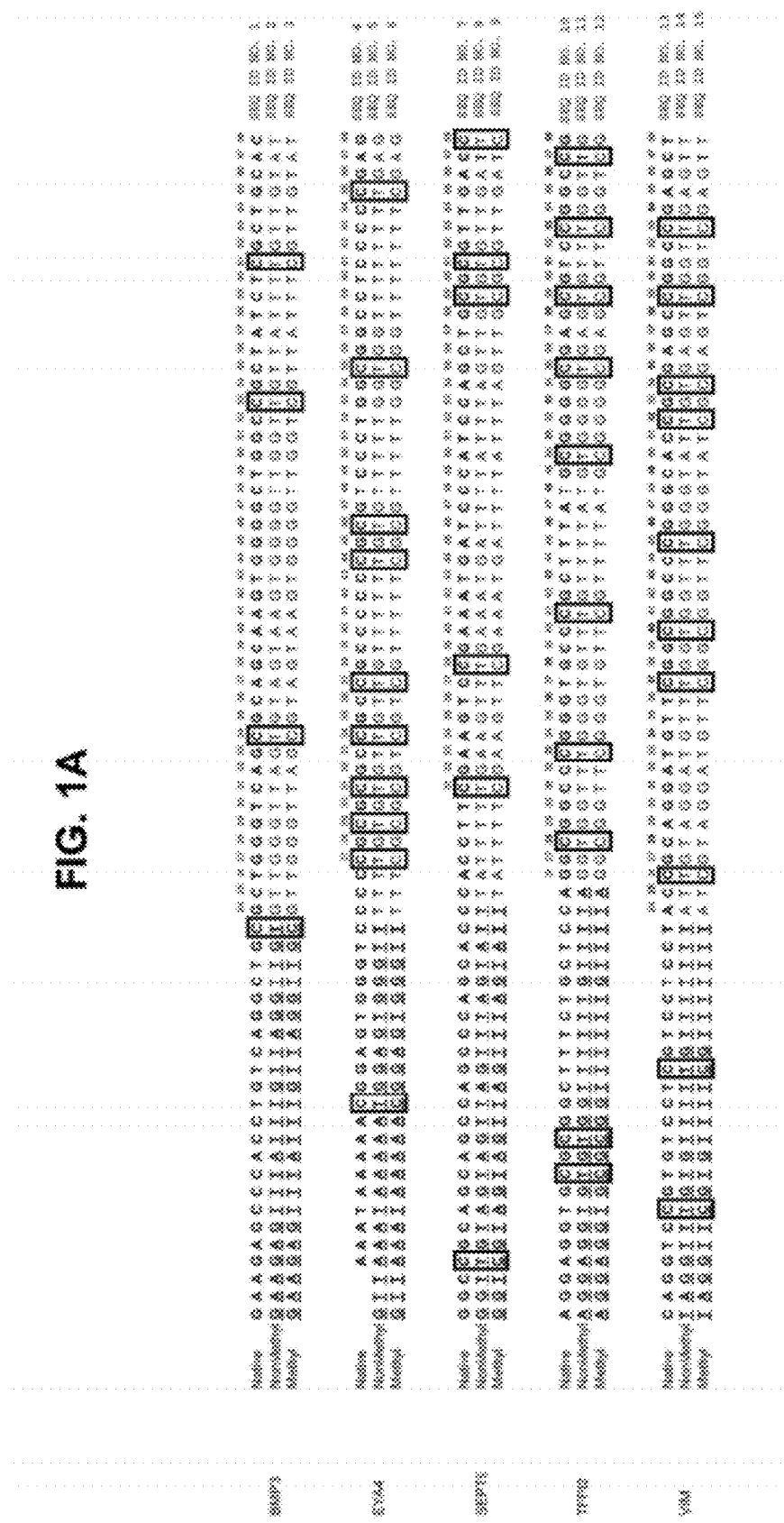

I. Selection of sequence(s). Methylation markers associated with particular disease states have been identified for a number of disease states. For example, colorectal neoplasm-specific marker include, e.g., bmp-3, bmp-4, SFRP2, vimentin, septin9, ALX4, EYA4, TFPI2, NDRG4, FOXE1, long DNA, BAT-26, K-ras, APC, melanoma antigen gene, p53, BRAF, and PIK3CA. Additional markers include but are not limited those in Table 1, above. Analysis of candidate methylation loci to identify those with advantageous methylation ratios may comprise analysis of every locus in a target sequence (e.g., every CpG) or it may comprise analysis of a subset of the methylation loci. In some embodiments, CpGs are selected for analysis by their location in particular methylation hotspots, while in other embodiments, loci for analysis may be conveniently located with respect to primer binding sites or other sequence features. FIG. 1A provides an exemplary selection of marker neoplasm-associated markers with each of the C residues in the CpG loci indicated by a box. For each target gene, the native sequence of the region is shown in the top line and the sequences for unmethylated and methulated DNA as they would appear following bisulfite conversion and amplification are shown below. Unmethylated C-residues that would be converted by bisulfite and amplification to T residues are shown as Ts.

In some embodiments, the present invention provides use of a nucleic acid detection assay to coordinately analyze a plurality of the advantageous loci in a sample, thereby determining the disease state of cells in sample.

II. Determining methylation ratios for loci in the selected sequence(s). As discussed above, determining a methylation ratio for a locus comprises determining an average rate of methylation for that locus in a population of normal cells and determining the average rate of methylation at the same locus in a population of non-normal cells. As noted above, commonly used methods of methylation analysis of marker genes are performed on mixed nucleic acids, e.g., amplicons produced from unfractionated DNA from a mixed population of cells (such as DNA purified from a multicellular tissue sample). While some studies have analyzed individual clones of amplicons made from unfractionated sample DNA, the numbers of clones analyzed has typically been too small to reveal significant or reproducible differences in methylation ratios at individual CpG loci within the sequences. For example, in their comparison of highly methylated genes in colorectal cancer, Zou, et al., analyzed only six clones from each sample. (Zou, et al., Cancer Epidemiol Biomarkers Prey 2007; 16(12):2686), while Weisenberg, et al. used The present invention comprises large-scale analysis of individual DNA molecules, for example, by direct sequencing of individual DNA molecules, or by sequencing of clonally amplified DNA.

While not limiting the present invention to any particular methods, methods of clonally amplifying individual copies of nucleic acids (e.g., using PCR) can be used in the rapid analysis of large numbers of individual markers from normal and non-normal samples. Single-molecule amplification methods may comprise use of microchambers, emulsion reactions, "bridge PCR" on solid supports, or any of a number of established methods of segregating the amplification products arising from individual target molecules. Following single molecule amplification, amplicons can be sequenced.

Improved methods of sequencing individual molecules directly obviate the need to clone molecules into cells or, in some methods, the need to clonally amplify prior to sequencing. Elimination of cloning into cells makes analysis of much larger collections of molecules dramatically more efficient. Platforms for individual molecule sequencing include the 454 FLX™ or 454 TITANIUM™ (Roche), the SOLEXA™/Illumina Genome Analyzer (Illumina), the HELISCOPE™ Single Molecule Sequencer (Helicos Biosciences), the Ion Personal Genome Machine (Ion Torrent), and the SOLID™ DNA Sequencer (Life Technologies/Applied Biosystems) instruments, as well as other platforms still under development by companies such as Intelligent Biosystems and Pacific Biosystems. Although the chemistry by which sequence information is generated varies for the different next-generation sequencing platforms, all of them share the common feature of generating sequence data from a very large number of individual sequencing templates, in sequencing reactions that are run simultaneously. Data from the reactions are collected using, e.g., a flow cell, a chemical or optical sensor, and/or scanner, and sequences are assembled and analyzed using bioinformatics software.

In certain preferred embodiments, the present invention provides methods of analysis of methylation markers using digital sequencing to identify neoplasm-associated methylation loci that have methylation ratios that are statistically significantly advantageous compared to other loci in the same markers. In preferred embodiments, digital sequencing is done in a highly or massively parallel fashion, providing higher precision in identifying CpG methylation sites having advantageous methylation ratios.

For the massively parallel digital sequencing methods mentioned above, each molecule is analyzed for methylation at each CpG locus, so the percentage of DNA copies having methylation at any combination of the CpG loci can be analyzed after the experimental run. Further, each particular marker sequence, e.g., each target nucleic acid molecule, or clonal amplicon may be interrogated many, many times, e.g., at least 100 times, sometimes over 1000 times, and in some instances over 100,000 times, or as many as 500,000 times. Thus, patterns of coordinate methylation indicative of cancer or adenoma that would be undetectable in analysis of a handful of individual target molecules may be revealed.

III. Selection of a Subset of Methylation Loci for Coordinate Analysis

As noted above, determination of the methylation status of a set of CpG loci in a large number of copies marker DNA from both normal samples and non-normal samples (e.g., adenoma or cancer samples) reveals that certain CpG loci in marker genes or regions may tend to be coordinately methylated. Further, design of nucleic acid detection assays to interrogate a plurality of CpG loci for which coordinate methylation is indicative of adenoma or cancer in a sample can provide an assay that has improved signal-to-noise compared to assays that survey average percent methylation across entire marker genes.

One aspect of selecting a subset of CpG loci comprises selecting loci that have been determined to be coordinately methylated by use, e.g., of digital analysis methods. Another aspect comprises selecting CpG loci determined to have advantageous methylation ratios when normal DNA is compared to adenoma or cancer DNA. Assay designs may, but need not, make use of a CpG locus having the most advantageous methylation ratio compared to other loci in the same marker. In some embodiments, selection of a plurality of CpG loci as a subset comprises selecting the plurality of loci having the most advantageous methylation ratios. In other embodiments, selection of a plurality of CpG loci as a subset comprises selecting the locus having the most advantageous methylation ratio, then selecting at least additional CpG loci that are conveniently situated with respect to the first selected locus for the configuration of a particular nucleic acid detection assay (e.g., the selection of CpG loci having particular proximity to each other for configuring an invasive cleavage assay, ligation assay, amplification assay, etc.) in order to interrogate all of the selected CpG loci on copies of the target DNA in a single assay. In some embodiments, a candidate subset of CpG loci is further analyzed to determine the percentage of copies of marker DNA from non-normal samples that are coordinately methylated at those candidate loci, and that have little or no coordinated methylation in normal samples.

Analysis of Samples for Detection of Adenoma or Cancer

Conventional methods of methylation analysis, (e.g., conventional methylation-specific PCR, real time methylation-specific PCR, see, e.g., U.S. Pat. Nos. 5,786,146, 6,017,704, 6,200,756, 6,265,171,), typically analyze in a non-digital fashion, e.g., analyzing a mixture of co-amplified molecules derived from a mixture of DNA target nucleic acids, so that analysis of the amplified products provides sequence information that reflects that aggregate or average methylation status in the amplicon population, but does not provide information on the percentage of starting molecules having coordinated methylation at all of a plurality of CpG loci. In some instances researchers have analyzed a number of cloned amplicons, which can reveal the diversity in methylation in the CpG loci within a target marker gene. However, sequencing individual clones has not provided enough data to reveal statistically significant coordinate methylation of specific subsets of CpG loci.

In contrast to conventional methods, we sought to analyze methylation marker genes in a massively parallel digital sequencing fashion to identify statistically significant coordinate methylation of specific CpG loci associated with neoplasms (adenoma and carcinoma). This method of analysis allowed us to:
1. Analyze samples for coordinate methylation in a marker gene as a means of detecting neoplasms without the need for testing any genetic (mutation) markers
2. Analyze samples for coordinate methylation in a plurality of marker genes as a means of detecting neoplasms without the need for testing any genetic (mutation) markers We decided to use "digital" sequencing on a larger number of tissue samples obtained by biopsy from colorectal adenomas, colorectal cancers normal colorectal epithelia and other GI cancers and sequence a number of specific regions within several genes. This type of sequencing provides a methylation pattern for each individual methylated gene. For the first run we have 9 normal tissues, 38 adenomas and 36 cancer samples with the following markers—Vimentin, BMP3, Septin 9, TFPI2, 2 regions of LRAT, and EYA4.

Surprisingly we found that in some of the genes, the background observed as methylation in normal samples is randomly distributed in the sequences, while the methylation associated with cancer and adenoma is not. Thus, if certain rules are applied e.g. if all of C residues a, b, and c have to methylated in a diagnostic assay, then the number of DNA copies presenting methylation at all three positions in that sequence is reduced compared to the number of DNA copies displaying methylation at a subset of the positions. In some of the marker genes or regions tested, the reduction in number of DNA copies in normal DNA displaying methylation at all of the selected sites drops to a greater degree than it does in the DNA from cancer and/or adenoma sample, resulting in an significantly enhanced ratio of specific signal to background noise. For certain genes, the background from normal DNA is dramatically reduced by using multimethylation (coordinate methylation) analysis, while no equivalent reduction in signal from cancer and adenoma DNA is seen. For other genes the background in normal samples is less reduced and/or the signal from cancer DNA also decreases with multimethylation analysis, such that there is less or no net improvement in the signal-to-noise and the advantages of using a multimethylation analysis approached are less. Genes having favorable signal to noise in multimethylation analyses are readily determined empirically.

From the multimethyation data presented herein (see, e.g., FIGS. 2A-J) it is possible to:
a. Identify regions within the gene sequences that give higher discrimination between normal and non-normal (e.g., cancer and adenoma) cells;
b. Identify particular genes that have greater signal-to-noise (non-normal cell signal compared to normal cell background);
c. Identify particular methylation loci that have greater signal-to-noise;
d. Identify particular methylation loci that are coordinately methylation in adenoma and cancer samples but not in normal samples, such that detection coordinate methylation at these loci is a sensitive indicator of adenoma or cancer;
e. Identify genes with very low background methylation allowing for greater dilution of methylated DNA in normal DNA with less decrease in assay sensitivity;
f. Identify genes that are diagnostically complementary to each other, i.e., that when analyzed in combination produce diagnostic information of elevated sensitivity and/or elevated specificity compared to the genes analyzed alone.
g. Identify combinations of genes that give elevated sensitivity at elevated specificity, e.g., 100% sensitivity for cancer and adenoma at 100% specificity.

EXPERIMENTAL EXAMPLES

Example 1

Use of Digital PCR and Sequencing for the Identification of Specific Subsets of CpG Loci Methylated in Cancer and Adenoma Samples DNA extracted from frozen tissue samples was treated with an EPITECT bisulfite conversion kit (Qiagen) to convert non-methylated cytosines to uracil. Methylated cytosines remain unconverted. Primers for each gene region were designed for each sequence such that the composition of the amplification products remained the same as the original target sequences and methylated and non methylated sequences were amplified with equal efficiencies. Amplification of the dU-containing converted DNA produced amplicons having T-residues in place of the dU residues. The amplicons were then prepared for sequencing on the Illumina instrument. For each tissue sample, the amplification reaction for each target was prepared from the same sample of bisulfite-treated DNA.

After sequencing, the data was analyzed quantitatively as an average methylation similar to Sanger sequencing, but at a higher precision and resolution in that the combined signal at each position is calculated from individual molecules. For each amplicon sequence, a set of CpG loci was evaluated for percent methylation in the different tissues, to identify a subset the loci that were co-methylated more frequently in cancer and/or adenoma samples than in normal tissues.

Illumina Sequencing Protocol:
Sequencing was conducted according to the procedure recommended for the Illumina Genome Analyzer IIx, GAIIx, Data collection software ver. 2.5, and Pipeline analysis software ver 1.5. Briefly, the Illumina procedure comprises a) preparation of a library from sample DNA by attachment of known sequence tags that permit indexing, flow cell attachment, amplification, and sequencing; b) attachment of the library to a flow cell surface; c) bridge amplification to produce clusters of DNA fragments derived from single molecules, and d) sequencing in using iterative primer extension reactions using labeled reversible terminators to determine the nucleotide sequence of each cluster of amplicons. See, e.g., Bentley, et al, Nature 456, 53-59 (6 Nov.r 2008)/doi:10.1038/nature07517 with supplementary methods and data, incorporated herein by reference. Use of unique tag sequences for indexing permits analysis of multiple samples in a single flow cell. See, e.g., Craig, et al., Nat. Methods Nat Methods. 2008 October; 5(10):887-93 (Epub 14 Sep. 2008), incorporated herein by reference.

Sample Set: N=82, composed of tissue dna extracted from 42 colorectal cancers, 31 pre-cancerous adenomas and 9 normal colonic mucosa.

Flow Cell Configuration
Samples were indexed at 12 per lane for a total of 7 lanes. A flow cell is composed of 8 lanes, one of which is dedicated to a phiX quality control.

Library Preparation:
Tissue-extracted DNA from patients was bisulfite-treated and a 2-step amplification using approximately 10,000 genome copies of initial material was carried out. The first round used tailed (T1) (Illumina) primers specific for marker sequences. These tails were Illumina-derived sequences needed for round two. The second round (T2) (Illumina) PCR uses primers specific for the Illmuna tails added in T1, and incorporates the index, sequencing primer, and flow cell attachment sequences. During the library preparation, multiple qPCR checks were run on the samples to ensure equimolar representations of all amplicons in the libraries.

Primer Design:

Forward and reverse primers specific for regions with converted, non-CpG cytosines are designed (using, e.g., MethPrimer software) to amplify each of the specific biomarker sites in a non-methylation specific manner. When CpG cytosines cannot be avoided in the primer design, degenerate mixtures (C/T; G/A) are used those sites in the primers. If additional sequences outside the primary amplicon need to be queried, additional primers may be designed. If CpGs in the target sequence cannot be avoided, the primers may incorporate degenerate bases at CpG sites (BiSearch software).

Primers for second round PCR comprise sequences for Illumina flow cell attachment (bridge amplification sites), sequencing primer sites (for the sample read), index sites, and sequencing primers sites (for the indexing read). Each of the primer sets (x) has 12 different index tags, for a total of 12x sets. Index-independent primer sets (n=x) are optimized on converted non-methylated DNA (e.g., human DNA) and converted methylated DNA. For example, the control DNAs are amplified, purified (e.g, using AMPURE treatment (Agencourt)), and run on an Agilent 2100 Bioanalyzer to assess the size and quantity of the amplified nucleic acids.

Experimental Steps:

DNA Isolation and Bisulfite Conversion:

1) DNA was extracted and purified from tissue using either DNAZOL (Invitrogen), or QIAAMP kits (Qiagen) and the concentration and purity was measured by absorbance (A230/A260/A280) using a Nanodrop ND-1000 spectrophotometer (Thermo Scientific). PICOGREEN fluorescence (Molecular Probes) was used in conjunction with a TECAN F-200 (Tecan) plate-reader for high samples exhibiting high A230 values.
2) Samples were adjusted to a concentration of at least 200 ng/uL using a Speedvac evaporation concentrator (Thermo Scientific), as necessary.
3) For each sample, 2 ug of DNA was bisulfite-treated using EPITECT 96-well plates (Qiagen).
4) Recovery was assessed by absorbance and OLIGOGREEN fluorescence (Molecular Probes) and the conversion efficiency was assessed with quantitative PCR using cytosine-containing, non-CpG primers specific for unconverted DNA. Conversion efficiency was determined to be greater than 99%

First-Round PCR:
5) The 84 samples were amplified in reactions with 30 ng DNA using marker-specific (T1) primer sets. The number of cycles used was specific for each marker set and was empirically determined by the initial control reactions on both methylated and unmethylated DNA. The number of cycles is approximately set at the mean calculated Ct value. For example, the following numbers of cycles were used for the indicated markers:
TFPI12; 26 cycles
SEPT9; 27 cycles
BMP3; 28 cycles
VIM; 28 cycles
EYA4; 29 cycles
6) The amplified product from each reaction was purified using AMPURE beads (Agencourt), with elution in EB buffer (Qiagen).
7) The product for each marker was quantified by qPCR as described above, using a T2 primer set. Master plates were prepared containing equal amounts of each biomarker for each sample.

Second-Round PCR:
8) The first-round samples were then amplified with the 12 T2 indexed primers.
9) The product for each reaction was again purified and concentrations measured with qPCR, this time with flow-cell-specific primers and a standard curve created using serial dilution of PhiX control DNA.

Final Library Prep:
10) The 12 columns of each plate were combined into 1 master column in equimolar proportions. 1 uL of each library was loaded on a high sensitivity DNA chip (Agilent) and run on the Bioanalyzer. A final qPCR was also performed on the 480 LightCycler (Roche) with the PhiX standards.
11) The libraries were sequenced on the Illumina Instrument and the sequence data obtained for each marker for each sample.
12) Average methylation at each CpG site was calculated for each marker for each sample. See FIGS. 2A-J.
13) The percentage of molecules methylated at all of the CpG loci in a defined subset of the CpG loci in each marker was calculated for each marker for each sample. See FIGS. 5A-I.

All publications and patents mentioned in the above specification are herein incorporated by reference. Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A method of making an assay for detecting DNA amplified from a bisulfite-treated methylated marker DNA in the presence of DNA amplified from the bisulfite-treated unmethylated marker DNA that exhibits background methyation,
comprising:
   a) isolating marker DNA from a first plurality of samples in which said marker DNA is unmethylated DNA exhibiting background methylation and from a second plurality of samples in which said marker DNA is methylated;
   b) treating said isolated marker DNA with bisulfite under conditions wherein unmethylated cytosine residues are converted to uracil residues to produce converted isolated marker DNA;
   c) processing said converted isolated marker DNA using a digital sequencing and/or digital polymerase chain reaction (PCR) to determine the methylation status for three or more CpG loci in each of at least 1000 individual copies of said isolated marker DNA from each of said first plurality and said second plurality of samples;
   d) for each of said three or more CpG loci, determining a ratio between a mean methylation at that CpG locus in said first plurality of samples to a mean methylation at the corresponding CpG locus in said second plurality of samples;
   e) selecting a defined subset of at least three CpG loci for which the percentage of individual copies of the marker DNA from said first plurality of samples that are methylated at all of said at least three CpG loci in said defined subset is less than the percentage of individual copies of said marker DNA from said second plurality of samples that are methylated at all of said at least three CpG loci in said defined subset; and
   f) creating a DNA detection assay that detects the methylation status of all of the at least three CpG loci in said defined subset of CpG loci in a strand of the bisulfite-treated marker DNA,
   wherein said creating comprises synthesizing a primer oligonucleotides configured to amplify a segment of marker DNA comprising said defined subset of CpG loci, and wherein the absence of methylation at any of the CpG loci in said defined subset of CpG loci in a strand of said marker DNA produces an assay result classifying that strand of said marker DNA as not methylated.

2. The method of claim 1, wherein the plurality of individual copies of a marker DNA analyzed in each of said first and said second plurality of samples comprises at least 10,000.

3. The method of claim 1, wherein the plurality of individual copies of a marker DNA analyzed in each of said first and said second plurality of samples comprises at least 100,000.

4. The method of claim 1, wherein each of said first and said second plurality of samples comprises at least 10.

5. The method of claim 1, wherein each of said first and said second plurality of samples comprises at least 100.

6. The method of claim 1, wherein said defined subset of CpG loci comprises at least four CpG loci.

7. method of claim 1, wherein said defined subset of CpG loci comprises at least five CpG loci.

8. The method of claim 1, wherein said DNA detection assay comprises at least one assay selected from the group consisting of a primer extension assay, a nucleic acid amplification assay, a structure-specific cleavage assay, 5' nuclease cleavage assay, an invasive cleavage assay, and a ligation assay.

* * * * *

UNITED STATES PATENT AND TRADEMARK OFFICE
CERTIFICATE OF CORRECTION

PATENT NO. : 9,637,792 B2
APPLICATION NO. : 13/364978
DATED : May 2, 2017
INVENTOR(S) : David A. Ahlquist et al.

Page 1 of 1

It is certified that error appears in the above-identified patent and that said Letters Patent is hereby corrected as shown below:

Claim 1, Column 53, Line 48:
Should read:
methylation

Signed and Sealed this
Eighth Day of August, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 15

<210> SEQ ID NO 1
<211> LENGTH: 121
<212> TYPE: DNA
<213> ORGANISM: Homo sapiens

<400> SEQUENCE: 1
```
gaagagccca cctgtcaggc tgcgctgggt cagcgcagca agtggggctg gccgctatct    60
cgctgcaccc ggccgcgtcc cgggctccgt gcgccctcgc cccagctggt ttggagttca   120
a                                                                  121

<210> SEQ ID NO 2
<211> LENGTH: 121
<212> TYPE: DNA
<213> ORGANISM: Artificial
<220> FEATURE:
<223> OTHER INFORMATION: Synthetic

<400> SEQUENCE: 2
gaagagttta tttgttaggt tgtgttgggt tagtgtagta agtggggttg gttgttattt    60
tgttgtattt ggttgtgttt tgggttttgt gtgttttgt tttagttggt ttggagttta    120
a                                                                  121

<210> SEQ ID NO 3
<211> LENGTH: 121
<212> TYPE: DNA
<213> ORGANISM: Artificial
<220> FEATURE:
<223> OTHER INFORMATION: Synthetic

<400> SEQUENCE: 3
gaagagttta tttgttaggt tgcgttgggt tagcgtagta agtggggttg gtcgttattt    60
cgttgtattc ggtcgcgttt cgggtttcgt gcgttttcgt tttagttggt ttggagttta    120
a                                                                  121

<210> SEQ ID NO 4
<211> LENGTH: 129
<212> TYPE: DNA
<213> ORGANISM: Homo sapiens

<400> SEQUENCE: 4
aaataaaaac ggagtgggtc ccccgcgcgc cgccgccccc cgcgtccctg gcggcctccc    60
ccgaggcccc cggcggcctc acgagcccgc agtagccggt ggcgacgtcg ccccgcccc   120 acctccccg                                                          129

<210> SEQ ID NO 5
<211> LENGTH: 132
<212> TYPE: DNA
<213> ORGANISM: Artificial
<220> FEATURE:
<223> OTHER INFORMATION: Synthetic

<400> SEQUENCE: 5
gttaaataaa aatggagtgg gttttttgtg tgttgttgtt ttttgtgttt tggtggttt     60 tttttgaggt ttttggtggt tttatgagtt tgtagtagtt ggtggtgatg ttgttttgt   120 tttattttt tg                                                       132

<210> SEQ ID NO 6
<211> LENGTH: 132
<212> TYPE: DNA
<213> ORGANISM: Artificial
<220> FEATURE:
<223> OTHER INFORMATION: Synthetic

<400> SEQUENCE: 6

```
gttaaataaa aacggagtgg gttttttcgcg cgtcgtcgtt tttcgcgttt ttggcggttt      60 tttcgaggt tttcggcggt tttacgagtt cgtagtagtc ggtggcgacg tcgttttcgt       120
tttatttttt tg                                                           132
```

<210> SEQ ID NO 7
<211> LENGTH: 99
<212> TYPE: DNA
<213> ORGANISM: Homo sapiens

<400> SEQUENCE: 7

```
ggccgcagca gccagcccag cacccacctt cgaagtccga aatgatccca tccagctgcg      60
cgttgaccgc ggggtccgac atgatggctg gtgggcagc                             99
```

<210> SEQ ID NO 8
<211> LENGTH: 99
<212> TYPE: DNA
<213> ORGANISM: Artificial
<220> FEATURE:
<223> OTHER INFORMATION: Synthetic

<400> SEQUENCE: 8

```
ggttgtagta gttagtttag tatttatttt tgaagtttga aatgatttta tttagttgtg      60
tgttgattgt ggggtttgat atgatggttg gtgggtagt                             99
```

<210> SEQ ID NO 9
<211> LENGTH: 99
<212> TYPE: DNA
<213> ORGANISM: Artificial
<220> FEATURE:
<223> OTHER INFORMATION: Synthetic

<400> SEQUENCE: 9

```
ggtcgtagta gttagtttag tatttatttt cgaagttcga aatgatttta tttagttgcg      60
cgttgatcgc ggggttcgat atgatggttg gtgggtagc                             99
```

<210> SEQ ID NO 10
<211> LENGTH: 116
<212> TYPE: DNA
<213> ORGANISM: Homo sapiens

<400> SEQUENCE: 10

```
aggaggtgcg cggctttctg ctccaggcgg cccgggtgcc cgctttatgc ggggcgagcg      60
tccggccgac ccccgccggg gcggagcctg aggggtggct gattcatgca cgggga          116
```

<210> SEQ ID NO 11
<211> LENGTH: 116
<212> TYPE: DNA
<213> ORGANISM: Artificial
<220> FEATURE:
<223> OTHER INFORMATION: Synthetic

<400> SEQUENCE: 11

```
aggaggtgtg tggtttttg ttttaggtgg tttgggtgtt tgttttatgt ggggtgagtg       60
tttggttgat ttttgttggg gtggagtttg aggggtggtt gatttatgta tgggga          116
```

<210> SEQ ID NO 12
<211> LENGTH: 116
<212> TYPE: DNA
<213> ORGANISM: Artificial
<220> FEATURE:
<223> OTHER INFORMATION: Synthetic

```
<400> SEQUENCE: 12
aggaggtgcg cggtttttg ttttaggcgg ttcgggtgtt cgttttatgc ggggcgagcg    60
ttcggtcgat tttcgtcggg gcggagtttg aggggtggtt gatttatgta cgggga       116

<210> SEQ ID NO 13
<211> LENGTH: 117
<212> TYPE: DNA
<213> ORGANISM: Homo sapiens

<400> SEQUENCE: 13
caggtccgtg tcctcgtcct cctaccgcag gatgttcggc ggcccgggca ccgcgagccg   60
gccgagctcc agccggagct acgtgactac gtccacccgc acctacagcc tgggcga     117

<210> SEQ ID NO 14
<211> LENGTH: 117
<212> TYPE: DNA
<213> ORGANISM: Artificial
<220> FEATURE:
<223> OTHER INFORMATION: Synthetic

<400> SEQUENCE: 14
taggtttgtg tttttgtttt tttattgtag gatgtttggt ggtttgggta ttgtgagttg   60
gttgagtttt agttggagtt atgtgattat gtttatttgt atttatagtt tgggtag     117

<210> SEQ ID NO 15
<211> LENGTH: 117
<212> TYPE: DNA
<213> ORGANISM: Artificial
<220> FEATURE:
<223> OTHER INFORMATION: Synthetic

<400> SEQUENCE: 15
taggttcgtg ttttcgtttt tttatcgtag gatgttcggc ggttcgggta tcgcgagtcg   60
gtcgagtttt agtcggagtt acgtgattac gtttattcgt atttatagtt tgggtag     117
```